(12) United States Patent
Donaldson et al.

(10) Patent No.: US 10,570,077 B2
(45) Date of Patent: Feb. 25, 2020

(54) SUBSTITUTED (4'-HYDROXYPHENYL)CYCLOHEXANE COMPOUNDS AND USES THEREOF AS SELECTIVE AGONISTS OF THE ESTROGEN RECEPTOR BETA ISOFORM

(71) Applicants: Marquette University, Milwaukee, WI (US); Concordia University, Inc., Mequon, WI (US)

(72) Inventors: William A. Donaldson, Milwaukee, WI (US); Daniel S. Sem, New Berlin, WI (US); Terrence S. Neumann, Milwaukee, WI (US)

(73) Assignees: Marquette University, Milwaukee, WI (US); Concordia University Inc., Mequon, WI (US)

( * ) Notice: Subject to any disclaimer, the term of this patent is extended or adjusted under 35 U.S.C. 154(b) by 183 days.

(21) Appl. No.: 15/162,057

(22) Filed: May 23, 2016

(65) Prior Publication Data
US 2016/0340279 A1    Nov. 24, 2016

Related U.S. Application Data

(63) Continuation-in-part of application No. PCT/US2014/066896, filed on Nov. 21, 2014.

(60) Provisional application No. 61/963,031, filed on Nov. 21, 2013.

(51) Int. Cl.
| C07C 39/17 | (2006.01) |
|---|---|
| C07C 39/23 | (2006.01) |
| C07C 251/44 | (2006.01) |
| C07C 59/54 | (2006.01) |
| C07C 69/732 | (2006.01) |

(52) U.S. Cl.
CPC .............. *C07C 39/17* (2013.01); *C07C 39/23* (2013.01); *C07C 59/54* (2013.01); *C07C 69/732* (2013.01); *C07C 251/44* (2013.01); *C07C 2601/14* (2017.05); *C07C 2601/18* (2017.05)

(58) Field of Classification Search
CPC ......... C07C 39/17; C07C 59/54; C07C 39/23; C07C 251/44
See application file for complete search history.

(56) References Cited

U.S. PATENT DOCUMENTS

| 3,564,060 A * | 2/1971 | Aldrich et al. ......... C07C 33/34 |
|---|---|---|
| | | 514/843 |
| 5,591,769 A | 1/1997 | Himmelsbach et al. |
| 6,107,299 A | 8/2000 | Jakobi et al. |
| 6,288,050 B1 | 9/2001 | Li et al. |
| 7,994,179 B2 | 8/2011 | Johannesson et al. |
| 9,271,969 B2 * | 3/2016 | Kim ................. A61K 31/429 |
| 2012/0149807 A1 * | 6/2012 | Asaumi .................. C07C 67/08 |
| | | 523/457 |

FOREIGN PATENT DOCUMENTS

| GB | 1086530 A | 10/1967 |
|---|---|---|
| WO | 2009081195 A1 | 7/2009 |
| WO | 2009127686 A1 | 10/2009 |
| WO | 2010086551 A1 | 8/2010 |
| WO | 2012112364 A1 | 8/2012 |

OTHER PUBLICATIONS

International Preliminary Report on Patentability for PCT/US14/066896 dated May 24, 2016.
Anderson, et al. Effects of conjugated equine estrogen in postmenopausal women with hysterectomy: the Women's Health Initiative randomized controlled trial. JAMA : the journal of the American Medical Association. 2004;291 (14):1701-12.
Beral V. Breast cancer and hormone-replacement therapy in the Million Women Study. Lancet. 2003;362 (9382):419-27.
Blair, R. M.; Fang, H.; Branham, W. S.; Hass, B. S.; Dial, S. L.; Moland, C. L; Tong, W.; Shi, L.; Perking, R.; Sheehan, D. M. Toxicol. Sci. 2000, 54, 138-153.
Bolger, R.; Wiese, T. E.; Ervin, K.; Nestich, S.; Checovich, W. Environ. Health Perspect. 1998, 106, 551-557.
Brody, J. G.; Rudel, R. A. Environ. Health Perspect. 2003, 111, 1007-1019.
Brzozowski, A. M.; Pike, A. C. W.; Dauter, Z.; Hubbard, R. E.; Bonn, T.; Engstrom, O.; Ohman, L.; Greene, G. L.; Gustafsson, J. A.; Carlquist, M. Nature, 1997, 389, 753-758.
Buteau-Lozano, Cancer. Res. 62, 4977-4984, Sep. 1, 2002.
Colborn, T.; Saal, F. S.; Soto, A. M. Environ. Health Perspect. 1993, 101, 378-384.
Costache, A. D.; Pullela, P. K.; Kashi, P.; Tomasiewicz, H.; Sem, D. S. Mol. Endocrinol. 2005, 19, 2979-2990.
Cross, J. B.; Thompson, D. C.; Rai, B. K.; Baber, J. C.; Fan, K. Y.; Hu, Y.; Humblet, C. J. Chem. Inf. Model. 2009, 49, 1455-1474.
De Riccardis, F.; Meo, D.; Izzo, I.; Di Filippo, M.; Casapullo, A. Eur. J. Org. Chem. 1998, 1965-1970.
Deroo, B. J.; Korach, K. S. J. Clin. Invest. 2006, 116, 561-570.
Frigoli, M.; Mehl, G. H. Eur. J. Org. Chem. 2004, 636-642.
DeOrazio, R. J.; Nikam, S. S.; Scott, I. L.; Sherer, B. A.; Wise, L. D. PCT Int. Appl. WO 01/81295 A1, 2001.
Gann PH, Morrow M. Combined hormone therapy and breast cancer: a single-edged sword. JAMA : the journal of the American Medical Association. United States2003. p. 3304-6.
He, Z.; Donaldson, W. A.; Yi, C. S. Org. Lett. 2003, 5, 1567-1569.
Huey, R.; Morris, B. M.; Olson, A. J.; Goodsell, D. S. J. Comput. Chem. 2007, 28, 1145-1152. Indigo Biosciences, Human Estrogen Receptor Technical Manual.
International Preliminary Report on Patentability for PCT/US2014/066896 dated May 24, 2017.

(Continued)

*Primary Examiner* — Jennifer M Kim
(74) *Attorney, Agent, or Firm* — Quarles & Brady LLP

(57) ABSTRACT

Disclosed are substituted (4'-hydroxylphenyl)cycloalkane compounds and there use as selective agonists of the estrogen receptor beta isoform (ERβ). The disclosed compounds may be formulated as pharmaceutical compositions and administered to treat diseases associated with ER activity, such as proliferative diseases and disorders and/or psychiatric diseases or disorders.

19 Claims, 21 Drawing Sheets

(56) References Cited

OTHER PUBLICATIONS

International Search Report for PCT/US2014/066896 dated May 28, 2015.
Irwin, J. J.; Shoichet, B. K. J. Chem. Inf. Model. 2005, 45, 177-182.
Lam, H. Y. P.; Begleiter, A.; Goldenberg, G. J. J. Med. Chem. 1979, 22, 200-202.
Levin, E. R. Mol. Endocrinol. 2005, 19, 1951-1959.
Li Ci, Malone KE, Porter PL, Weiss NS, Tang MT, Cushing-Haugen KL, et al. Relationship between long durations and different regimens of hormone therapy and risk of breast cancer. JAMA : the journal of the American Medical Association. 2003;289(24):3254-63. Epub Jun. 26, 2003. doi: 10.1001/jama.289.24.3254. PubMed PMID: 12824206.
Li, X.; Huang, J.; Yi, P.; Bambara, R. A.; Hilf, R.; Muyan, M. Mol. Cell. Biol. 2004, 24, 7681-7694.
Li, Z.; Zhang, H.; Gibson, M.; Li, J. Toxicology in Vitro 2012, 26, 769-774.
Manas, E. S.; Xu, Z. B.; Unwalla, R. J.; Somers, W. S. Structure 2004, 12, 2197-2207.
Miteva, M.A.; Lee, W.H.; Montes, M.O.; Villoutreix, B.O. J. Med. Chem. 2005, 48,6012-6022.
Morris, G. M.; Goodsell, D. S.; Halliday, R. S.; Huey, R.; Hart, W. E.; Belew, R. K; Olson, A. J. J. Comput. Chem. 1998, 19, 1639-1662.
Morris, G. M.; Huey, R.; Lindstrom, W.; Sanner, M. F.; Belew, R. K.; Goodsell, D. S.; Olson, A. J. J. Comput. Chem. 2009, 30, 2785-2791.
Nasir, M. S.; Jolley, M. E. Comb. Chem. High Throughput Screening 1999, 2, 177-190.
Norman, B.H.; Richardson, T.I.; Dodge, J.A.; Pfeifer, L.A.; Durst, G.L.; Wang, Y.; Durbin, J.D.; Krishnan, V.; Dinn, S.R.; Liu, S.; Reilly, J.E.; Ryter, K.T. Bioorg. Med. Chem. Lett. 2007, 17, 5082-5085.
Ohno, K.; Fukushima, T.; Santa, T.; Waizumi, N.; Tokuyama, H.; Maeda, M.; Imai, K. Anal. Chem. 2002, 74, 4391-4396.
Paganini-Hill A, Clark LJ. Preliminary assessment of cognitive function in breast cancer patients treated with tamoxifen. Breast Cancer Research and Treatment. 2000;64:165-76.
Pandey, R. K.; Wang, L.; Wallock, N. J.; Lindeman, S.; Donaldson, W. A. J. Org. Chem. 2008, 73, 7236-7245.
Parker, G.J.; Law, T.L.; Lenoch, F.J. Bolger, R.E. J. Biomol. Screen. 2000, 5, 77-88.
Payne, J.; Scholz, M.; Kortenhamp, A. Environ. Health Perspect. 2001, 109, 391-397.
Shiau, A.K.; Barstad, D.; Radek, J.T.; Meyers, M.J.; Nettles, K.W.; Katzenellenbogen, B.S.; Katzellenbogen, J.A.; Agard, D.A.; Greene, G.L. Nat. Struct. Biol. 2002, 9, 359-364.
Shoichet, B. K. Nature. 2004, 432, 862-865.
Song X, Pan ZZ. Estrogen receptor-beta agonist diarylpropionitrile counteracts the estrogenic activity of estrogen receptor-alpha agonist propylpyrazole-triol in the mammary gland of ovariectomized Sprague Dawley rats. The Journal of steroid biochemistry and molecular biology. 2012;130(1-2):26-35. Epub Jan. 24, 2012. doi: 10.1016/j.isbmb.2011.12.018. PubMed PMID: 22266284.
Suresh, P. S.; Kumar, A.; Kumar, R.; Sihn, V. P. J. Mol. Graphics Modell. 2008, 26, 845-849.
Suzuki, S.; Ohno, K.; Santa, T.; Imai, K. Anal. Sci. 2003, 19, 1103-1108.
Tuccinardi, T.; Bertini, S.; Martinelli, A.; Minutolo, F.; Ortore, G.; Placanica, G.; Prota, G.; Rapposelli, S.; Carleson, K. E.; Katzenellenbogen, J.A.; Macchia, M. J. Med. Chem. 2006, 49, 5001-5012.
Van Lipzig, M.M.H.; ter Laak, A.M.; Jongegan, A.; Vermeulen, N.P.E.; Wamelink, M.; Geerke, D.; Meerman, J.H.N. J. Med. Chem. 2004, 47, 1018-1030.
Written Opinion for PCT/US2014/066896 dated May 28, 2015.
Yaffe K, Krueger K, Sarkar S, Grady D, Barrett-Connor E, Cox DA, et al. Cognitive function in postmenopausal women treated with raloxifene. New England Journal of Medicine. 2001;344:1207-13.
Extended European Search Report for 14863768.9 dated Jun. 21, 2017.
Supplemental European Search Report for 14863768.9 dated Jul. 7, 2017.
Pandey, Rajesh, et al., "Reactivity of (2-Alkenyl-3-pentene-1,5-diyl) iron Complexes: Preparation of Functionalized Vinylcyclopropanes and Cycloheptadienes", J. Org. Chem., vol. 73, 2008, pp. 7236-7245, XP055343946.

* cited by examiner

SUBSTITUTED (4'-HYDROXYPHENYL)CYCLOHEXANE COMPOUNDS AND USES THEREOF AS SELECTIVE AGONISTS OF THE ESTROGEN RECEPTOR BETA ISOFORM

CROSS-REFERENCE TO RELATED PATENT APPLICATIONS

The present application is a continuation-in-part of International Application No. PCT/US2014/066896, filed on Nov. 21, 2014, and published on May 28, 2015, which International Application claims the benefit of priority under 35 U.S.C. § 119(e) to U.S. Provisional Patent Application No. 61/963,031, filed on Nov. 21, 2013, the contents of which are incorporated herein by reference in their entireties.

STATEMENT REGARDING FEDERALLY SPONSORED RESEARCH OR DEVELOPMENT

This invention was made with government support under Grant Nos. S10 RR019012, G1-M-42641, AI101975, and HL112639 awarded by the National Institutes of Health. The Government has certain rights in this invention.

BACKGROUND

The field of the invention relates to compounds that function as ligands for estrogen receptors (ERs). In particular, the field of the invention relates to substituted (4'-hydroxyphenyl)cycloalkane compounds that are specific agonists for the estrogen receptor beta (ERβ) and the use of such compounds in pharmaceutical compositions for treating diseases and disorders associated with ER activity.

Estrogens are important regulators of many physiological processes that include reproduction, cognition, cardiovascular health, and bone metabolism. (See, e.g., Deroo et al., "Estrogen Receptors and Human Disease," J. Clin. Invest. 116:561-570(2006). Based on their widespread role in a number of physiological processes, estrogens have been implicated in a number of diseases and disorders which include cell proliferative diseases and disorders (e.g., breast cancer, ovarian cancer, endometrial cancer, colorectal cancer, and prostate cancer), neurodegenerative diseases and disorders, cardiovascular disease, and osteoporosis to name a few. (See id.). In many of these diseases and disorders, estrogen mediates its effects through the estrogen receptors (ERs).

The ERs exist in 2 main forms, ERα and ERβ, which have different tissue expression patterns. (See Mueller et al. (2001), "Estrogen receptors and endocrine diseases: lessons from estrogen receptor knockout mice," Curr. Opin. Pharmacol. 1: 613-619). ERα and ERβ are encoded by separate genes, ESR1 and ESR2, respectively, found at different chromosomal locations, and numerous mRNA splice variants exist for both ERα and ERβ. (See, e.g., Hernyk et al., "Estrogen receptor mutations in human disease," (2004) Endocr. Rev. 25:869-898). Because of their role in estrogen-related diseases, ERα and ERβ have been targeted for development of specific ligands that modulate their activities. The ligand specificity of ERα and ERβ differ, and a ligand that binds and functions as an agonist or antagonist for ERα may or may not bind and function as an agonist or antagonist for ERβ.

One group of ligands for ERs that have been developed are the so-called "selective estrogen receptor modulators" or "SERMs" which include tamoxifen and raloxifene. Tamoxifen and raloxifene have been observed to exhibit tissue-specific estrogenic activity. For example, tamoxifen is an antagonist in the breast and has been a safe and effective adjuvant endocrine therapy for breast cancer for almost 20 years, but tamoxifen is an ER agonist in bone and uterus. (See, e.g., Deroo et al., "Estrogen Receptors and Human Disease," J. Clin. Invest. 116:561-570 (2006)). Raloxifene exhibits greater agonist activity in bone and less agonist activity in the uterus. (See Fabian et al., "Selective estrogen-receptor modulators for primary prevention of breast cancer," J. Clin. Oncol. 23:1644-1655 (2005)). Whether a ligand is an ER agonist or antagonist in a particular tissue depends on several factors, including which form of the estrogen receptor predominates in the particular tissue, in other words ERα or ERβ, where the ligand may exhibit different binding affinity and/or agonist/antagonist activity for ERα versus ERβ.

ERα and ERβ agonists have a wide range of biological effects that implicate disease such as cancer and disorders of the central nervous system (CNS). Clinical studies have indicated that administering estradiol (E2) in post-menopausal hormone replacement therapy (HRT) can lead to increased incidence of breast and endometrial cancer. (See Beral et al., "Breast cancer and hormone-replacement therapy in the Million Women Study," Lancet. 2003; 362 (9382:419-27. Epub 2003/08/21. PubMed PMID: 12927427; Gann et al., "Combined hormone therapy and breast cancer: a single-edged sword," JAMA: the journal of the American Medical Association. United States 2003. p. 3304-6; Li et al., "Relationship between long durations and different regimens of hormone therapy and risk of breast cancer," JAMA: the Journal of the American Medical Association. 2003; 289(24):3254-63. Epub 2003/06/26. doi: 10.1001/jama.289.24.3254. PubMed PMID: 12824206; and Anderson et al., "Effects of conjugated equine estrogen in postmenopausal women with hysterectomy: the Women's Health Initiative randomized controlled trial," JAMA: the journal of the American Medical Association. 2004; 291 (14):1701-12. Epub 2004/04/15. doi: 10.1001/jama.291.14.1701. PubMed PMID: 15082697). This effect is mediated predominantly by ERα, the dominant isoform present in the mammary gland and uterus. (See Song et al., "Estrogen receptor-beta agonist diarylpropionitrile counteracts the estrogenic activity of estrogen receptor-alpha agonist propylpyrazole-triol in the mammary gland of ovariectomized Sprague Dawley rats. The Journal of steroid biochemistry and molecular biology. 2012; 130(1-2):26-35. Epub 2012/01/24. doi: 10.1016/j.jsbmb.2011.12.018. PubMed PMID: 22266284).

The increased cancer risk has led to decreased usage of HRT in post-menopausal women. But, studies also have shown that HRT can provide a positive effect mediated primarily by ERβ, which is a decrease in the risk of dementia in post-menopausal women. (See Leblanc et al., "U.S. Preventive Services Task Force Evidence Syntheses, formerly Systematic Evidence Reviews. Hormone Replacement Therapy and Cognition. Rockville (Md.): Agency for Healthcare Research and Quality (US); 2002). As such, specific ERβ agonists can provide the CNS benefits of E2 with minimal side effects. However, current SERMs such as tamoxifen and raloxifene, are not specific for ERβ, have carcinogenic side effects, and provide little memory enhancement. (See Yaffe et al., "Cognitive function in postmenopausal women treated with raloxifene. New England Journal of Medicine. 2001; 344:1207-13; and Paganini-Hill et al., "Preliminary assessment of cognitive function in breast cancer patients treated with tamoxifen. Breast Cancer Research and Treatment. 2000; 64:165-76). Safer and more effective treatments can be developed by selectively targeting ERβ.

Thus, new ligands for estrogen receptors are desirable. In particular, new ligands that exhibit selective agonist or antagonist activity for ERβ versus ERα are desirable. These new ligands should be suitable for treating diseases and disorders associated with ER activity, such as cell proliferative diseases and disorders or psychiatric diseases and disorders. Such new ligands are disclosed herein in the form of substituted (4'-hydroxylphenyl)cycloalkane compounds.

SUMMARY

Disclosed are substituted (4'-hydroxylphenyl)cycloalkane compounds and their use as selective agonists of the estrogen receptor beta (ERβ). The disclosed compounds may be formulated as pharmaceutical compositions and administered to treat diseases associated with ER activity.

In some embodiments, the disclosed compounds have a Formula I or a hydroxy-protected form thereof:

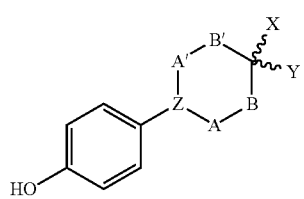

I where:
A-B is —CH₂CH₂—, —CH₂CH₂CH₂—, —CH₂CH₂CH₂—,

—CH₂CH₂CH—          —CH₂CH₂CH—
        |                                                    |
       COOH ,                            COOAlkyl, —CH₂CH═CH—, or —CH═CHCH₂—;
A'-B' is —CH₂CH₂—, or —CH═CH—;
Z is a carbon atom;
X is hydroxyl, alkyl, hydroxyalkyl, amino, or aminoalkyl;
Y is hydrogen, alkyl, or X and Y together form alkylidenyl, carboxyalkylidenyl, esteralkylidenyl, hydroxyalkylidenyl, aminoalkylidenyl, oxo, or oxime, or Y is —CH₂CH₂— and Y and Z form a bridge.

Optionally, when A-B is —CH₂CH₂—, then A'-B' is not —CH═CH—. Optionally, when A-B is —CH₂CH₂— and A'-B' is —CH₂CH₂—, then X is not hydroxyethyl and X is not aminomethyl. Optionally, when X is hydroxyalkyl, X is hydroxyl-C(1-6)alkyl, preferably hydroxy-C(1-3)alkyl. Optionally, when X is aminoalkyl, X is amino-C(1-6)alkyl, preferably amino-C(1-3)alkyl. Optionally, when X and Y together form carboxyalkylidenyl, X and Y form carboxy-C(1-6)alkylidenyl, preferably carboxy-C(1-3)alkylidenyl. Optionally, when X and Y together form esteralkylidenyl, X and Y form C(1-6)alkyl-ester-C(1-6)alkylidenyl, preferably C(1-3)alkyl-ester-C(1-3)alkylidenyl. Optionally, when X and Y together form hydroxyalkyldenyl, X and Y form hydroxy-C(1-6)alkylidenyl, preferably hydroxy-C(1-3)alkylidenyl. Optionally, when X and Y together form aminoalkylidenyl, X and Y form amino-C(1-6)alkylidenyl, preferably amino-C(1-3)alkylidenyl.

The disclosed compounds may include 4-substituted-(4'-hydroxyphenyl)cycloheptane compounds. In the disclosed compounds having Formula I, A-B may be —CH₂CH₂CH₂— and A'-B' may be —CH₂CH₂— and the disclosed compounds may have a Formula Ia:

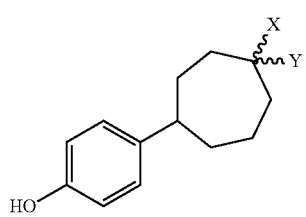

Ia where X and Y are as defined for Formula I.

The disclosed compounds may include 4-substituted-(4'-hydroxyphenyl)cycloheptane compounds having a carboxyl substitution or a carboxyalkylester substitution on the heptane ring. In the disclosed compounds having Formula I, A-B may be

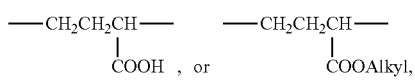

and A'-B' may be —CH₂CH₂— and the disclosed compounds may have a Formula Ia(i) or Formula Ia(ii):

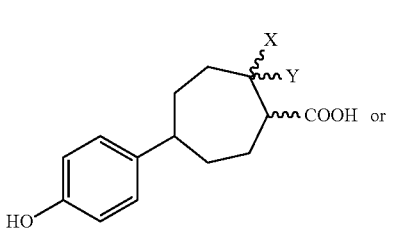

Ia(i)

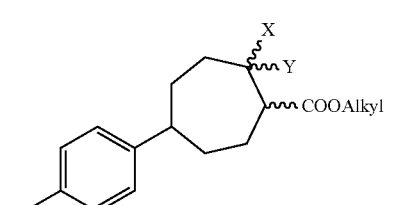

Ia(ii)

where X and Y are as defined for Formula I.

The disclosed compounds may include 4-substituted-(4'-hydroxyphenyl)cycloheptene compounds. In the disclosed compounds having Formula I, A-B may be —CH₂CH═CH—, and A'-B' may be —CH₂CH₂— or —CH═CH—, and the disclosed compounds may have a Formula Ia(iii), a Formula Ia(iv), or a Formula Ia(v):

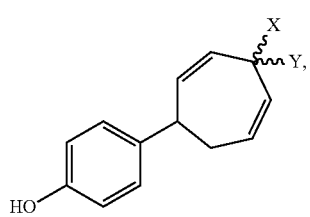

Ia(iii)

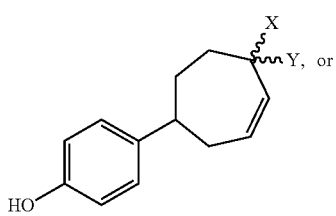

Ia(iv)

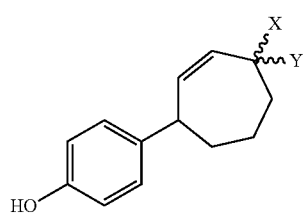

Ia(v)

where X and Y are as defined for Formula I.

The disclosed compounds may include 4-substituted-(4'-hydroxyphenyl)cyclohexane compounds. For example, in the disclosed compounds having Formula I, A-B may be —CH$_2$CH$_2$—, and A'-B' may be —CH$_2$CH$_2$—, and the compound may have a Formula Ib:

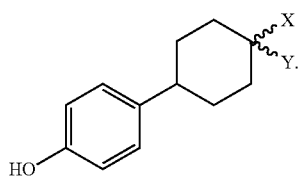

Ib where X and Y are as defined for Formula I.

In the disclosed substituted (4'-hydroxyphenyl)cycloalkane compounds, substituent Z is carbon and Y may be —CH$_2$CH$_2$—, where Y and Z form a bridge. As such, the disclosed compounds may have Formula Ic:

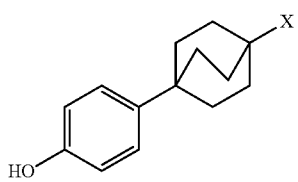

Ic where X and Y are as defined for Formula I.

The disclosed compounds may be used to prepare and formulate pharmaceutical compositions. As such, also disclosed herein are pharmaceutical compositions comprising an effective amount of any of the compounds disclosed herein, or pharmaceutically acceptable salts of any of the compounds disclosed herein, together with a pharmaceutically acceptable excipient, carrier, or diluent. In some embodiments, the disclosed compounds may be used for preparing a medicament for treating a disease or disorder associated with estrogen receptor β (ERβ) activity, and in particular, a disease or disorder that may be treated with an agonist of ERβ. As such, the disclosed compounds may exhibit ERβ agonist activity, and preferable the compounds exhibit specificity as ERβ agonists versus activity as ERβ antagonists and/or versus activity as estrogen receptor α (ERα) agonists or activity as ERα antagonists.

DETAILED DESCRIPTION

Figure 1:
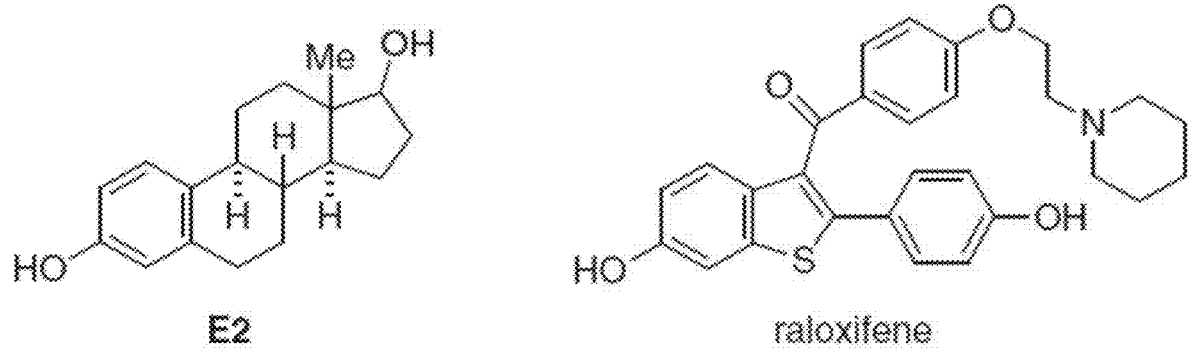
FIG. 1. Structures of 17β-estradiol and raloxifene.
Figure 2A:
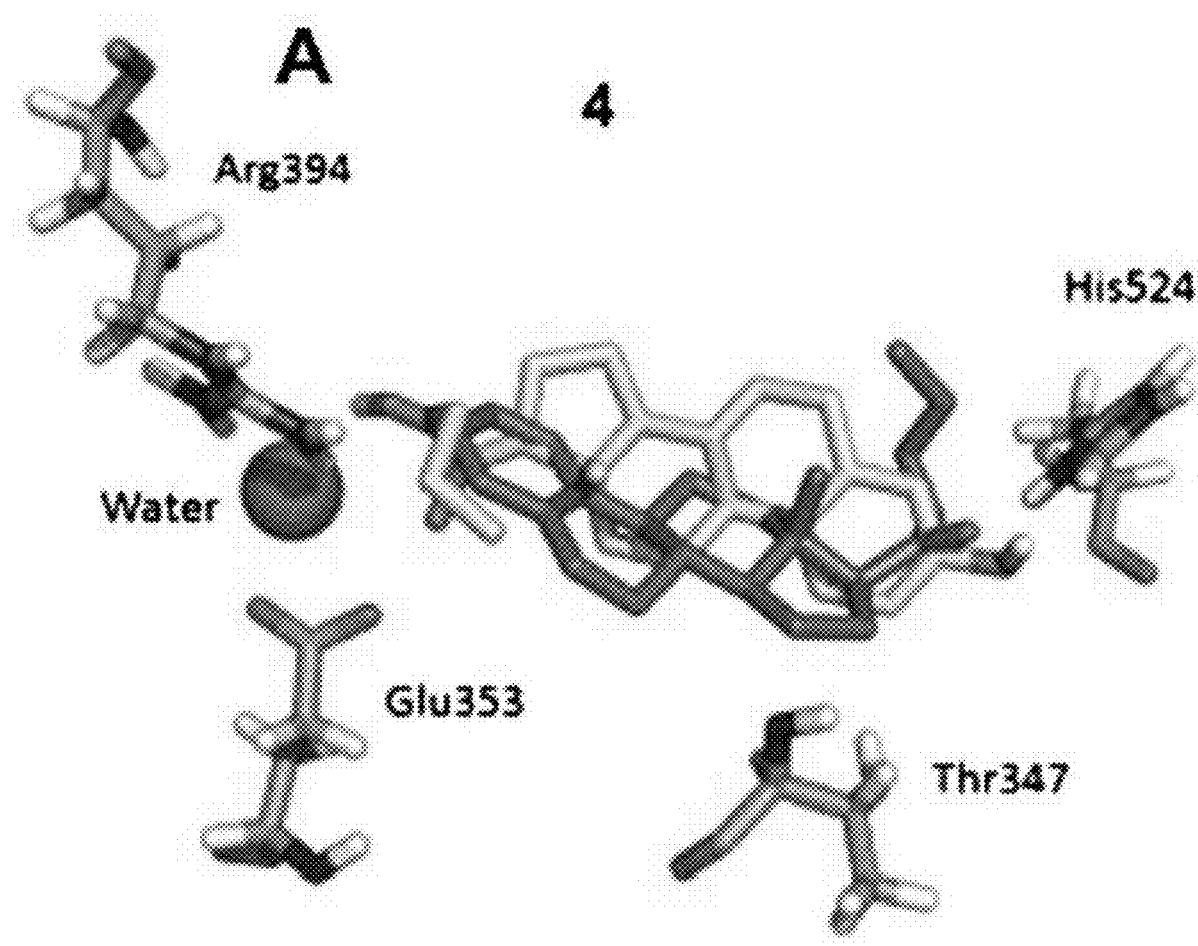
FIG. 2A and FIG. 2B. Lowest energy docking poses from clusters where ligands were predicted to bind in two modes (A-B). The human ERα estrogen receptor that was used was in the agonist conformation (PDB code 1ere; chain A).
Figure 2B:
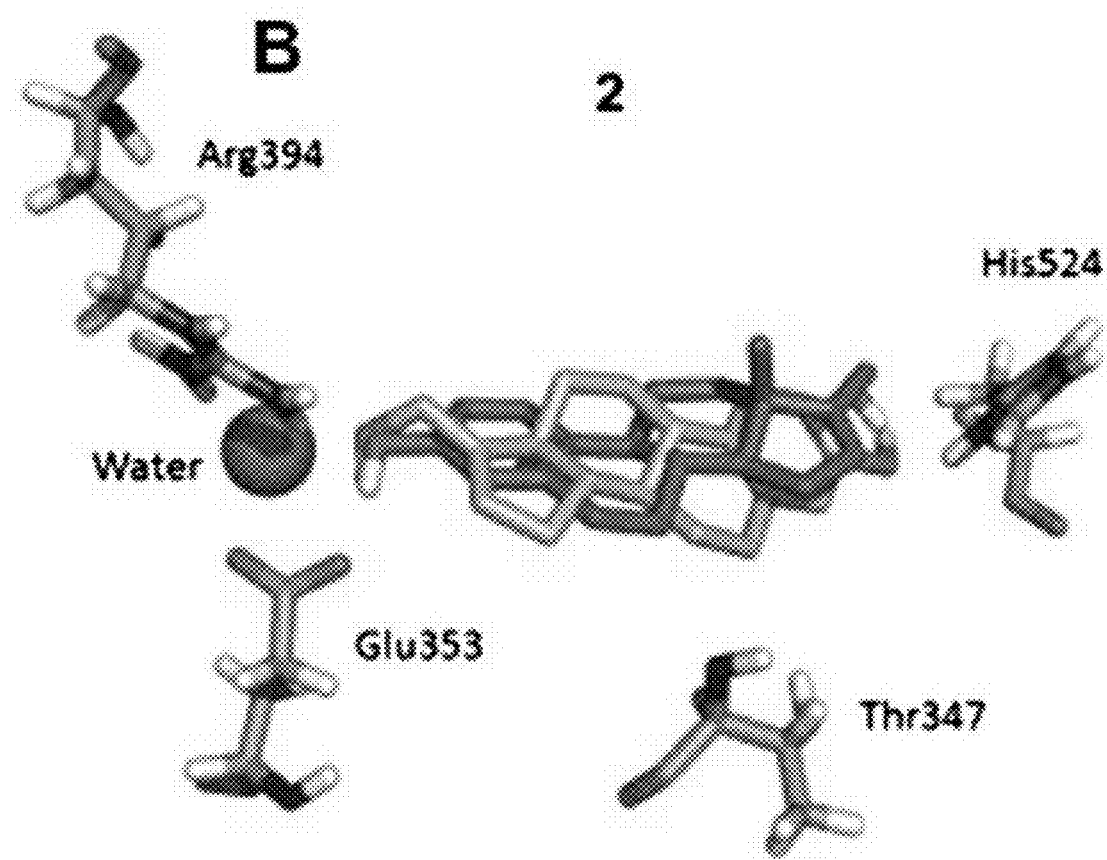
Figure 2C:
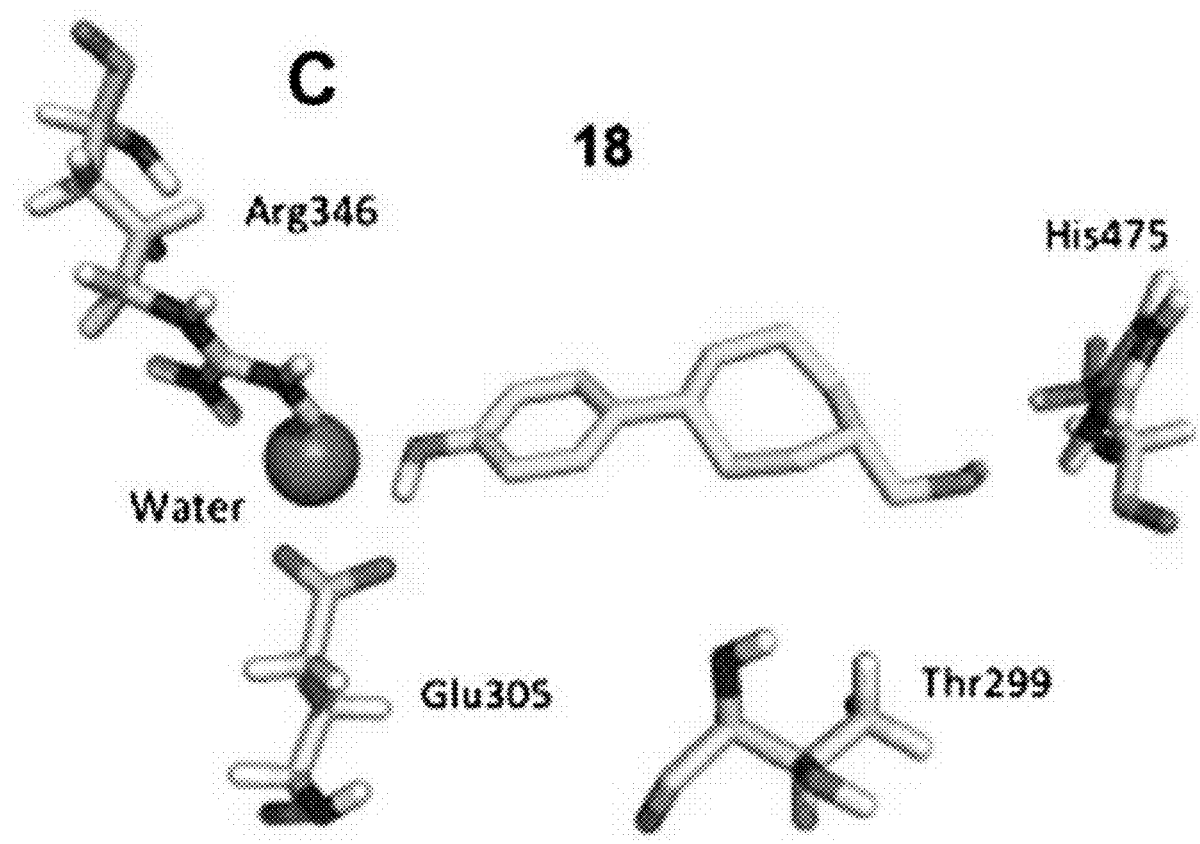
FIG. 2C shows the predicted binding orientation for 18 in ERβ, agonist conformation (PDB code 2jj3; chain A).
Figure 2D:
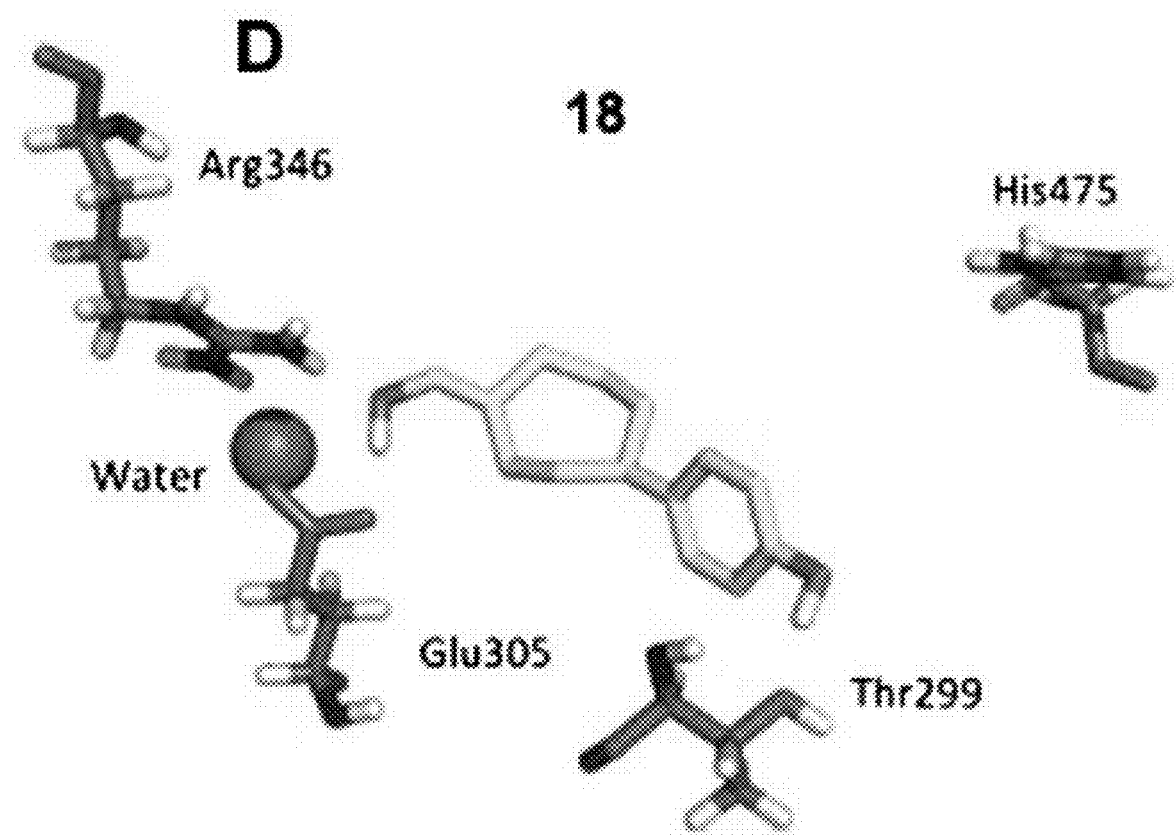
FIG. 2D shows the predicted binding orientation for 18 in ERβ, antagonist conformation (PDB code 1l2j; chain A).
Figure 3:
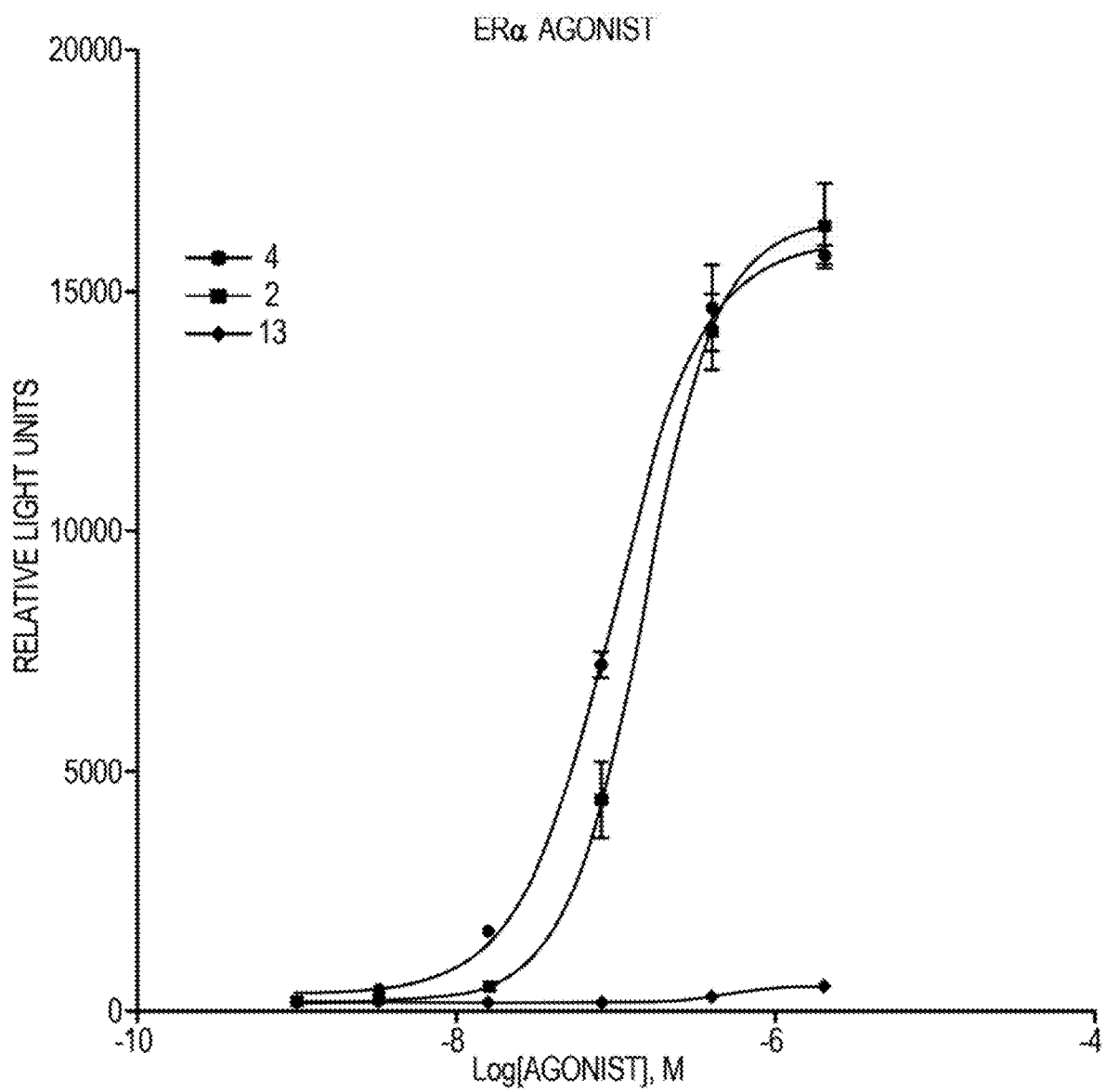
FIG. 3. Cell-based ERα assay data including regression for ligands that showed agonist activity.
Figure 4:
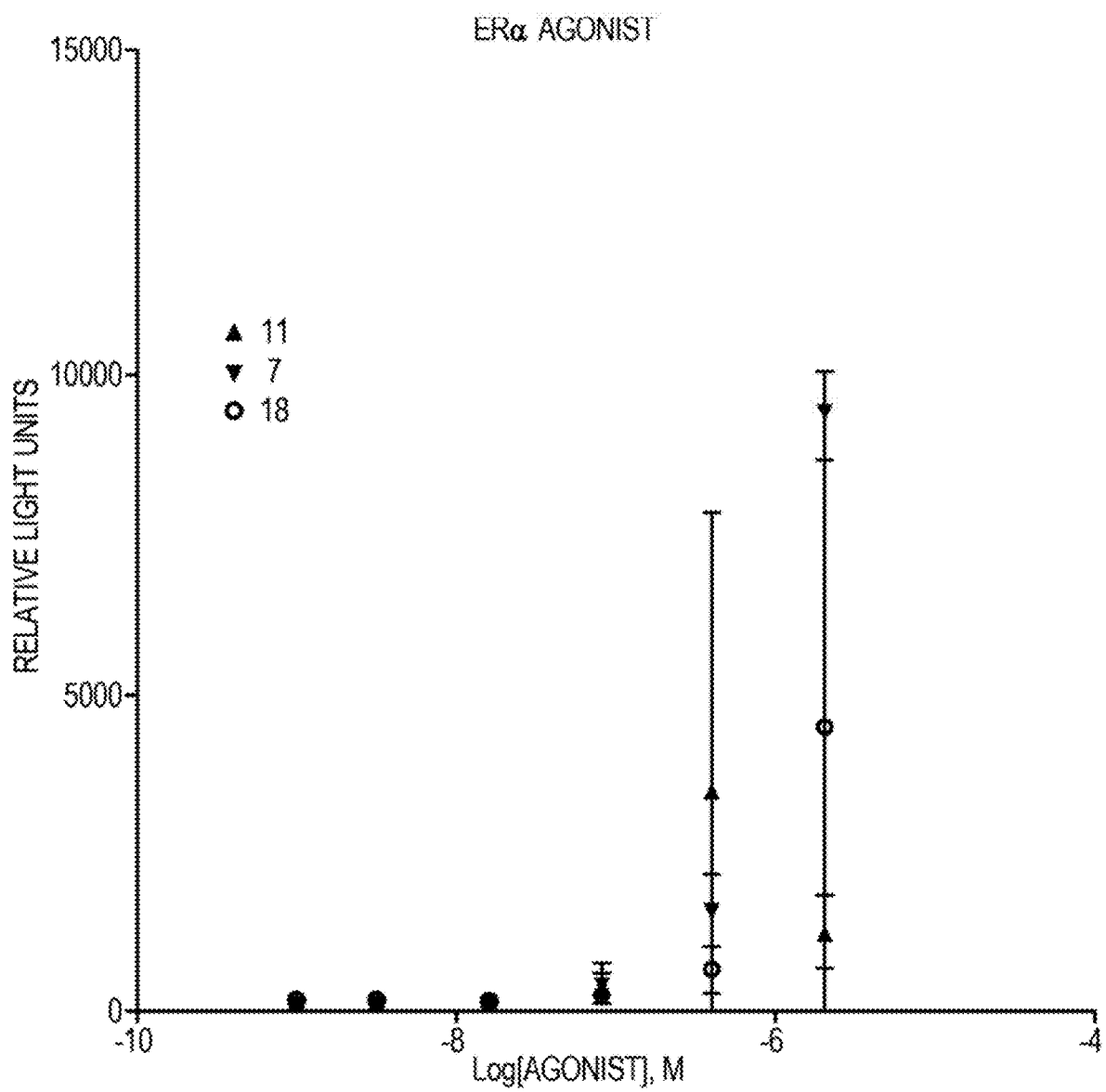
FIG. 4. Cell-based ERα agonist assay data for chemicals without sufficient quality data to determine activity.
Figure 5:
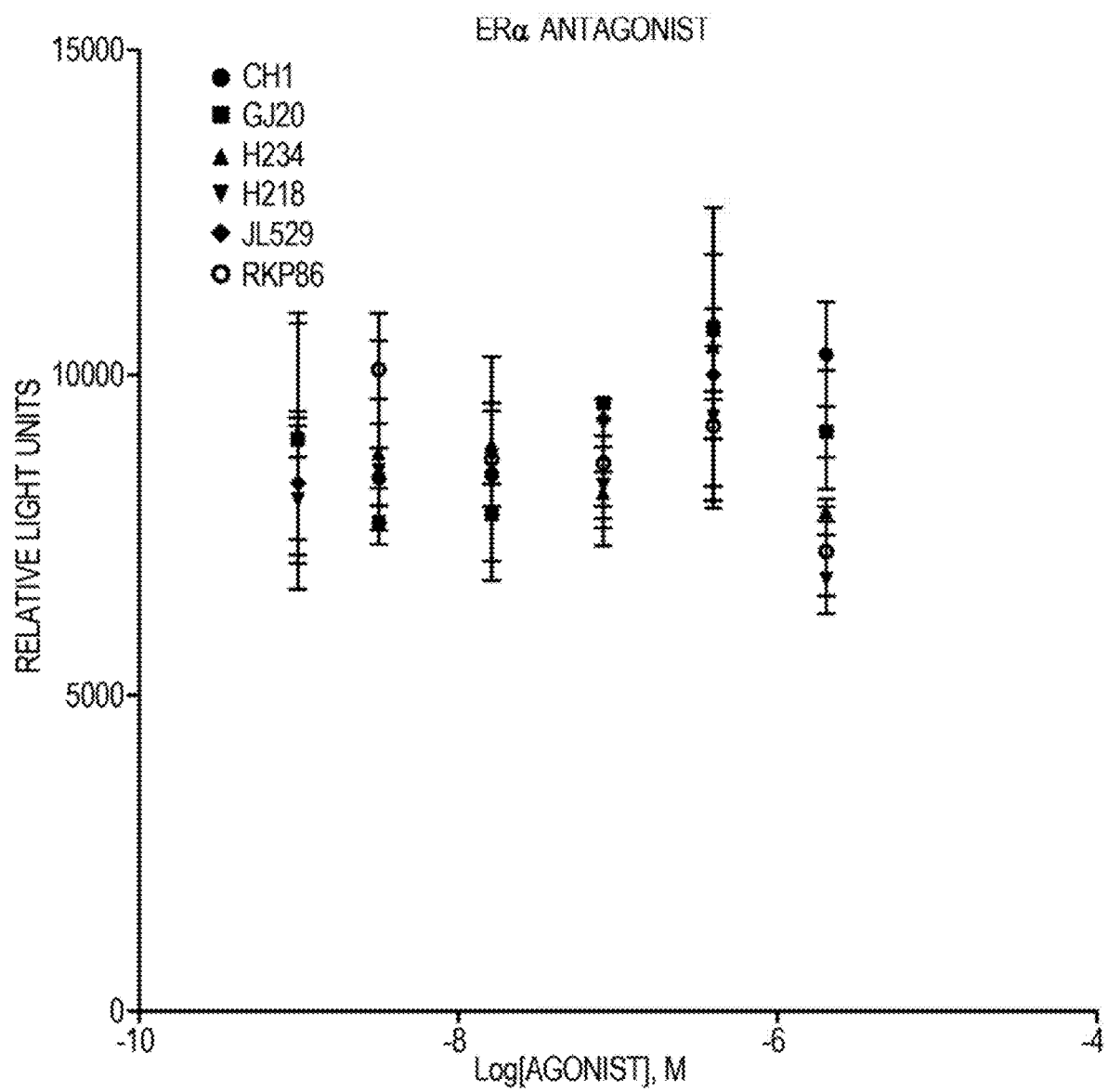
FIG. 5. Cell-based ERα antagonist assay data for chemicals without sufficient quality data to determine activity.
Figure 6:
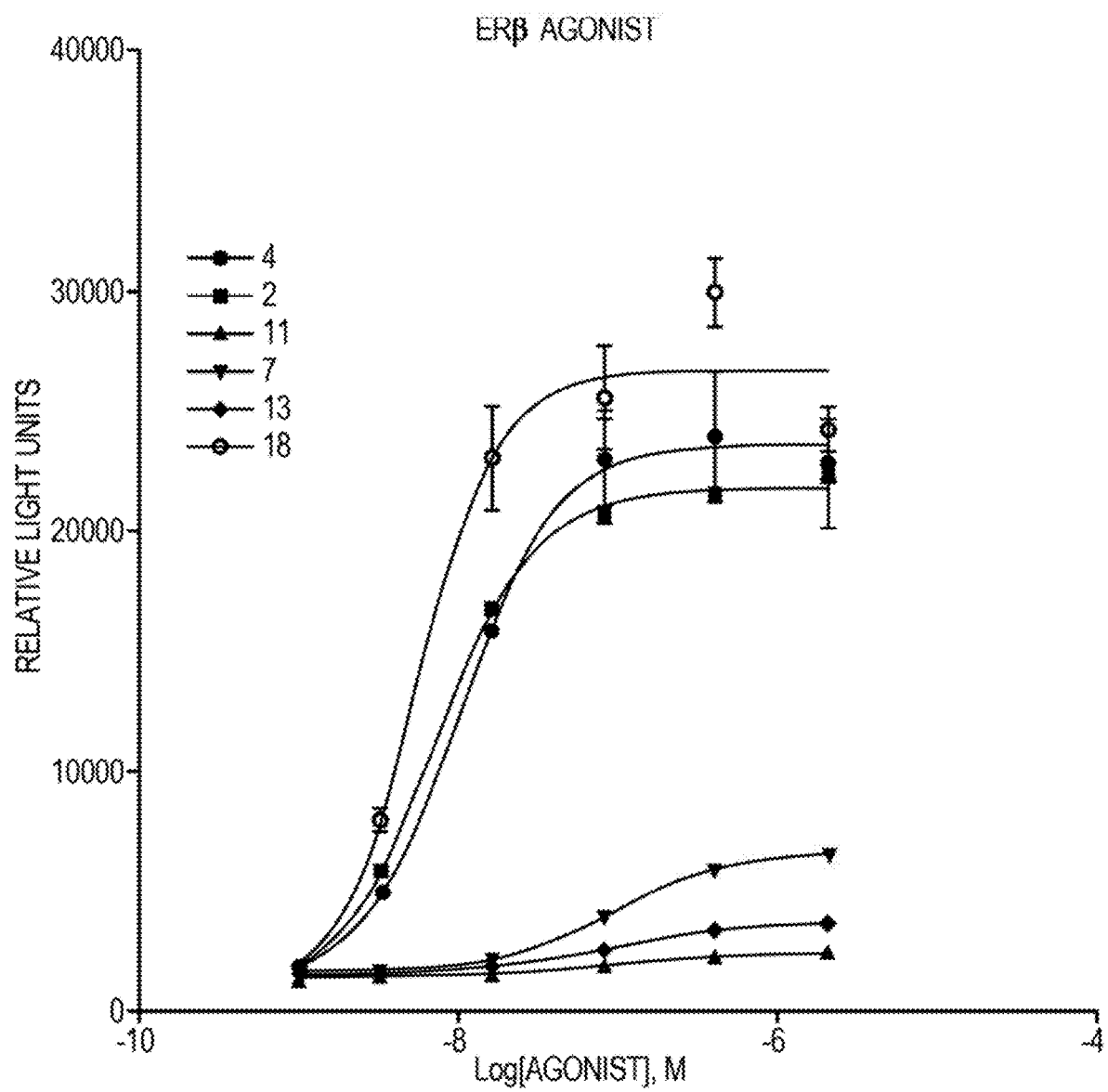
FIG. 6. Cell-based ERβ agonist assay data. for ligands that showed antagonist activity.
Figure 7:
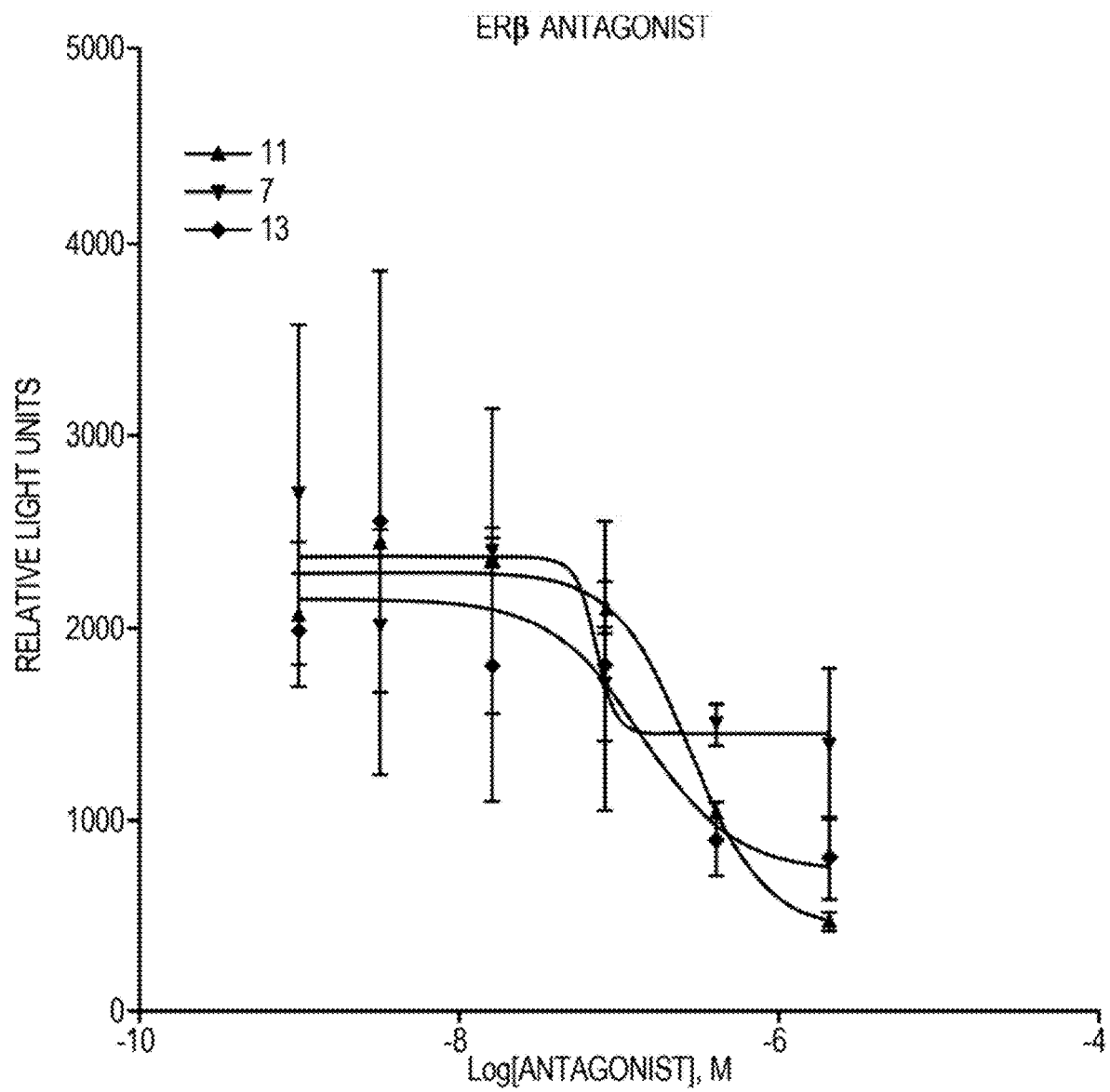
FIG. 7. Cell-based ERβ assay data for chemicals that showed antagonist activity.
Figure 8:
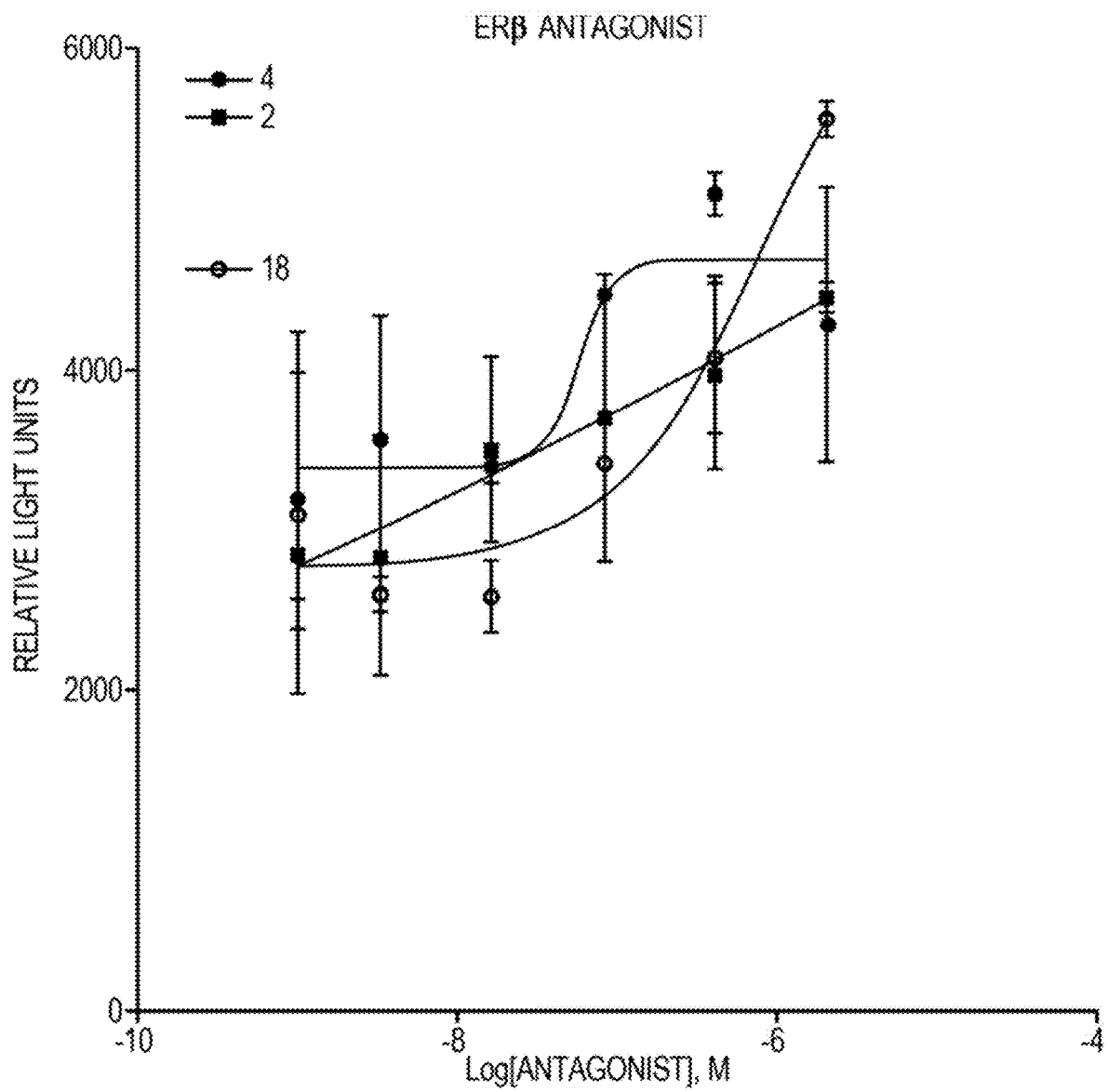
FIG. 8. Cell-based ERβ assay data for chemicals that did not display antagonist activity.
Figure 9A:
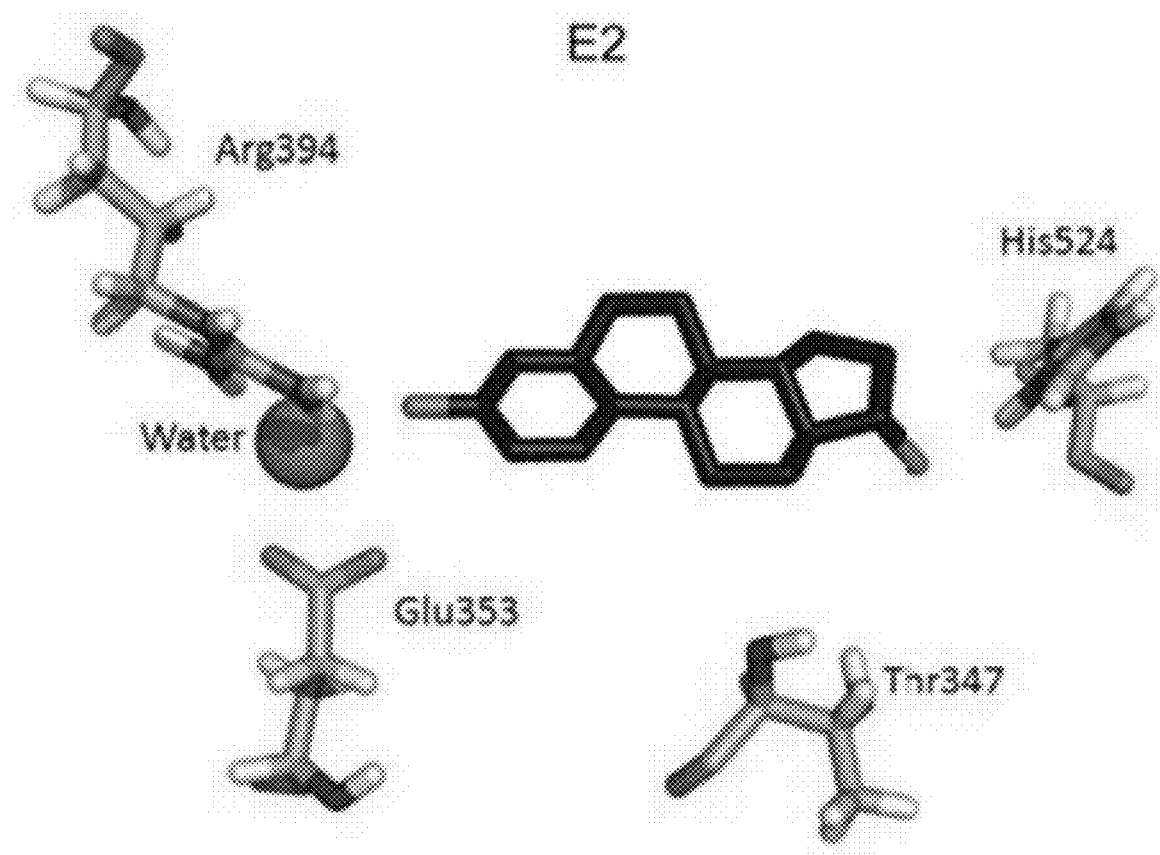
FIG. 9A, FIG. 9B, FIG. 9C, and FIG. 9D. Lowest energy docking poses for the ERα-binding compounds identified using fluorescence polarization. PDB file 1ere, chain A was used as the receptor to investigate the predicted affinity for binding in the ERα agonist conformation. E2 is estradiol and provided for comparison.
Figure 9B:
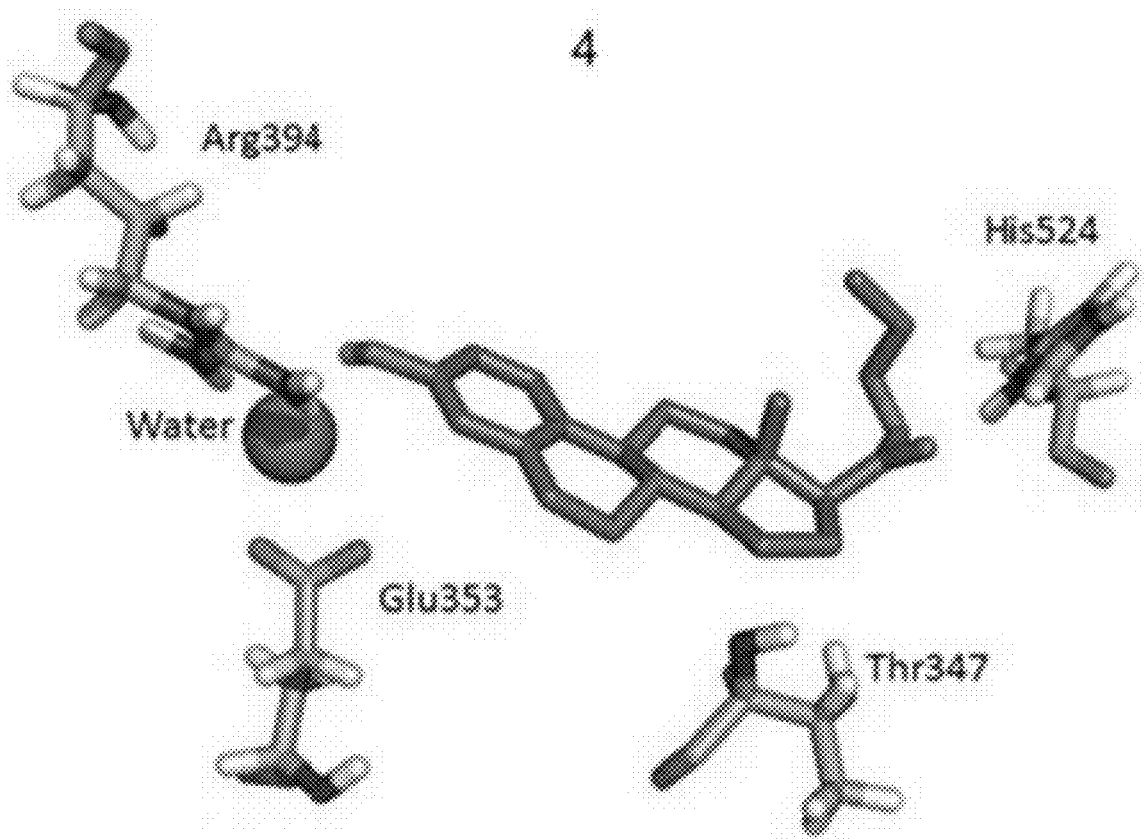
Figure 9C:
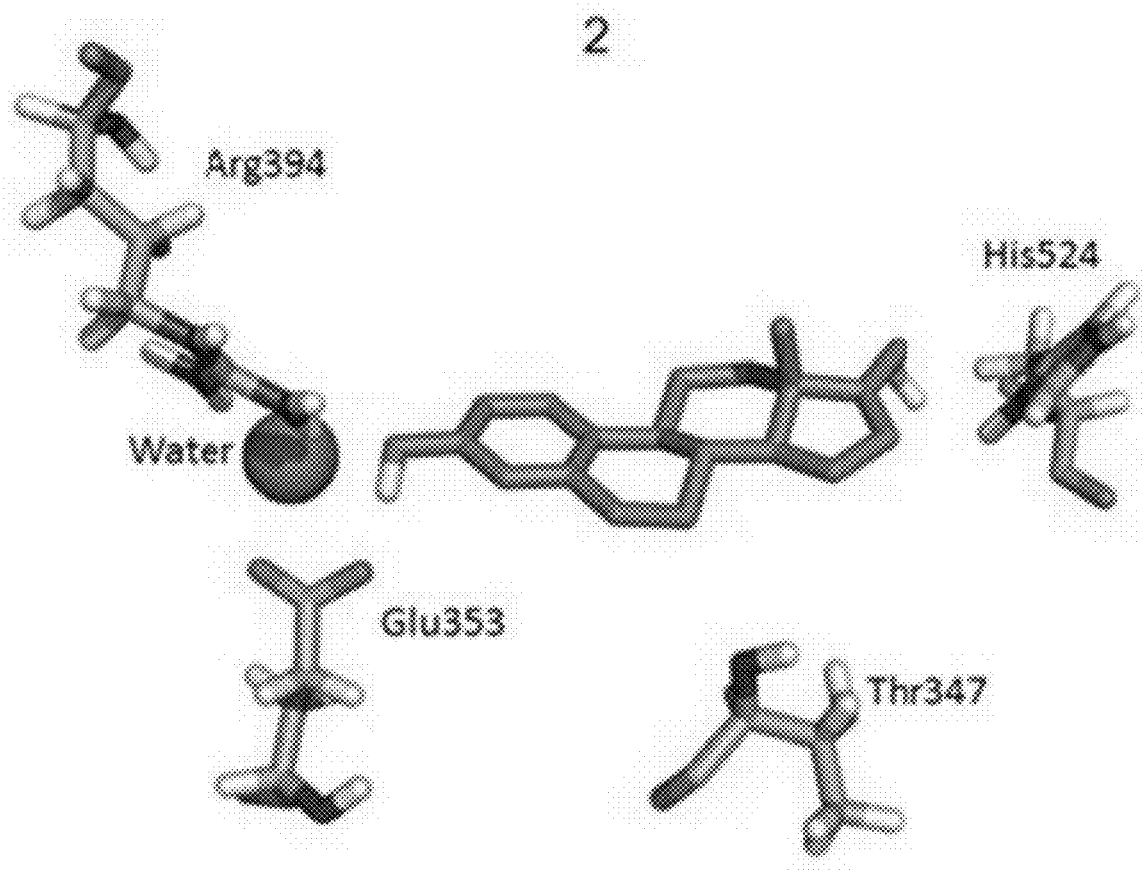
Figure 9D:
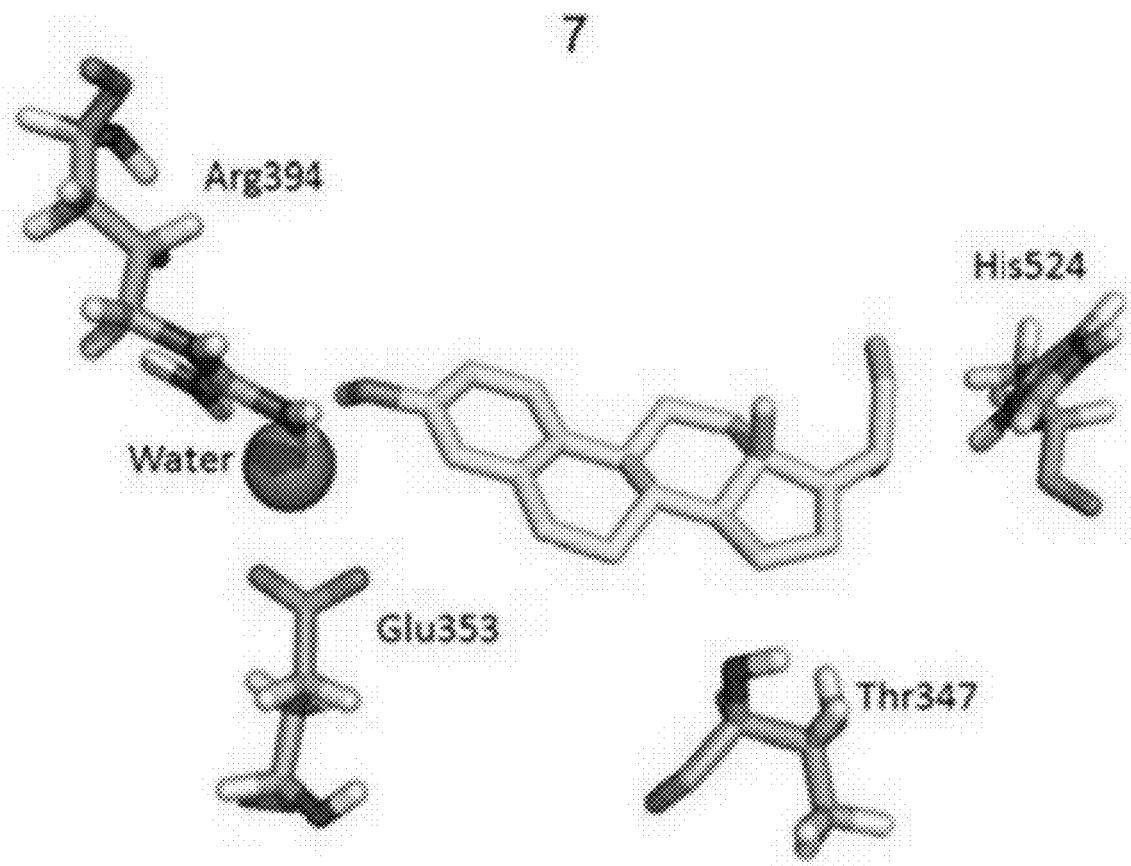
Figure 10A:
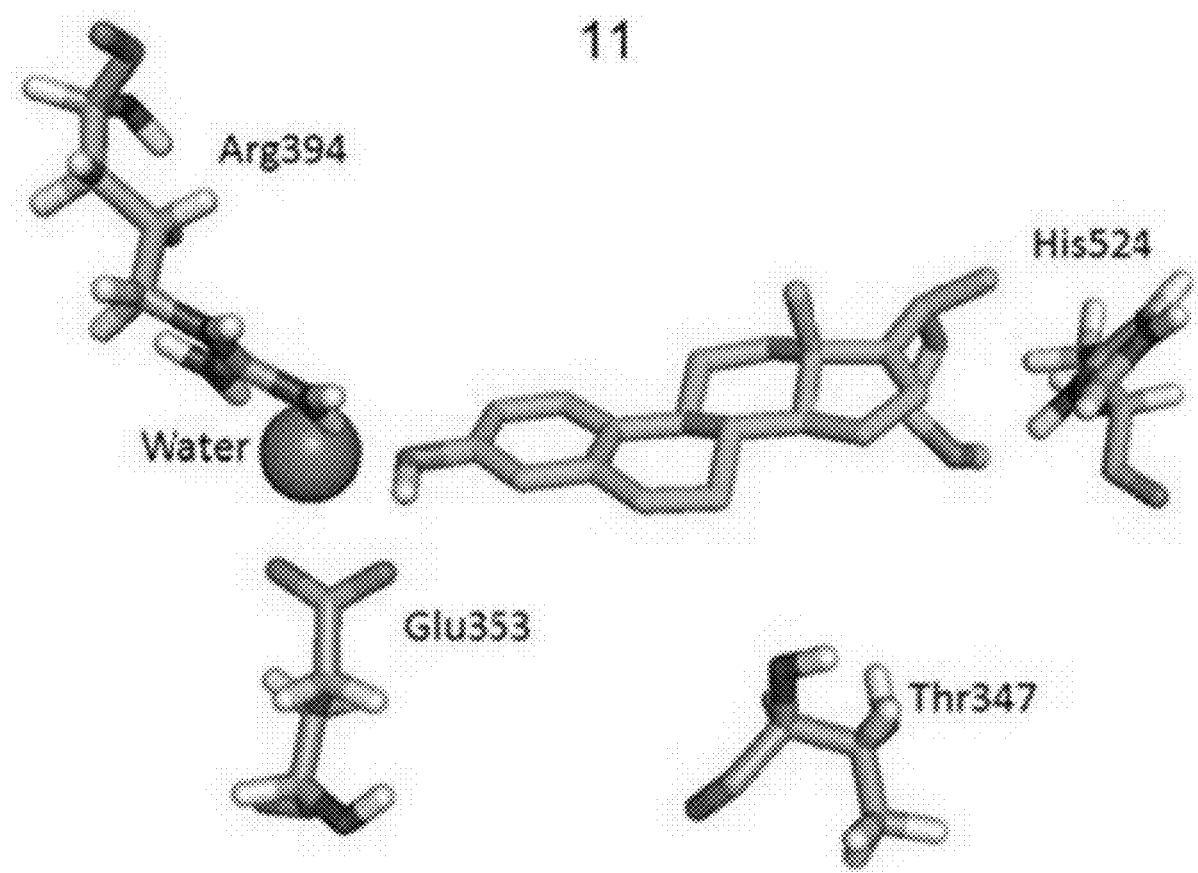
FIG. 10A, FIG. 10B, FIG. 10C, and FIG. 10D. Lowest energy docking poses for the ERα-binding compounds identified using fluorescence polarization. PDB file 1ere, chain A was used as the receptor to investigate the predicted affinity for binding in the ERα agonist conformation. Chemical 13 was docked using both enantiomers from the racemic mixture.
Figure 10B:
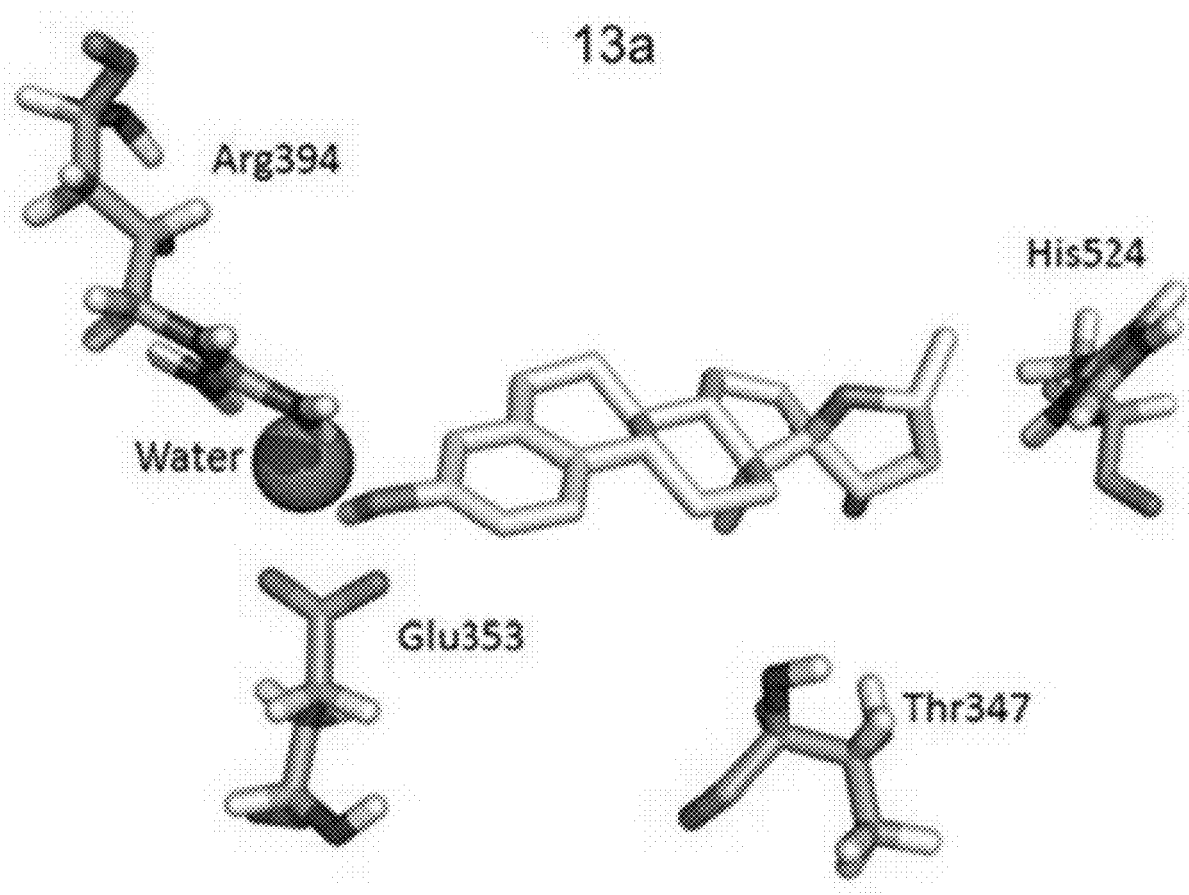
Figure 10C:
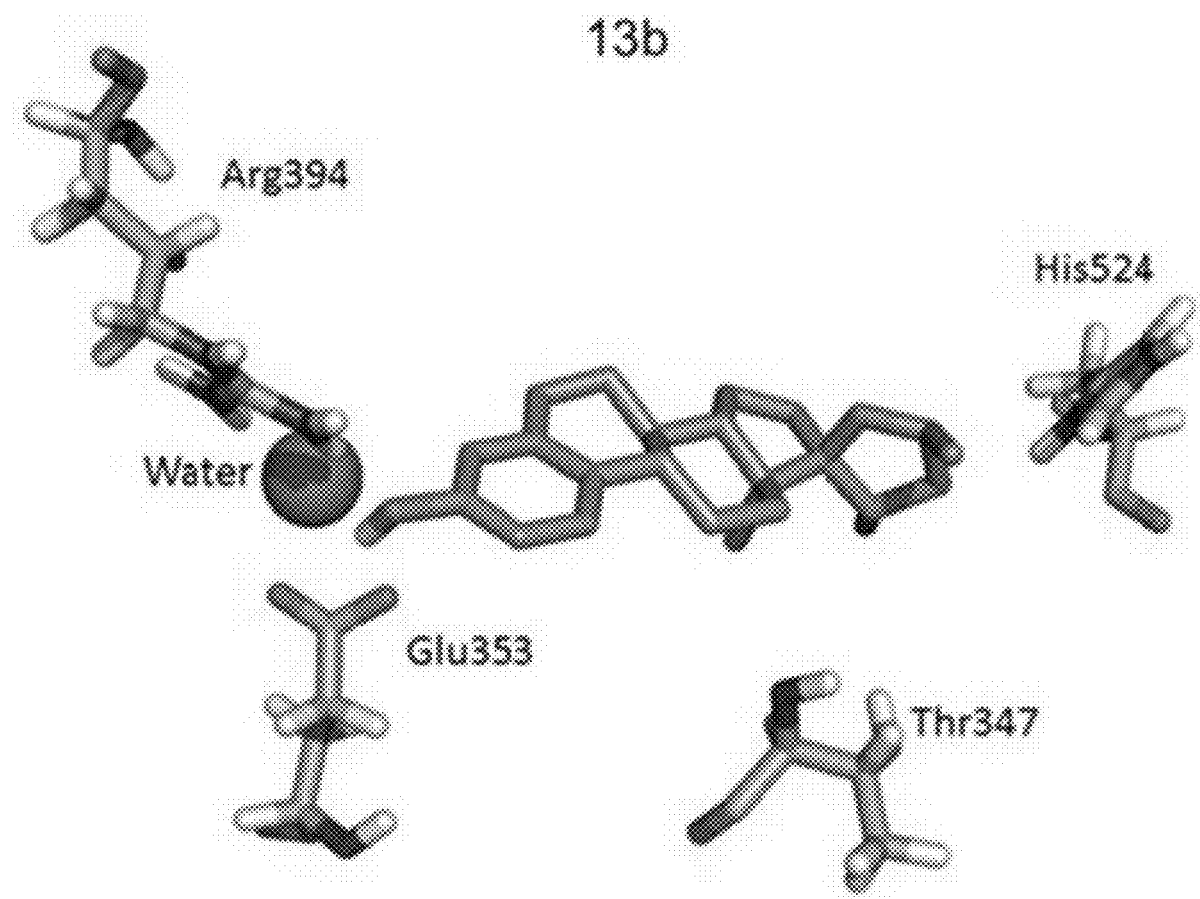
Figure 10D:
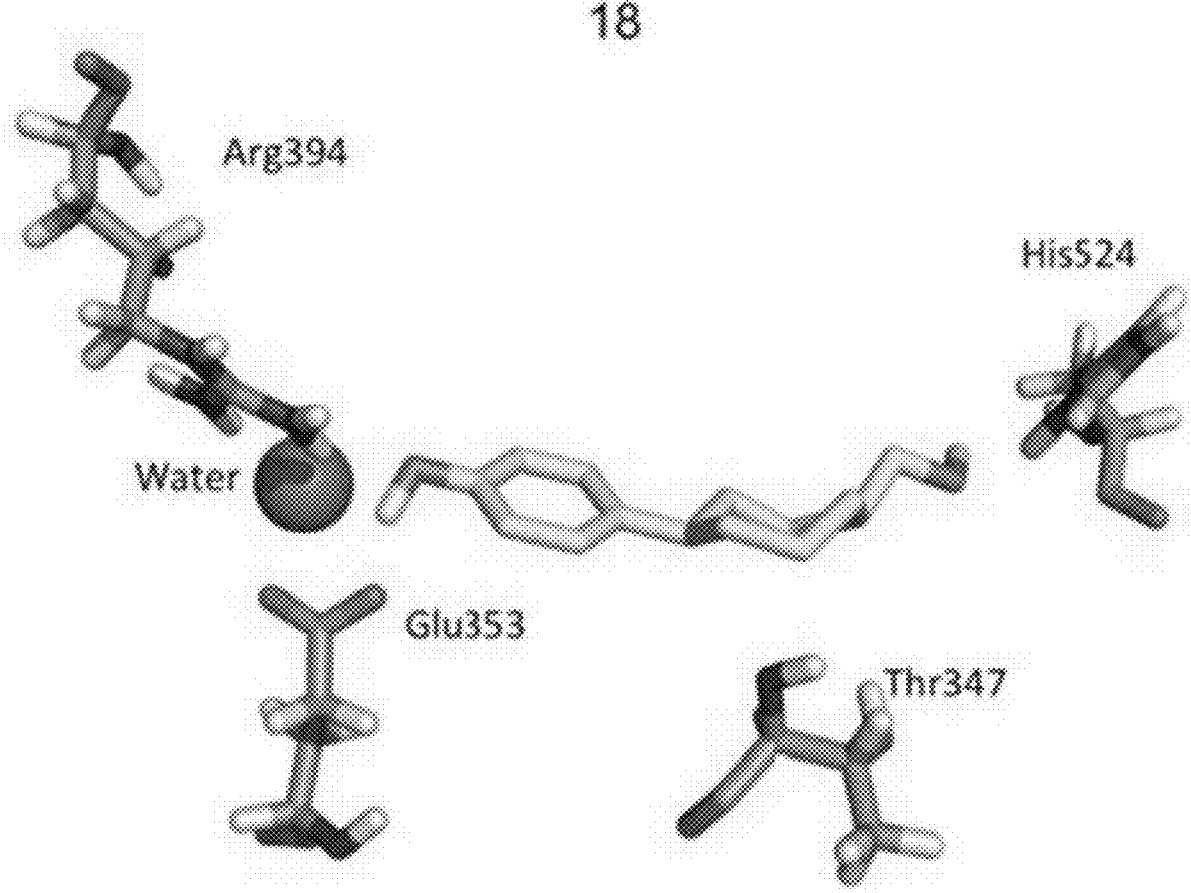
Figure 11:
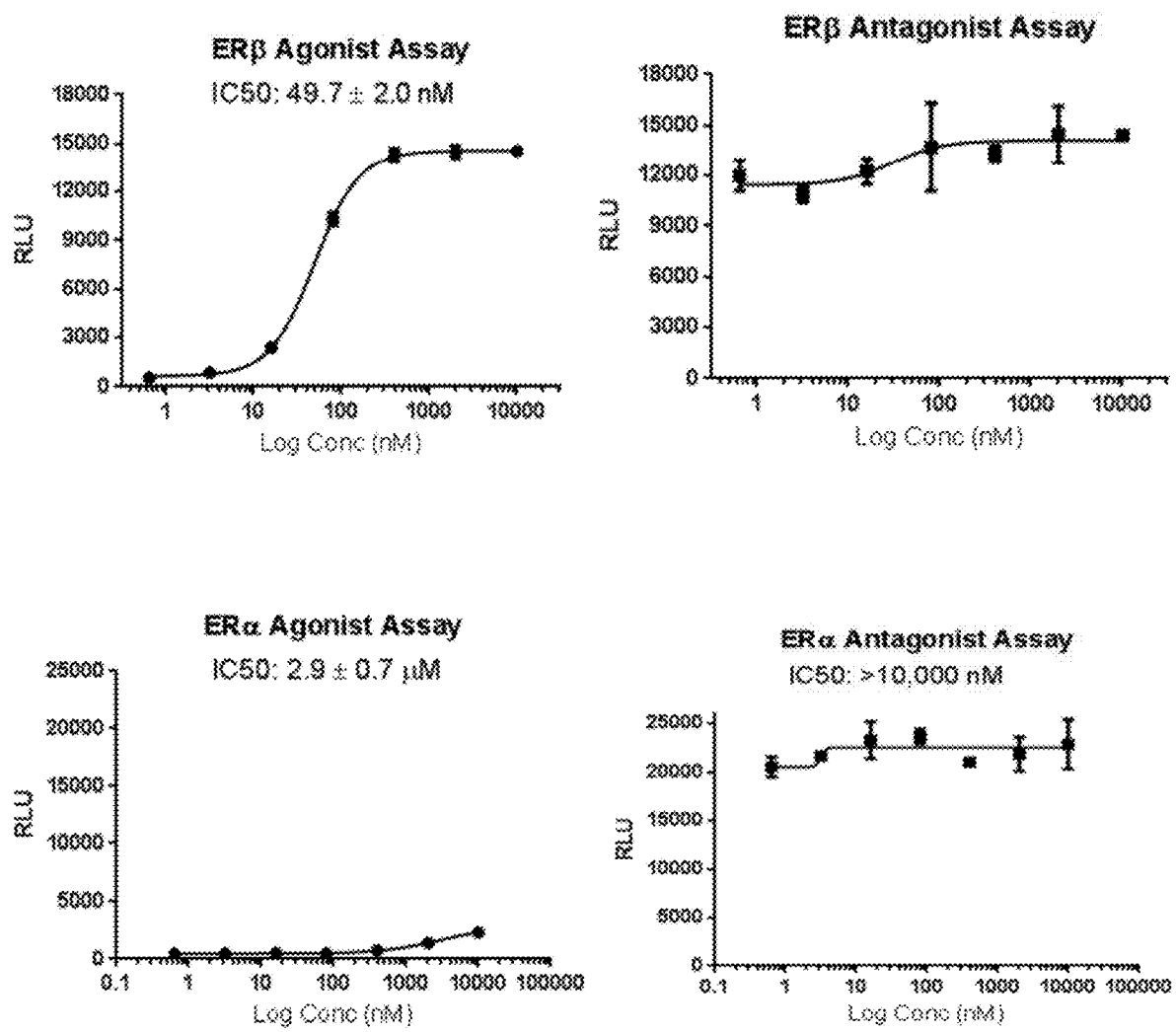
FIG. 11. Selective ERb Agonist Activity of 4-(4-Hydroxyphenyl)-1-hydroxymethylcyclohexane. The biological activity of 4-(4-Hydroxyphenyl)-1-hydroxymethylcyclohexane was tested in assays for ERβ agonist activity, ERβ antagonist activity, ERα agonist activity and ERα antagonist activity using methods disclosed herein.

The present invention is described herein using several definitions, as set forth below and throughout the application.

Unless otherwise specified or indicated by context, the terms "a", "an", and "the" mean "one or more." For example, "a substitution" should be interpreted to mean "one or more substitutions." Similarly, "a substituent group" should be interpreted to mean "one or more substituent groups."

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

Disclosed are substituted (4'-hydroxylphenyl)cycloalkane compounds and there use as selective agonists of the estrogen receptor beta isoform (ERβ). Preferred embodiments of the disclosed compounds include (4'-hydroxylphenyl)cycloheptane compounds and (4'-hydroxylphenyl)cyclohexane compounds. The disclosed compounds may alternatively be referred to as substituted 4-cycloalkylphenol compounds or p-cycloalkyl substituted phenol compounds that include one or more substitutions on the cycloalkyl substituent, which cycloalkyl substituent preferably is a cycloheptyl substituent or a cyclohexyl substituent.

In some embodiments, the disclosed compounds include one or more substitutions on the 4-carbon of the cycloalkyl substituent and have a Formula I:

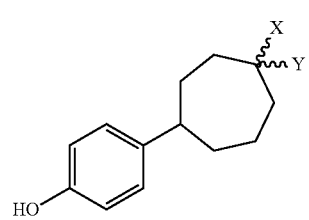

I where:
A-B is —CH₂CH₂—, —CH₂CH₂CH₂—,

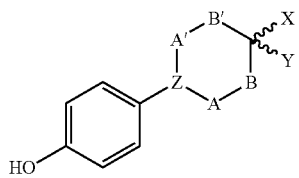

—CH₂CH=CH—, or —CH=CHCH₂—;
A'-B' is —CH₂CH₂—, or —CH=CH—;
Z is a carbon atom;
X is hydroxyl, alkyl, hydroxyalkyl (e.g., hydroxy-C(1-6)alkyl or hydroxy-C(1-3)alkyl), amino, or aminoalkyl (e.g., amino-C(1-6)alkyl or amino-C(1-3)alkyl); provided that when A-B is
—CH₂CH₂— and A'-B' is —CH₂CH₂—, then X is not hydroxyethyl and X is not aminomethyl;
Y is hydrogen, alkyl; or X and Y together form carboxyalkylidenyl (e.g., carboxy-C(1-6)alkylidenyl or carboxy-C(1-3)alkylidenyl); or X and Y together form esteralkylidenyl (e.g., (e.g., C(1-6)alkyl-ester-C(1-6)alkylidenyl or C(1-3)alkyl-ester-C(1-3)alkylidenyl); or X and Y together form hydroxyalkylidenyl (e.g., hydroxy-C(1-6)alkylidenyl or hydroxy-C(1-3)alkylidenyl); or X and Y together form aminoalkylidenyl (e.g., amino-C(1-6)alkylidenyl or amino-C(1-3)alkylidenyl); or X and Y together form oxo or oxime; or Y is —CH₂CH₂— and Y and Z form a bridge.

The disclosed compounds may include 4-substituted-(4'-hydroxyphenyl)cycloheptane compounds. For example, in the disclosed compounds having Formula I, substituent A-B may be —CH₂CH₂CH₂— and substituent A'-B' may be —CH₂CH₂- and the disclosed compounds may have a Formula Ia:

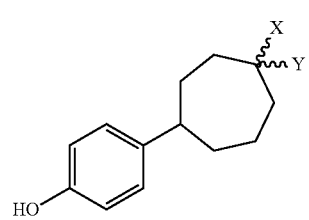

Ia where X and Y are as defined for Formula I.

In some specific embodiments of compounds having Formula Ia, the substituent X may be hydroxyl or hydroxyalkyl, and optionally Y may be hydrogen, and the compounds may have a formula selected from:

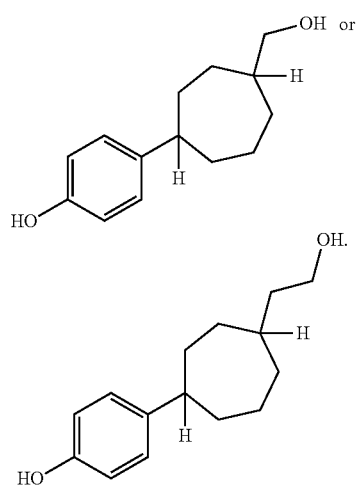

The disclosed compounds having Formula Ia may exhibit specific stereochemistry, for example, where X and Y are as defined for Formula I and the compounds have a formula selected from the group consisting of

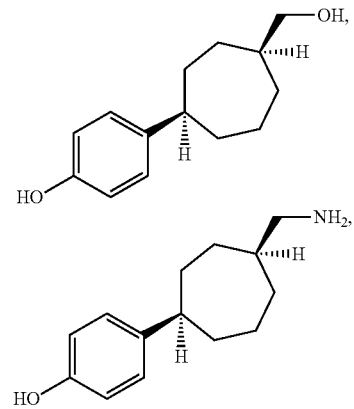

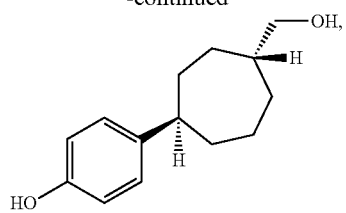

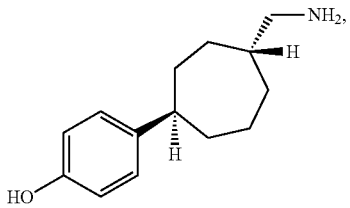

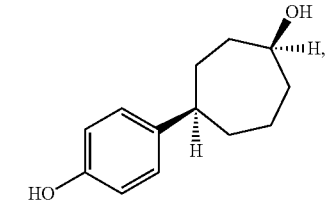

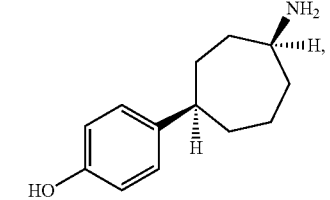

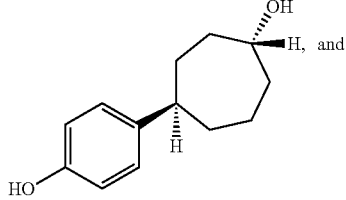

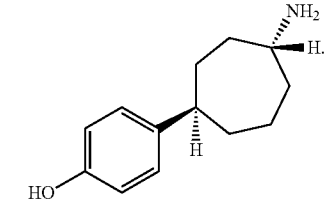

In the disclosed compounds having Formula Ia, X and Y may form an oxo group and the compounds may have a formula:

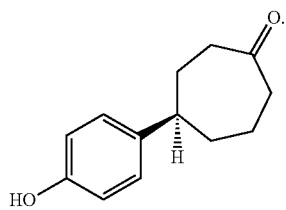 [SMILES: O=C1CCC[C@@H](c2ccc(O)cc2)CC1]

In the disclosed compounds having Formula Ia, X and Y may form alkylidene such as methylidene and the compounds may have the formula:

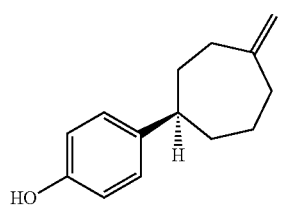

The disclosed compounds may include 4-substituted-(4'-hydroxyphenyl)cycloheptane compounds having a carboxyl substitution or a carboxyalkylester substitution on the heptane ring. In the disclosed compounds having Formula I, A-B may be

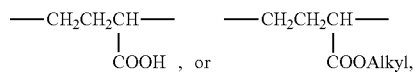

and A'-B' may be —CH$_2$CH$_2$— and the disclosed compounds may have a Formula Ia(i) or Formula Ia(ii):

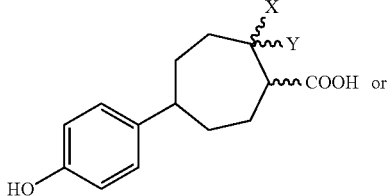

where X and Y are as defined for Formula I. In some embodiments, X and Y together may form oxo and the compounds may have a formula:

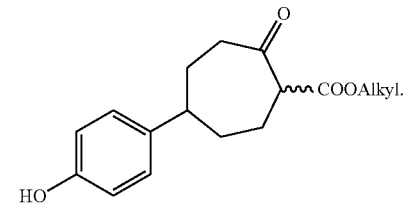

The disclosed compounds may include 4-substituted-(4'-hydroxyphenyl)cycloheptene compounds. In the disclosed compounds having Formula I, A-B may be —CH$_2$CH=CH—, and A'-B' may be —CH$_2$CH$_2$— or —CH=CH—, and the disclosed compounds may have a Formula Ia(iii), a Formula Ia(iv), or a Formula Ia(v):

Ia(iii)

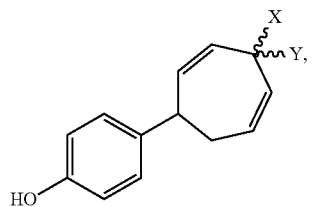

Ia(iv)

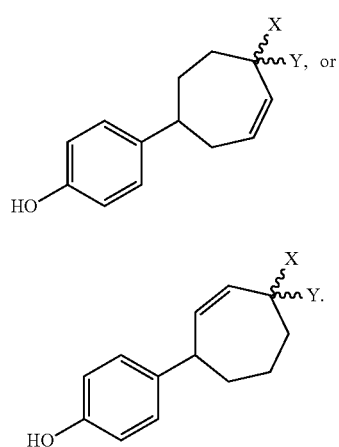

Ia(v)

where X and Y are as defined for Formula I. In some specific embodiments of compounds having Formula Ia(i), Formula Ia(ii), or Formula Ia(iii), the substituent X may be hydroxyl or hydroxyalkyl, and optionally Y may be hydrogen.

The disclosed compounds having Formula Ia(i), Formula Ia(ii), or Formula Ia(iii) may exhibit specific stereochemistry, for example, where X and Y are as defined for Formula I and the compounds have a formula selected from the group consisting of

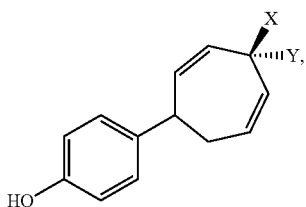

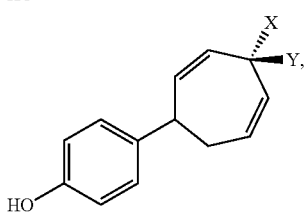

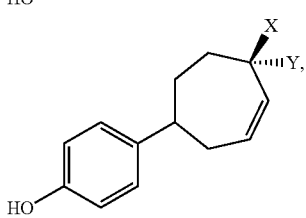

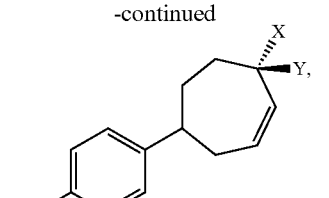

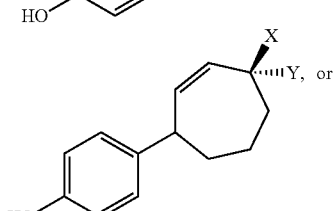

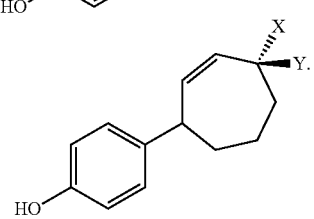

where X and Y are as defined for Formula I. In some specific embodiments, the substituent X may be hydroxyalkyl, Y may be hydrogen, and the compound may have the formula:

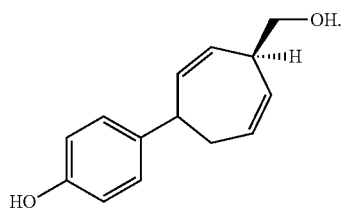 [SMILES: OC[C@H]1C=CCC(c2ccc(O)cc2)C=C1]

The disclosed compounds may include 4-substituted-(4'-hydroxyphenyl)cyclohexane compounds. For example, in the disclosed compounds having Formula I, A-B may be —CH$_2$CH$_2$—, A'-B' may be —CH$_2$CH$_2$—, and the compound may have a Formula Ib Ib

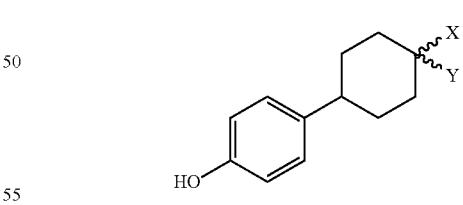

where X and Y are as defined for Formula I. In some embodiments of compounds having Formula Ib, substituent X may be hydroxymethyl and Y optionally may be hydrogen. In even further embodiments of compounds having Formula Ib, substituent X may be hydroxyalkyl and Y optionally may be alkyl.

The disclosed compounds having Formula Ib may exhibit specific stereochemistry, for example, where X and Y are as defined for Formula I and the compounds have a formula selected from the group consisting of

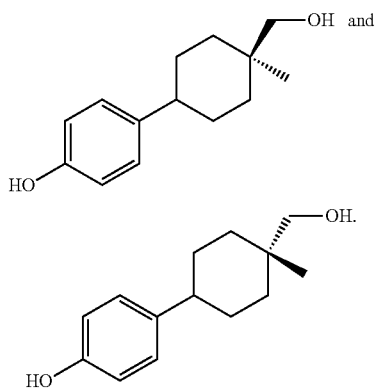

In some embodiments of compounds having Formula Ib, X may be alkyl and Y may be hydrogen and the compounds may have the formula:

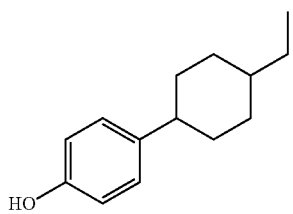

In some embodiments of compounds having Formula Ib, the substituents X and Y together may form oxo and the compounds may have the formula:

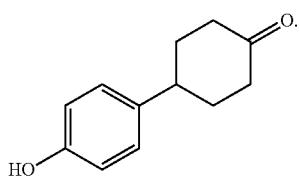 [SMILES: O=C1CCC(c2ccc(O)cc2)CC1]

In some embodiments of compounds having Formula Ib, the substituents X and Y together may form alkylidene such as methylidene and the compounds may have the formula:

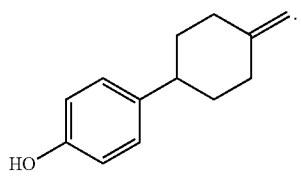

In some embodiments of compounds having Formula Ib, the substituents X and Y together may form carboxymethylidenyl, esteralkylidenyl, hydroxyethylidenyl, aminoethylidenyl, or oxime. For example, in some embodiments of the disclosed compounds having Formula Ib, X and Y together may form a alkylidenyl or an iminyl group which optionally is substituted and where the compounds have Formula Ib(i):

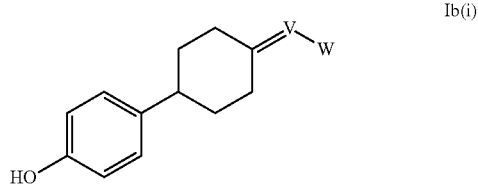

and V is carbon or nitrogen, and W is alkyl, hydroxyl, hydroxyalkyl, amino, aminoalkyl, carboxyl, alkylcarboxyl, or ester. For example, in some embodiments of the disclosed compounds having Formula Ib, X and Y together may form carboxymethylidenyl, ethylestermethylidenyl, hydroxyethylidenyl, or oxime, where the compounds have a formula selected from the following formulas, respectively.

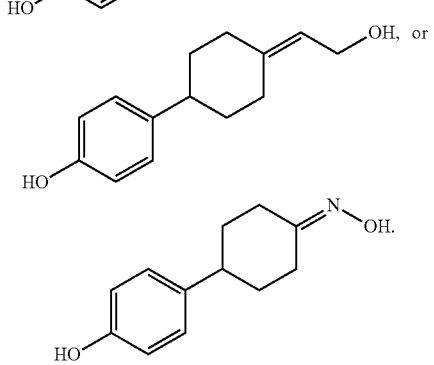

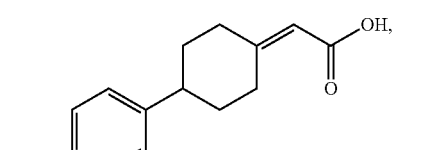

In the disclosed substituted (4'-hydroxyphenyl)cycloalkane compounds, substituent Z is carbon and Y may be —CH$_2$CH$_2$—, where Y and Z form a bridge. As such, the disclosed compounds may have Formula Ic:

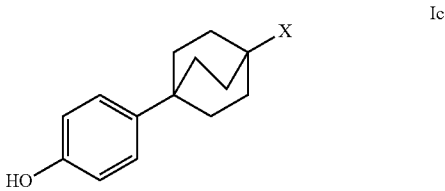

where X and Y are as defined for Formula I. Specific compounds having Formula Ic may include but are not limited to compounds having a formula selected from the group consisting of.

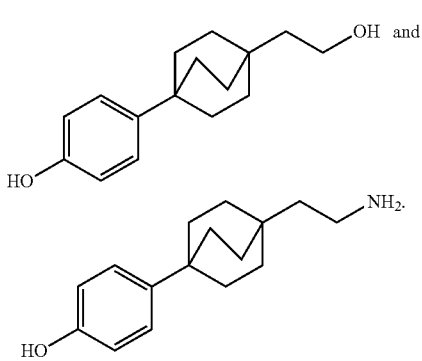

The compounds disclosed herein (e.g., compounds having any of Formula I, Ia, Ia(i), Ia(ii), Ia(iii), Ia(iv), Ia(v), Ib, Ib(i), or Ic) may have several chiral centers, and stereoisomers, epimers, and enantiomers of the disclosed compounds are contemplated. The compounds may be optically pure with respect to one or more chiral centers (e.g., some or all of the chiral centers may be completely in the S configuration; and/or some or all of the chiral centers may be completely in the R configuration; etc.). Additionally or alternatively, one or more of the chiral centers may be present as a mixture of configurations (e.g., a racemic or another mixture of the R configuration and the S configuration). Compositions comprising substantially purified stereoisomers, epimers, or enantiomers of compound having any of Formula I, la, Ia(i), Ia(ii), Ia(iii), Ib, Ib(i), or Ic are contemplated herein (e.g., a composition comprising at least about 90%, 95%, or 99% pure stereoisomer, epimer, or enantiomer.

Also disclosed herein are hydroxy-protected derivatives of the compounds disclosed herein. For example, the compounds disclosed herein (e.g., compounds having any of Formula I, la, Ia(i), Ia(ii), Ia(iii), Ia(iv), Ia(v), Ib, Ib(i), or Ic), may include a hydroxy-protected group at any hydroxy group. As contemplated herein, a "protected-hydroxy" group is a hydroxy group derivatized or protected by any of the groups commonly used for the temporary or permanent protection of hydroxy functions (e.g., alkoxycarbonyl, acyl, silyl, or alkoxyalkyl groups). A "hydroxy-protecting group" signifies any group commonly used for the temporary protection of hydroxy functions, such as for example, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. As contemplated herein, the word "alkyl" as used in the description or the claims, denotes a straight-chain or branched alkyl radical of 1 to 6 carbons, in all its isomeric forms. "Alkoxy" refers to any alkyl radical which is attached by oxygen (i.e., a group represented by "alkyl-O—"). Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group. The terms "hydroxyalkyl", "deuteroalkyl" and "fluoroalkyl" refer to an alkyl radical substituted by one or more hydroxy, deuterium, or fluoro groups respectively. An "alkylidene" refers to a radical having the general formula $C_kH_{2k}$— where K is an integer (e.g., 1-6). The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group.

The compounds disclosed herein may exhibit binding and agonist and/or antagonist activity for estrogen receptors. As used herein, "ERα" refers to estrogen receptor-alpha, and in particular, human estrogen receptor-alpha. As used herein, "ERβ" refers to estrogen receptor-beta, and in particular human estrogen receptor-beta. Agonists and antagonists for ERα and ERβ are known in the art as are assays for determining the binding affinity of a compound for ERα and ERβ and determining whether a bound compound is an agonist or antagonist for ERα and ERβ. (See e.g., McCullough et al., "Probing the human estrogen receptor-a binding requirements for phenolic mono- and di-hydroxyl compounds: a combined synthesis, binding and docking study," Biorg. & Med. Chem. (2014) Jan. 1; 22(1):303-10. doi: 10.1016/j.bmc.2013.11.024. Epub (2013) Nov. 21, and the corresponding Supplementary Information, the contents of which are incorporated herein by reference in their entireties). Suitable assays for determining the binding affinity of a compound for ERα and ERβ and determining whether a bound compound is an agonist or antagonist for ERα and ERβ may include fluorescence polarization displacement assays and cell-based ERα and ERβ luminescence activity assays.

As used herein, the term "selective agonist" may be used to refer to compounds that selectively bind to an estrogen receptor, and in particular, ERβ, relative to another estrogen receptor, and in particular ERα. For example, a compound that is a selective agonist for ERβ may have a binding affinity for ERβ receptor (e.g., as measured by $K_d$ (nM)) that is at least 3-fold greater (or at least 5-fold greater, at least 10-fold greater, at least 20-fold greater, at least 50-fold greater, at least 100-fold greater, at least 500-fold greater, or at least 1000-fold greater) than a binding affinity for ERα. Preferably, a selective agonist for ERβ has a $K_d$ (nM) for ERβ that is less than 100 nM, more preferably less than 10 nM, or even more preferably less than 1 nM; and preferably, a selective agonist for ERβ has a $K_d$ (nM) for ERα that is greater than 500 nM, more preferably greater than 1000 nM, or even more preferably greater than 2000 nM.

As used herein, the term "selective agonist" may be used to refer to compounds that selectively bind and agonize an estrogen receptor, and in particular ERβ, relative to another estrogen receptor, and in particular ERα. For example, a compound that is a selective agonist for ERβ may have an $IC_{50}$ (nM) in an assay for ERβ receptor agonist activity that is less than 100 nM, preferably less than 10 nM, even more preferably less than 1 nM; and a compound that is that is a selective agonist for ERβ may have an $IC_{50}$ (nM) in an assay for ERα receptor agonist activity that is greater than 100 nM, preferably greater than 500 nM, even more preferably greater than 1000 nM.

As used herein, the term "selective agonist" may be used to refer to compounds that selectively bind and agonize an estrogen receptor, and in particular ERβ, instead of antagonizing an estrogen receptor, and in particular ERβ. For example, a compound that is a selective agonist for ERβ may have an $IC_{50}$ (nM) in an assay for ERβ receptor agonist activity that is less than 100 nM, preferably less than 10 nM, even more preferably less than 1 nM; and a compound that is that is a selective agonist for ERβ may have an $IC_{50}$ (nM)

in an assay for ERβ receptor antagonist activity that is greater than 100 nM, preferably greater than 500 nM, even more preferably greater than 1000 nM.

Pharmaceutically acceptable salts of the disclosed compounds also are contemplated herein and may be utilized in the disclosed treatment methods. For example, a substituent group of the disclosed compounds may be protonated or deprotonated and may be present together with an anion or cation, respectively, as a pharmaceutically acceptable salt of the compound. The term "pharmaceutically acceptable salt" as used herein, refers to salts of the compounds which are substantially non-toxic to living organisms. Typical pharmaceutically acceptable salts include those salts prepared by reaction of the compounds as disclosed herein with a pharmaceutically acceptable mineral or organic acid or an organic or inorganic base. Such salts are known as acid addition and base addition salts. It will be appreciated by the skilled reader that most or all of the compounds as disclosed herein are capable of forming salts and that the salt forms of pharmaceuticals are commonly used, often because they are more readily crystallized and purified than are the free acids or bases.

Acids commonly employed to form acid addition salts may include inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of suitable pharmaceutically acceptable salts may include the sulfate, pyrosulfate, bisulfate, sulfite, bisulfate, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleat-, butyne-.1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, alpha-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Bases useful in preparing such salts include sodium hydroxide, potassium hydroxide, ammonium hydroxide, potassium carbonate, sodium carbonate, sodium bicarbonate, potassium bicarbonate, calcium hydroxide, calcium carbonate, and the like.

It should be recognized that the particular counter-ion forming a part of any salt of a compound disclosed herein is usually not of a critical nature, so long as the salt as a whole is pharmacologically acceptable and as long as the counterion does not contribute undesired qualities to the salt as a whole. Undesired qualities may include undesirably solubility or toxicity.

It will be further appreciated that the disclosed compounds can be in equilibrium with various inner salts. For example, inner salts include salts wherein the compound includes a deprotonated substituent group and a protonated substituent group.

The disclosed compounds may be used to prepare and formulate pharmaceutical compositions. As such, also disclosed herein are pharmaceutical compositions comprising an effective amount of any of the compounds disclosed herein, or pharmaceutically acceptable salts of any of the compounds disclosed herein, together with a pharmaceutical excipient. In some embodiments, the disclosed compounds may be used for preparing a medicament for treating a disease or disorder associated with estrogen receptor β (ERβ) activity, and in particular, a disease or disorder that may be treated with a specific agonist of ERβ. As such, the disclosed compounds may exhibit ERβ agonist activity, and preferable the compounds exhibit specificity as an ERβ agonist versus an ERβ antagonist, an ERα agonist, and/or an ERα antagonist.

The disclosed compounds may be used to prepare and formulate pharmaceutical compositions for treating diseases that are associated with estrogen ERβ activity. Diseases and disorders associated with ERβ activity may include, but are not limited to, cell proliferative diseases and disorders (e.g., breast cancer, ovarian cancer, and endometrial cancer), psychiatric diseases and disorders (e.g., depression or anxiety), neurodegenerative diseases or disorders, bone metabolic diseases or disorders (e.g. osteoporosis), metabolic diseases or disorders (e.g., obesity or insulin resistance), and cardiovascular diseases or disorders. The disclosed pharmaceutical compositions may be administered to patients in need thereof in methods for treating diseases and disorders associated with ERβ activity.

The compounds and pharmaceutical compositions disclosed herein may be administered to a patient in need thereof to treat a disease or disorder. In some embodiments, the compounds disclosed herein may be administered at an effective concentration such that the compound functions as an agonist for ERβ in order to treat a disease or disorder associated with ERβ activity. In some embodiments, the amount of the disclosed compounds that is effective for the compound to function as an agonist of ERβ is about 0.05-50 μM (or about 0.05-10 μM, or about 0.05-1 μM).

As used herein, a "patient" may be interchangeable with "subject" or "individual" and means an animal, which may be a human or non-human animal, in need of treatment. Suitable patients for the disclosed methods may include, for example mammals, such as humans, monkeys, dogs, cats, horses, rats, and mice. Suitable human patient include, for example, those who have a disease or disorder associated with ERβ activity or those who have been determined to be at risk for developing a disease or disorder associated with ERβ activity.

As used herein, a "patient in need of treatment" may include a patient having a disease, disorder, or condition that is responsive to therapy with an ERβ agonist. For example, a "patient in need of treatment" may include a patient having a cell proliferative disease, disorder, or condition such as cancer (e.g., cancers such as breast cancer). In addition, a "patient in need of treatment" may include a patient having a psychiatric disease or disorder (e.g., depression or anxiety).

As used herein, the terms "treating" or "to treat" each mean to alleviate symptoms, eliminate the causation of resultant symptoms either on a temporary or permanent basis, and/or to prevent or slow the appearance or to reverse the progression or severity of resultant symptoms of the named disorder. As such, the methods disclosed herein encompass both therapeutic and prophylactic administration.

As used herein the term "effective amount" refers to the amount or dose of the compound, upon single or multiple dose administration to the subject, which provides the desired effect in the subject under diagnosis or treatment. The disclosed methods may include administering an effective amount of the disclosed compounds (e.g., as present in a pharmaceutical composition) for treating a disease or disorder associated with ERβ activity in a patient, whereby the effective amount induces, promotes, or causes ERβ agonist activity in the patient.

An effective amount can be readily determined by the attending diagnostician, as one skilled in the art, by the use of known techniques and by observing results obtained under analogous circumstances. In determining the effective amount or dose of compound administered, a number of factors can be considered by the attending diagnostician, such as: the species of the subject; its size, age, and general health; the degree of involvement or the severity of the disease or disorder involved; the response of the individual patient; the particular compound administered; the mode of administration; the bioavailability characteristics of the preparation administered; the dose regimen selected; the use of concomitant medication; and other relevant circumstances.

In some embodiments, a daily dose of the disclosed compounds may contain from about 0.01 mg/kg to about 100 mg/kg (such as from about 0.05 mg/kg to about 50 mg/kg and/or from about 0.1 mg/kg to about 25 mg/kg) of each compound used in the present method of treatment. The dose may be administered under any suitable regimen (e.g., weekly, daily, twice daily).

The pharmaceutical compositions for use according to the methods as disclosed herein may include be a single compound as an active ingredient or a combination of compounds as active ingredients. For example, the methods disclosed herein may be practiced using a composition containing a single compound that is an ERβ agonist. Alternatively, the disclosed methods may be practiced using a composition containing two or more compounds that are ERβ agonists, or a compound that is an ERβ agonist together with a compound that is an ERα antagonist.

Instead of administering a pharmaceutical composition comprising a compound that is an ERβ agonist together with a compound that is an ERα antagonist, the disclosed methods may be practiced by administering a first pharmaceutical composition (e.g., a pharmaceutical composition comprising an ERβ agonist) and administering a second pharmaceutical composition (e.g., a pharmaceutical composition comprising an ERα antagonist), where the first composition may be administered before, concurrently with, or after the second composition. As such, the first pharmaceutical composition and the second pharmaceutical composition may be administered concurrently or in any order, irrespective of their names.

As one skilled in the art will also appreciate, the disclosed pharmaceutical compositions can be prepared with materials (e.g., actives excipients, carriers, and diluents etc.) having properties (e.g., purity) that render the formulation suitable for administration to humans. Alternatively, the formulation can be prepared with materials having purity and/or other properties that render the formulation suitable for administration to non-human subjects, but not suitable for administration to humans.

The compounds utilized in the methods disclosed herein may be formulated as a pharmaceutical composition in solid dosage form, although any pharmaceutically acceptable dosage form can be utilized. Exemplary solid dosage forms include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof. Alternatively, the compounds utilized in the methods disclosed herein may be formulated as a pharmaceutical composition in liquid form (e.g., an injectable liquid or gel)

The compounds utilized in the methods disclosed herein may be formulated as a pharmaceutical composition that includes an excipient, carrier, or diluent. For example, the excipient, carrier, or diluent may be selected from the group consisting of proteins, carbohydrates, sugar, talc, magnesium stearate, cellulose, calcium carbonate, and starch-gelatin paste.

The compounds utilized in the methods disclosed herein also may be formulated as a pharmaceutical composition that includes one or more binding agents, filling agents, lubricating agents, suspending agents, sweeteners, flavoring agents, preservatives, buffers, wetting agents, disintegrants, and effervescent agents. Filling agents may include lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (Pro-Solv SMCC™). Suitable lubricants, including agents that act on the flowability of the powder to be compressed, may include colloidal silicon dioxide, such as Aerosil®200, talc, stearic acid, magnesium stearate, calcium stearate, and silica gel. Examples of sweeteners may include any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like. Examples of preservatives may include potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride.

Suitable diluents for the pharmaceutical compositions may include pharmaceutically acceptable inert fillers, such as microcrystalline cellulose, lactose, dibasic calcium phosphate, saccharides, and mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

The disclosed pharmaceutical compositions also may include disintegrants. Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

The disclosed pharmaceutical compositions also may include effervescent agents. Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

Pharmaceutical compositions comprising the compounds may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis.

Pharmaceutical compositions adapted for topical administration may be formulated as ointments, creams, suspensions, lotions, powders, solutions, pastes, gels, impregnated dressings, sprays, aerosols or oils and may contain appropriate conventional additives such as preservatives, solvents to assist drug penetration and emollients in ointments and creams.

For applications to the eye or other external tissues, for example the mouth and skin, the pharmaceutical compositions are preferably applied as a topical ointment or cream. When formulated in an ointment, the compound may be employed with either a paraffinic or a water-miscible ointment base. Alternatively, the compound may be formulated in a cream with an oil-in-water cream base or a water-in-oil base. Pharmaceutical compositions adapted for topical administration to the eye include eye drops where the active ingredient is dissolved or suspended in a suitable carrier, especially an aqueous solvent.

Pharmaceutical compositions adapted for topical administration in the mouth include lozenges, pastilles and mouth washes.

Pharmaceutical compositions adapted for rectal administration may be presented as suppositories or enemas.

Pharmaceutical compositions adapted for nasal administration where the carrier is a solid include a coarse powder having a particle size (e.g., in the range 20 to 500 microns) which is administered in the manner in which snuff is taken (i.e., by rapid inhalation through the nasal passage from a container of the powder held close up to the nose). Suitable formulations where the carrier is a liquid, for administration as a nasal spray or as nasal drops, include aqueous or oil solutions of the active ingredient.

Pharmaceutical compositions adapted for administration by inhalation include fine particle dusts or mists which may be generated by means of various types of metered dose pressurized aerosols, nebulizers or insufflators.

Pharmaceutical compositions adapted for vaginal administration may be presented as pessaries, tampons, creams, gels, pastes, foams or spray formulations.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

EXAMPLES

The following examples are illustrative and should not be interpreted to limit the claimed subject matter.

Example 1. Probing the Human Estrogen Receptor-a Binding Requirements for Phenolic Mono- and Di-Hydroxyl Compounds: A Combined Synthesis, Binding and Docking Study Reference is made to McCullough et al., Biorg. & Med. Chem. (2014) Jan. 1; 22(1):303-10. doi: 10.1016/j.bmc.2013.11.024. Epub (2013) Nov. 21, and the corresponding Supplementary Information, the contents of which are incorporated herein by reference in their entireties.

Abstract

Various estrogen analogs were synthesized and tested for binding to human ERα using a fluorescence polarization displacement assay. Binding affinity and orientation were also predicted using docking calculations. Docking was able to accurately predict relative binding affinity and orientation for estradiol, but only if a tightly bound water molecule bridging Arg393/Glu353 is present. Di-hydroxyl compounds sometimes bind in two orientations, which are flipped in terms of relative positioning of their hydroxyl groups. Di-hydroxyl compounds were predicted to bind with their aliphatic hydroxyl group interacting with His524 in ERα. One nonsteroid-based dihydroxyl compound was 1,000-fold specific for ERβ over ERα, and was also 20-fold specific for agonist ERβ versus antagonist conformations. Docking predictions suggest this specificity may be due to interaction of the aliphatic hydroxyl with His475 in the agonist form of ERβ, versus with Thr299 in the antagonist form. But, the presence of this aliphatic hydroxyl is not required in all compounds, since mono-hydroxyl (phenolic) compounds bind ERα with high affinity, via hydroxyl hydrogen bonding interactions with the ERα Arg393/Glu353/water triad, and van der Waals interactions with the rest of the molecule.

1. Introduction

Estrogen receptor-a (ERα) is a 595-residue, 66 kDa protein with a ligand binding domain of 245 residues (28 kDa). ERα, along with estrogen receptor-β (ERβ), belongs to the nuclear hormone family of intracellular receptors. It is one of the two principal receptors responsible for binding the endogenous estrogen, 17β-estradiol (E2), shown in FIG. 1.[1] In the nucleus, ER binds to DNA as a dimer, recruiting coactivators or corepressors that will result in activating or repressing the transcription of different genes.[3] Binding of E2 activates the ER, regulating activity. Both ERα and ERβ forms are found in different tissue types. However, ERα is expressed more in breast tissue and is also known to be involved in the pathway that regulates breast cancer development.[2,4] ERα antagonists such as raloxifene (FIG. 1) can bind to ER in the same ligand-binding domain as E2, and disrupt normal ER cellular function.[4,5] (See FIG. 1).

A key structural feature of E2 is the presence of two hydroxyl groups that are separated by 11 Å, which permits interaction with conserved binding site residues Arg394/Glu353 and His 524. But, the receptor is capable of binding many other compounds whose structures resemble that of the E2 hormone.[6] Some of these compounds are endogeneous, such as estrone and other human estrogens; and, some are exogeneous, like the drugs raloxifene (FIG. 1) or tamoxifen that are used to treat breast cancer and osteoporosis.[7] In addition to drugs, there exist other exogeneous compounds, some naturally occurring like phytoestrogens and some synthetic such as organochlorines, that have measurable estrogenic activity.[5] Many of these latter compounds have been shown to be linked to breast cancer as well as birth defects.[8,9] Through the National Institutes of Environmental Health Sciences, the BSB (Biomolecular Screening Branch), and other federal agencies, the government has developed a program to test many of the chemicals currently in our environment, to see if they have estrogenic activity.[10]

Because of the estrogen receptor's prominent role as a breast cancer drug target, along with the threat posed by the potentially large number of estrogen agonists and antagonists in our environment (e.g. endocrine disruptors), it is essential to gain a better understanding of the binding requirements of the ERα ligand pocket. This understanding will allow for the design of better breast cancer drugs that interfere with the carcinogenic activity of estrogen agonists, and improve our ability to predict which pollutants might bind to ERα. Such predictions are strengthened by a better definition of the molecular features that trigger agonist or antagonist effects, as well as a validation of the docking methods used to predict binding.

One technique that can provide a quick and reliable experimental measurement of binding affinity is fluorescence polarization.[11] A fluorescence polarization displacement assay can be used to screen non-fluorescent molecules, by displacing a fluorescent probe with the molecule of interest.[12] Such fluorescence polarization displacement assays have been developed previously for ERα and ERβ, based on a fluorescein isothiocyanate (FITC)-tagged estradiol (F-E2).[13,14] One such assay is available from Invitrogen.[15] Subsequent studies in our lab improved the synthesis of F-E2 and examined the in vivo behavior of F-E2 in vivo, in fish. F-E2 was found to localize in cells that develop into reproductive organs, consistent with the proposed role of E2 in gender determination in fish.[16] An analogous fluorescence polarization method was developed using an intrinsically fluorescent nonsteroid estrogen.[17]

Herein we present the synthesis of a series of phenolic mono- and di-hydroxyl estrogen analogs, which were tested for binding affinity for human ERα, using a fluorescence polarization displacement assay based on F-E2. Estrogen (E2) is a phenolic compound comprised of a steroid core and a second hydroxyl group that is 11 Å from the phenolic hydroxyl. Compounds synthesized herein have the phenolic core, but vary in terms of whether they: (a) are steroid-based, and (b) possess a second hydroxyl group, ~11 Å from the phenol. In addition to binding affinity measurements for compounds, docking calculations were performed. Docking is the process of positioning a ligand into the binding site of a protein and calculating a binding energy for each pose.[18] It has become an important early-stage method for finding molecules likely to bind to a protein, allowing for many chemicals to be rapidly screened as potential drug leads.[18-20] Docking has also proven useful for identifying compounds as targets for pollutant bioremediation.[21] Besides predicting relative binding affinity, docking is used to predict the orientation or pose of a known ligand bound to a protein.[22] Comparison of docking predictions with experimental affinity measurements allows one to rationalize binding site requirements, and also provides validation of the predictive ability of the docking calculations for a given target (e.g. ERα) and class of compounds (phenolic mono- and di-hydroxyl compounds). This is important because such experimental validation provides greater confidence in the docking calculations when they are done on larger sets of compounds, where experimental verification might not be feasible.

2. Results and Discussion 2.1 Synthesis

Wittig olefination of estrone benzyl ether,[23] followed by epoxidation with mCPBA gave the known[24] epoxide 1 as a mixture of diastereomers (Scheme 1). Deprotonation of 1 with lithium diisopropylamine, followed by cleavage of the benzyl ether under dissolving metal conditions gave the allylic alcohol 2. Palladium catalyzed alkoxycarbonylation of the vinyl triflate derived from estrone benzyl ether, according to the literature procedure,[25] gave n-propyl (20S)-3-(phenylmethoxy)-estra-1,3,5(10), 16-tetraene-17-carboxylate (3), which upon reduction in the presence of Raney-Ni gave the saturated ester 4. The skipped diene (20S)-3-(phenylmethoxy)-19,24-dinorchola-1,3,5(10), 16,22-pentaene (5) was prepared by the literature procedure.[25] Hydrogenation of the less substituted olefin in the presence of Wilkinson's catalyst, followed by debenzylation gave 7. Hydroboration-oxidation of 5, by the literature procedure[26] gave (20S)-3-(phenylmethoxy)-19,24-dinorchola-1,3,5(10),16-tetraen-23-ol (8). Subjecting 8 to acid resulted in the spirocyclic tetrahydrofuran 9 in quantitative yield, which upon catalytic hydrogenolysis gave 10. Alternatively, debenzylation of 8 afforded 11. Oxidation of 11 gave the aldehyde 12. Reaction of 12 with an excess of methyl Grignard, followed by work-up with saturated aqueous ammonium chloride proceeded by cyclization to afford the spirocyclic tetrahydrofuran 13 as a mixture of diastereomers.

Scheme 1.

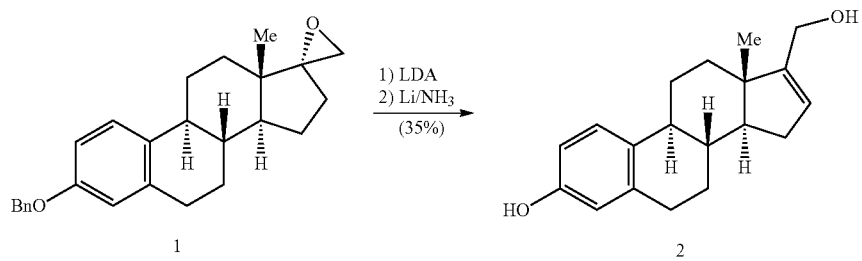

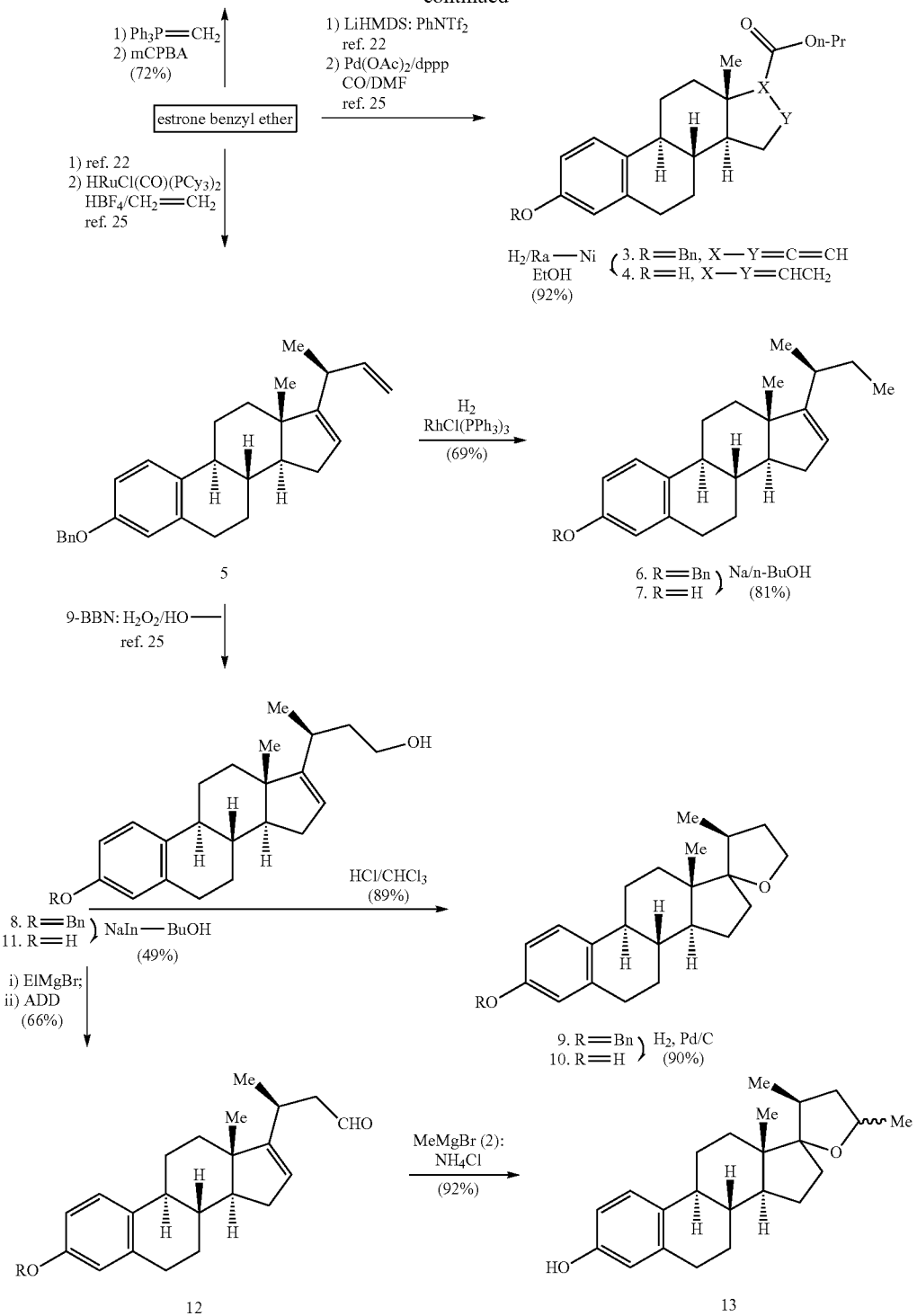

A series of p-substituted phenols were also prepared (Scheme 2). Reduction of 4-(4'-hydroxyphenyl)cyclohexanone gave a separable mixture of trans-4-(4'-hydroxycyclohexyl)phenol 15 (86%) and its cis-diastereomer 14 (10%). The stereochemical assignments for each were made by comparison to their literature spectral data.[27] Reaction of 4-(4'-hydroxyphenyl)cyclohexanone with hydroxylamine-hydrochloride gave the oxime 16. [4-((4'-Hydroxyphenyl)cyclohepta-2,6-dienyl)methanol 17 was prepared from p-acetoxystyrene according to the literature procedure.[28] This involved cross metathesis with (1-methoxycarbonyl-2-vinyl-3-pentene-1,5-diyl)Fe(CO)$_3$ (21), followed by oxidatively induced reductive elimination. Reduction of the resultant cyclopropanecarboxylate and concomitant Cope [3,3]-rearrangement gave the cycloheptadiene 17. Catalytic reduction of 17 gave the saturated cycloheptane 18. Finally, Heck-type coupling of methyl 5-bromo-2-furanoate with p-acetoxystyrene gave the trans-styrylfuranoate 19, which upon reduction with lithium aluminum hydride gave the furfuryl alcohol 20.

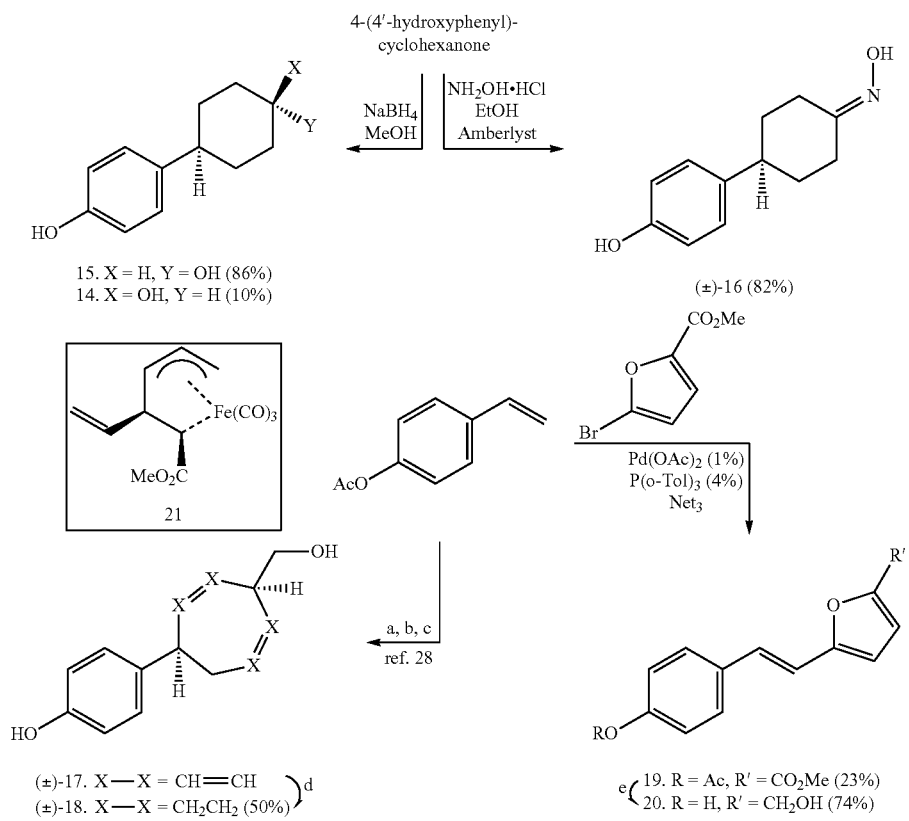

2.2 Fluorescence Polarization Displacement and Cell-Based ERα and ERβ Luminescence Activity Assays Twelve compounds from Schemes 1 and 2 were screened using fluorescence polarization, for their ability to bind ERα (Table 1). Only six compounds showed any significant affinity for the receptor at concentrations as high as 1 μM. These compounds include five of the six steroid-core compounds—2, 4, 7, 11, and 13—and one bicyclic compound—18. Of the remaining six compounds which did not bind to ERα, one has the steroid core while the others contain the linked ring cores containing a flanking hydroxyl group—a structure whose hydrophobic interior and hydrophilic exterior resembles that of estrogen itself. The highest affinity ERα ligand was 2, with a $K_d$ (32 nM) approaching that of E2 (3 nM). 18 is the only non-steroid core compound with measurable ERα binding affinity, but an accurate $K_d$ could not be obtained (estimated to be >1 μM).

TABLE 1

Dissociation constants ($K_d$) from the fluorescence polarization displacement assay and $IC_{50}$ data from cell-based ERα and ERβ agonist assays and ERβ antagonist assays

| Compound | ERα $K_d$ (nM) | ERα agonist $IC_{50}$ (nM) | ERβ agonist $IC_{50}$ (nM) | ERβ antagonist $IC_{50}$ (nM) |
|---|---|---|---|---|
| E2 | $3^{15}$ | $1.3^{27}$ | $46\ pM^{27}$ | NA |
| 11 | 320 ± 40 | NA | 108 ± 67 | 275 ± 40 |
| 4 | 320 ± 40 | 92 ± 1 | 9.8 ± 2 | NA |
| 7 | 160 ± 10 | NA | 88 ± 9 | 70 ± 15 |
| 13 | 160 ± 10 | 484 ± 1 | 111 ± 26 | NA |

TABLE 1-continued

Dissociation constants ($K_d$) from the fluorescence polarization displacement assay and $IC_{50}$ data from cell-based ERα and ERβ agonist assays and ERβ antagonist assays

| Compound | ERα $K_d$ (nM) | ERα agonist $IC_{50}$ (nM) | ERβ agonist $IC_{50}$ (nM) | ERβ antagonist $IC_{50}$ (nM) |
|---|---|---|---|---|
| 2 | 32 ± 5 | 145 ± 1 | 6.8 ± 0.2 | NA |
| 18 | >1 μM | NA | 5.4 ± 0.3 | 137 ± 100 |

ERα antagonist behavior was not observed.
NA indicates data was not of sufficient quality to measure activity.
Assay data for E2 binding to ERα,[15] and ERα agonist and ERβ agonist and antagonist activity in cellular assays,[27] were previously reported.

Cell-based ERα and ERβ luminescence assays were performed to determine whether the ERα ligands were acting as agonists or antagonists, and whether they had specificity for the α isoform (Table 1, FIGS. 3-8). Three compounds, 4, 13, and 2, showed agonist activity in the ERα assay; and, all six compounds showed ERβ agonist activity, with 4, 2, and 18 being the most potent; 18 is unique in its selectivity for ERβ over ERα, and is 20-fold more potent as an antagonist, versus agonist. 11, 7, and 18 displayed ERβ antagonist activity, with 7 being the most potent.

2.3 Docking

Compounds were computationally docked into human ERα and ERβ in agonist and antagonist conformations. Poses for ERα are shown in FIGS. 9 and 10. Initial control docking studies were performed with E2, to validate the docking method by demonstrating an ability to reproduce the known binding mode from the crystal structure. Interestingly, E2 docked with similar predicted affinity in two distinct poses for the ERα agonist conformation (Table 3), essentially flipping the positioning of the two hydroxyl groups with regard to interactions with Arg394/Glu353 and His524, located on opposite sides of the pocket. The predicted pose with the phenolic hydroxyl near Arg394/Glu353 is referred to as the "normal" mode, and that with the phenolic hydroxyl near His524 as the "reversed" mode. But, if docking is performed on receptor that has the tightly bound water present near Arg394/Glu353, then only the expected pose is obtained; and, E2 is the ligand with highest predicted affinity (Table 2), as expected. Thus, all docking was performed with the Arg394/Glu353 water present. This binding mode has been studied previously using molecular dynamics, and illustrates the important role of active site water molecules in ligand binding.[30]

Docking results were rank ordered according to the lowest energy pose for binding to the ERα agonist conformation, from the cluster with the highest population (Table 2). Identifying the compounds with measurable $K_d$ values from the fluorescence polarization displacement assay (shown as bold in Table 2) indicates that the docking procedure using Autodock4 was able to separate the binding ligands from the non-binding ligands. ER is a unique docking target, since the binding site is comprised of a nearly closed hydrophobic pocket, flanked by hydrogen bonding groups that could provide specificity.[31] Care in analyzing docking results is needed due to the large binding area in which ligands can potentially bind, and symmetry of the pocket. Three examples of reversed binding modes that are likely false are shown in FIG. 2.

Interestingly, while estradiol docked in only one orientation when the bound water is present, other compounds were still predicted to bind in two orientations (Table 2; FIG. 2), one normal (with the phenolic hydroxyl interacting with Arg392/Glu353/Water), and one "reversed," where the phenolic hydroxyl interacts with His524. This promiscuity in predicted binding mode may be due to symmetry in di-hydroxyl molecules like 2 (FIG. 2). Curiously, the mono-hydroxyl 4 also is predicted to bind in a reversed mode (FIG. 2), but with much lower affinity relative to the normal mode. This is likely due to the fact that 4 has only one hydroxyl group, the phenol, which provides significant binding energy via interaction with the Arg392/Glu353/water triad. It is also clear that the aliphatic hydroxyl interaction with His524 is not essential, since it is absent in 4 and 7, and yet both bind with reasonable affinity ($IC_{50}$=160-320 nM). Indeed, this observation is consistent with the ability of phenolic endocrine disruptors, which contain only one hydroxyl group, to bind to ER.[33] (See FIG. 2).

TABLE 2

Docking of compounds prepared in Schemes 1 and 2 into the agonist and antagonist conformations of ERα and ERβ

| Compound | Docking score for ERα agonist (kcal mol$^{-1}$) | Docking score for ERα antagonist (kcal mol$^{-1}$) | Docking score for ERβ agonist (kcal mol$^{-1}$) | Docking score for ERβ antagonist (kcal mol$^{-1}$) |
|---|---|---|---|---|
| E2 | −10.36 | −9.70 | −10.11 | −9.29 |
| 4 | −10.29 | −10.38 | −10.66 | −10.13 |
| 2 | −9.82 | −9.86 | −10.40 | −9.71 |
| 11 | −9.80 | −9.30 | −10.18 | −10.28 |
| 7 | −9.74 | −9.37 | −10.00 | −10.36 |
| 10 | −8.82 | −9.21 | −6.41 | −10.08 |
| 13 | −8.73 | −8.82 | −4.82 | −9.92 |
| 18 | −8.22 | −7.66 | −7.86 | −7.48 |
| 17 | −7.37 | −7.10 | −6.97 | −6.83 |
| 16 | −7.27 | −6.99 | −6.92 | −6.96 |
| 20 | −6.93 | −7.20 | −7.34 | −7.11 |
| 15 | −6.85 | −6.38 | −6.56 | −6.77 |
| 14 | −6.41 | −6.28 | −6.43 | −6.60 |

Compounds identified as having ERα affinity in the fluorescence polarization displacement assay are in bold.

The docking of compounds 10 and 13 in the ERβ-agonist conformation displayed predicted binding energies that were weaker than expected in Table 2. Inspection of the binding site) showed that these ligands experience steric clashes with binding site sidechains. Additionally, for structures 10 and 13, the oxygen atom in the tetrahydrofuran ring was not positioned near His475 for 10 or (for reversed mode binding) near Arg346, Glu305 for 13, to allow for hydrogen bond formation hydrogen bonds.

Compound 18 is in a unique class, in that it is not based on the steroid core, is selective for the β over the α ER isoform, and is 25-fold selective for ERβ agonist versus ERβ antagonist activity (Table 1). Docking pose predictions (FIGS. 2C and 2D) show that 18 could form two hydrogen bonds (one with His475) in the ERβ agonist conformation, whereas in the ERβ antagonist conformation, hydrogen bonding is with Thr299, rather than His475. A molecular overlay of E2 and 18 shows the oxygen atoms of the two molecules are well-aligned (data not shown).

Conclusion

Human ERα remains an important target for therapeutic interventions (cancer; osteoporosis). Estrogen has a key interaction between its phenolic hydroxyl and a binding site Arg394/Glu353/water triad, along with other important interactions including van der Waals interactions with the steroid core, and hydrogen bonding interactions between an aliphatic hydroxyl group and His524 (His475 in ERβ). The two estradiol hydroxyls are located 11 Å from each other. The studies presented herein probe the importance of interactions with the aliphatic hydroxyl and with the steroid core, using a series of novel mono- and di-hydroxyl compounds (Schemes 1 and 2).

The estrogen analog with highest measured affinity in the fluorescence polarization displacement assay ($IC_{50}$=32 nM) and second highest predicted affinity is the di-hydroxyl steroid 2, which has a single point of unsaturation in the D-ring, and (relative to estradiol) has its aliphatic hydroxyl extended by one methylene group. Nonetheless, this gives an O—O distance essentially equivalent to that for estradiol. Di-hydroxyl steroid 2 behaves as an ERα agonist, and has only modest selectivity for α versus β ER isoforms. Indeed, 2 is a potent ERβ agonist and antagonist. In contrast, 18 binds weakly to ERα, yet has on O—O distance (11.1 Å) that is similar to 2. Of particular interest is the fact that 18 has the expected interaction with His475 in the ERβ agonist docking, whereas in the ERβ antagonist docking this aliphatic hydroxyl group is predicted to interact instead with Thr299 (FIG. 2). This could explain why 18 is so selective (25-fold) as an ERβ agonist, versus as an antagonist (Table 1). Most of the other compounds from Scheme 2 that lacked the steroid core did not bind to ERα, even though they possessed the phenolic hydroxyl. Compounds (4, 13, 2), which possessed ERα agonist activities, were also ERβ agonists; but, not ERβ antagonists. And, these compounds were more selective for ERβ over ERα.

In summary, several compounds have been identified that are potent ERα agonists, and also behave as ERβ agonists and antagonists (Table 1). The most potent is the dihydroxyl steroid 2. Also, the non-steroid dihydroxyl compound 18 is 1,000-fold more selective for ERβ over ERα, and appears to adopt a different binding mode in these two targets (FIG. 2).

Experimental Section

4.1 General Methods

The β-estradiol (min. 98%) and fluorescein (FITC) were purchased from Sigma. The α-ER and α-ER screening buffer were from Invitrogen. The FITC-estradiol linked tracer used in the experiments was synthesized by as described previously.(1) $d_6$-DMSO was purchased from Cambridge Isotopes. The 96-well plates used were black, polystyrene, NBS (non-binding surface), flat-bottom plates obtained from Corning. A PolarStar Galaxy fluorescent plate reader was used and controlled with FLUOStar Galaxy software (version 4.30-0). Estrone benzyl ether[23] and compounds 3,[25] 5,[26] 8,[26] and 17[28] were prepared by the literature procedures.

4.2 Estrogen Analog Synthesis

4.2.1 3-Hydroxvestra-1,3,5(10),16-tetraene-17-methanol (2)

To a solution of methyl triphenylphosphonium bromide (589 mg, 1.65 mmol) in THF (10 mL) at −40° C. under $N_2$, was added a solution of n-butyl lithium (0.66 mL, 2.5 M in hexanes, 1.7 mmol). The ylide solution was warmed to room temperature and a solution of estrone benzyl ether (200 mg, 0.556 mmol) in THF (7 mL) was added. The mixture was stirred for 12 h, and then heated at reflux for 5 h. The solution was cooled, and concentrated, and the residue was purified by column chromatography ($SiO_2$, hexanes-ethyl acetate=4:1) to afford the exocyclic methylene product (168 mg, 84%) as a colorless solid. This product was used in the next step without further characterization. To a solution of the olefin (100 mg, 0.279 mmol) in dichloromethane (6 mL) at 0° C., was added solid m-chloroperoxybenzoic acid (57.5 mg, 0.333 mmol). The reaction mixture was 4 h, and then quenched with aqueous $NaHCO_3$. The mixture was extracted several times with dichloromethane, dried and concentrated to afford the epoxide 1 (90 mg, 86%) as a colorless oil, which was used in the next step without further purification. To a solution of the epoxide (50 mg, 0.13 mmol) in hexanes (1 mL) and toluene (0.5 mL) was added HMPA (1 drop). The mixture was cooled to −78° C., and then a solution of lithium diisopropylamine in hexanes (0.73 mmol) was added. The solution was warmed to room temperature and stirred for 10 h. The mixture was quenched with saturated aqueous $NH_4Cl$, and the mixture extracted several times with ether. The combined extracts were dried ($MgSO_4$) and concentrated, and the residue was purified by column chromatography ($SiO_2$, hexanes-ethyl acetate=3:2) to afford a colorless oil (29 mg, 58%) which was used without further characterization. To liquid ammonia (ca. 10 mL), at −78° C. was added lithium metal (24 mg, 3.5 mmol), followed by t-butyl alcohol (0.05 mL). To this solution was added a solution of the allylic alcohol (20 mg, 0.053 mmol) in THF (1 mL). The reaction mixture was stirred at −78° C. for 15 min, and then quenched with $NH_4Cl$, and diluted with ether. The mixture was warmed to room temperature, and water (10 mL) was added. The mixture was extracted several times with ether followed by extraction with dichloromethane. The combined extracts were dried ($MgSO_4$), concentrated and the residue was purified by column chromatography ($SiO_2$, hexanes-ethyl acetate=3:2) to afford 2 (9.0 mg, 60%) as a colorless solid. mp 192-194° C.; $^1$H NMR ($CDCl_3$, 400 MHz) δ 7.15 (d, J=8.4 Hz, 1H), 6.64 (dd, J=2.8, 8.4 Hz, 1H), 6.58 (d, J=2.8 Hz, 1H), 5.65 (dd, J=1.2, 2.8 Hz, 1H), 4.80 (br s, OH), 4.32-4.25 (m, 2H), 2.95-2.80 (m, 2H), 2.40-1.70 (m, 11H), 0.87 (s, 3H); $^{13}$C NMR ($CDCl_3$, 100 MHz) δ 155.2, 153.5, 138.5, 133.1, 126.4, 124.3, 126.4, 124.3, 115.5, 112.8, 60.4, 56.8, 46.4, 44.6, 37.4, 34.8, 31.1, 29.7, 27.9, 26.6, 16.5.

4.2.2 n-Propyl 3-hydroxyestra-1,3,5(10)-triene-17-carboxylate (4)

To a solution of 3 (177 mg, 0.411 mmol) in ethanol (10 mL) was added an aqueous slurry of Raney-Ni (60%, 0.6 mL). The reaction mixture was stirred under a $H_2$ gas (balloon pressure) for 24 h, after which the mixture was filtered through a bed of filter-aid. The filter bed was washed several times with ethyl acetate, and the filtrate was concentrated under reduced pressure to afford 4 as a colorless solid (129 mg, 92%): mp 151.5-153° C., $[a]_D^{20}$+69.5 (c 0.388, $CHCl_3$); $^1$H NMR ($CDCl_3$, 300 MHz) δ 7.17 (d, J=8.4 Hz, 1H), 6.64 (dd, J=2.8, 8.5 Hz, 1H), 6.57 (d, J=2.7 Hz, 1H), 4.55 (br s, OH), 4.10 (dt, J=10.8, 6.7 Hz, 1H), 4.02 (dt, J=10.8, 6.7 Hz, 1H), 2.90-2.80 (m, 2H), 2.44 (t, J=9.3 Hz, 1H), 2.35-2.15 (m, 3H), 1.90-1.75 (m, 3H), 1.68 (sextet, J=7.2 Hz, 2H), 1.55-1.30 (m, 7H), 0.98 (t, J=7.3 Hz, 3H), 0.71 (s, 3H); $^{13}$C NMR ($CDCl_3$, 75 MHz) δ 174.5, 153.5, 138.4, 132.8, 126.7, 115.4, 112.8, 66.0, 55.6, 55.1, 44.3, 43.9, 39.0, 38.6, 29.8, 27.8, 26.7, 24.3, 23.7, 22.3, 13.7, 10.9. Anal. calcd. for $C_{22}H_{30}O_3 \cdot 1/2H_2O$: C, 75.18; H, 8.89. Found: C, 75.36; H, 8.28.

4.2.3 (20S) 3-(Phenylmethoxy)-19,24-dinorchola-1,3,5(10),16-tetraene (6)

To a solution of 5 (0.20 g, 0.50 mmol) in benzene (10 mL) in a Schlenk flask was added $Rh(PPh_3)_3Cl$ (40 mg, 0.043 mmol). The reaction mixture was cooled with a dry ice-acetone bath, evacuated under high vacuum, and the system refilled to 1 atm with $H_2$ gas. The mixture was stirred for 7 h at room temperature, and then the solvent was evaporated. The residue was extracted several times with ether, filtered, and concentrated. The residue was purified by column chromatography ($SiO_2$, hexanes-$CH_2Cl_2$=10:1) to afford 6 (138 mg, 69%) as a colorless solid. mp 82-83.5° C., $[a]_D^{20}$+ 67 (c 0.74, acetone); $^1$H NMR ($CDCl_3$, 300 MHz) δ 7.46-7.30 (m, 5H), 7.20 (d, J=8.4 Hz, 1H), 6.78 (br d, J=8.4 Hz, 1H), 6.74 (br s, 1H), 5.35 (br s, 1H), 5.04 (s, 2H), 2.94-2.84 (m, 2H), 2.40-2.08 (m, 4H), 2.00-1.87 (m, 3H), 1.65-1.28 (m, 7H), 1.09 (d, J=6.6 Hz, 3H), 0.89 (t, J=7.3 Hz, 3H), 0.83 (s, 3H); $^{13}$C NMR ($CDCl_3$, 75 MHz) δ 160.2, 155.9, 137.6, 136.7, 132.9, 128.0, 127.3, 127.0, 125.6, 120.4, 114.4, 111.8, 70.0, 56.4, 47.8, 44.7, 37.8, 35.4, 33.6, 31.3, 30.3, 30.2, 28.2, 27.0, 21.3, 17.1, 12.4. Anal. calcd. for $C_{29}H_{36}O$: C, 86.95; H, 9.06. Found: C, 86.99; H, 9.12.

4.2.4 (20S) 3-Hydroxy-19,24-dinorchola-1,3,5(10), 16-tetraene (7)

Cleavage of the benzyl ether 6 (73 mg, 0.18 mmol) with sodium metal in n-butanol was carried out in a fashion similar to the cleavage of 8. Purification of the residue by column chromatography (SiO$_2$, hexanes-ethyl acetate gradient=5:1) gave unreacted starting material (17 mg) followed by 7 (46 mg, 81%) as a colorless solid. mp 92-95° C., [a]$_D^{20}$+86.3 (c 0.32, acetone); $^1$H NMR (d$_6$-acetone) δ 7.05 (d, J=8.4 Hz, 1H), 6.56 (dd, J=2.1, 8.4 Hz, 1H), 6.51 (d, J=2.1 Hz, 1H), 5.35 (br s, 1H), 2.82-2.73 (m, 2H), 2.37-2.28 (m, 1H), 2.22-2.05 (m, 2H), 1.97-1.85 (m, 4H), 1.60-1.26 (m, 8H), 1.07 (d, J=7.2 Hz, 3H), 0.87 (t, J=7.5 Hz, 3H), 0.82 (s, 3H); $^{13}$C NMR (d$_6$-acetone) δ 162.5, 156.7, 139.3, 133.2, 127.7, 122.7, 117.1, 114.7, 58.8, 50.0, 47.1, 40.4, 37.7, 35.8, 33.4, 32.5, 32.2, 30.6, 29.3, 23.2, 19.0, 14.1. Anal. calcd. for C$_{22}$H$_{30}$O.1/6H$_2$O: C, 84.28; H, 9.75. Found: C, 84.28; H, 9.82.

4.2.5 (20S) 3-Hydroxy-19,24-Dinorchola-1,3,5(10), 16-tetraen-23-ol (11)

To a solution of 8 (394 mg, 0.947 mmol) in n-butanol (20 mL), at 70° C., was added sodium metal (0.87 g, 38 mmol) in small pieces. After all of the sodium had reacted, the reaction mixture was cooled to room temperature and quenched with water, followed by saturated aqueous NH$_4$Cl. The reaction mixture was extracted several times with ether, the combined extracts were dried (MgSO$_4$) and concentrated. The residue was purified by column chromatography (SiO$_2$, hexanes-ethyl acetate gradient=4:1 to 2:1) to afford unreacted starting material (91 mg) followed by 11 (150 mg, 49%) as a colorless solid. mp 174.5-176° C., [a]$_D^{20}$+77.5 (c 1.50, acetone); $^1$H NMR (d$_6$-acetone) δ 8.15 (s, phenol OH), 7.04 (d, J=8.4 Hz, 1H), 6.56 (dd, J=2.7, 8.4 Hz, 1H), 6.51 (d, J=2.7 Hz, 1H), 5.38 (br s, 1H), 3.64-3.52 (m, 3H), 2.84-2.74 (m, 2H), 2.42-2.28 (m, 2H), 2.20-2.08 (m, 1H), 1.96-1.70 (m, 4H), 1.60-1.30 (m, 7H), 1.10 (d, J=7.2 Hz, 3H), 0.82 (s, 3H); $^{13}$C NMR (d$_6$-acetone) δ 162.8, 156.6, 139.2, 133.0, 127.6, 122.6, 117.0, 114.6, 61.4, 58.7, 49.9, 47.0, 43.0, 40.3, 37.5, 33.2, 32.0, 30.9, 30.5, 29.2, 23.7, 19.0. Anal. calcd. for C$_{22}$H$_{30}$O$_2$: C, 80.94; H, 9.26. Found: C, 80.67; H, 9.32.

4.2.6 17,23-Epoxy-3-(phenylmethoxy)-19,24-dinorchola-1,3,5(10)-triene (9)

To a solution of 8 (56 mg, 0.14 mmol) in CHCl$_3$ (2 mL) was added a drop of concentrated HCl. The mixture was allowed to stand stirred for 24 h at room temperature, and then passed through a short column of silica gel using hexanes-ethyl acetate as eluent. Concentration of the eluent gave 9 (50 mg, 89%) as a colorless oil. [a]$_D^{20}$+36 (c 1.0, CH$_2$Cl$_2$); $^1$H NMR (CDCl$_3$, 300 MHz) δ 7.46-7.28 (m, 5H), 7.22 (d, J=8.4 Hz, 1H), 6.87 (dd, J=2.7, 8.4 Hz, 1H), 6.73 (d, J=2.7 Hz, 1H), 5.04 (s, 2H), 3.87 (dt, J=4.5, 7.8 Hz, 1), 3.62 (dt, J=6.4, 7.8 Hz, 1H), 2.92-2.82 (m, 2H), 2.38-1.20 (m, 16H), 1.10 (d, J=6.9 Hz, 3H), 0.74 (s, 3H); $^{13}$C NMR (CDCl$_3$, 75 MHz) δ 155.8, 137.6, 136.7, 132.8, 128.2, 127.3, 126.9, 125.8, 114.4, 111.8, 95.5, 70.0, 66.0, 50.0, 48.2, 44.0, 39.3, 36.9, 35.1, 31.3, 31.0, 30.3, 28.1, 26.6, 23.6, 19.0, 15.8. Anal. calcd. for C$_{29}$H$_{36}$O$_2$: C, 83.61; H, 8.71. Found: C, 83.35; H, 8.75.

4.2.7 17,23-Epoxy-3-hydroxy-19,24-dinorchola-1,3, 5(10)-triene (10)

To a solution of 9 (48.9 mg, 0.118 mmol) in methanol/CHCl$_3$ (1:100, 6 mL) was added 10% Pd on carbon (5.6 mg). The mixture was stirred under H$_2$ (ca. 46 psi) in a Paar hydrogenation apparatus for 3 h. The catalyst was removed by filtration through filter-aid and the filter bed was washed with copious CH$_2$Cl$_2$ and the combined filtrates were concentrated. The residue was purified by chromatography (SiO$_2$, hexanes-ethyl acetate=3:1) to afford 10 as a colorless solid (37.8 mg, 99%). mp 172-174° C.; $^1$H NMR (CDCl$_3$, 300 MHz) δ 7.15 (d, J=8.4 Hz, 1H), 6.62 (dd, J=2.7, 8.4 Hz, 1H), 6.55 (d, J=2.7 Hz, 1H), 3.87 (dt, J=4.5, 7.8 Hz, 1H), 3.60 (dt, J=6.3, 8.1 Hz, 1H), 2.85-2.75 (m, 2H), 2.35-1.20 (m, 16H), 1.07 (d, J=6.9 Hz, 3H), 0.70 (s, 3H); $^{13}$C NMR (CDCl$_3$, 75 MHz) δ 153.3, 138.6, 133.2, 126.6, 115.4, 112.7, 96.0, 66.1, 50.0, 48.2, 43.9, 39.3, 36.8, 35.0, 31.2, 30.8, 30.0, 27.9, 26.4, 23.4, 18.8, 15.6. Anal. calcd. for C$_{22}$H$_{30}$O$_2$.1/4H$_2$O: C, 79.83; H, 9.29. Found: C, 80.12; H, 9.33.

4.2.8 (20S) 3-Hydroxy-19,24-dinorchola-1,3,5(10), 16-tetraen-23-al (12)

To a solution of 11 (100 mg, 0.296 mmol) in THF (4 mL) was added a solution of ethyl magnesium bromide in THF (0.67 mL, 1.0 M, 0.67 mmol). The solution was stirred at room temperature for 15 min, and then solid 1,1'-(azodicarbonyl)dipiperidine (0.17 g, 0.67 mmol) was added. The reaction mixture was stirred for 1 h, and then quenched with saturated aqueous NH$_4$Cl and extracted several times with ether. The combined ethereal extracts were dried (MgSO$_4$), concentrated and the residue was purified by column chromatography (SiO$_2$, hexanes-ethyl acetate=5:1) to afford 12 as a colorless solid (66 mg, 66%). mp 168.5-171° C., [a]$_D^{20}$+78 (c 0.80, acetone); $^1$H NMR (d$_6$-acetone, 300 MHz) δ 9.66 (t, J=2.1 Hz, 1H), 7.06 (d, J=8.4 Hz, 1H), 6.57 (dd, J=2.5, 8.4 Hz, 1H), 6.51 (d, J=2.5 Hz, 1H), 5.46 (br s, 1H), 2.90-2.75 (m, 4H), 2.62 (ddd, J=1.8, 5.7, 16.2 Hz, 1H), 2.44-2.30 (m, 2H), 2.26-2.10 (m, 2H), 1.98-1.86 (m, 3H), 1.60-1.34 (m, 5H), 1.16 (d, J=7.2 Hz, 3H), 0.88 (s, 3H); $^{13}$C NMR (d$_6$-acetone, 75 MHz) δ 203.2, 161.4, 156.8, 139.5, 133.3, 127.9, 124.6, 117.2, 114.8, 59.2, 53.1, 50.2, 47.2, 40.5, 37.7, 33.6, 32.3, 30.7, 29.7, 29.4, 23.8, 19.3. Anal. calcd. for C$_{22}$H$_{28}$O$_2$: C, 81.44; H, 8.70. Found: C, 81.21; H, 8.54.

4.2.9 17,23-Epoxy-3-hydroxy-19-norchola-1,3,5 (10)-triene (13)

To a solution of 12 (45.9 mg, 0.142 mmol) in THF (7 mL) at 0° C. was added a solution of methyl magnesium bromide in ether (0.10 mL, 3.0 M, 0.30 mmol). The reaction mixture was stirred for 3 h, and then quenched with saturated aqueous NH$_4$Cl (15 mL). The mixture was extracted several times with CH$_2$Cl$_2$ and the combined extracts were dried (MgSO$_4$) and concentrated. The residue was purified by chromatography (SiO$_2$, hexanes-ethyl acetate=5:1) to afford 13 as a colorless solid (44 mg, 92%). Analysis of the product by $^1$H NMR spectroscopy indicated this to be a 1:1 mixture of diastereomers. mp 248-251° C., $^1$H NMR (CDCl$_3$, 300 MHz) δ 7.15 (d, J=8.4 Hz, 1H), 6.62 (dd, J=2.7, 8.4 Hz, 1H), 6.56 (d, J=2.7 Hz, 1H), 4.18-4.07 (m, 1H), 3.85-3.74 (m, 1H), 2.85-2.75 (m, 2H), 2.35-1.20 (m, 15H), 1.23 & 1.20 (2×d, J=5.7 Hz, 3H total), 1.07 & 1.05 (2×d, J=6.9 Hz, 3H), 0.72 & 0.66 (2×s, 3H total); $^{13}$C NMR (CDCl$_3$, 75 MHz) δ 153.3, 138.6, 133.2, 126.6, 115.4, 112.7, 97.1 [95.8], 73.6 [71.3], 49.85 [49.80], 48.8, 47.1, 45.4, 43.9 [43.8], 43.5, 39.3 [39.2], 36.2, 34.5, 32.3, 31.2 [30.9], 30.6 [30.1], 27.8, 26.4, 23.5 [23.4], 21.6, 19.2 [18.9], 16.3 [14.9]. Anal. calcd. for C$_{23}$H$_{32}$O$_2$. 1/2H$_2$O: C, 79.04; H, 9.52. Found: C, 79.34; H, 9.57.

4.2.10 cis- and trans-4-(4'-Hydroxycyclohexyl)phenol (14)

To a solution of 4-(4'-hydroxyphenyl)cyclohexanone (50 mg, 0.26 mmol) in methanol (1 mL) was added NaBH$_4$ (15 mg, 4.0 mmol). The reaction mixture was stirred for 30 min, and then diluted with water. The mixture was extracted several times with ethyl acetate and the combined extracts were concentrated and purified by column chromatography (SiO$_2$, hexanes-ethyl acetate=2:1) to afford cis-14 (5.0 mg, 10%) followed by trans-15 (43 mg, 86%) both as colorless solids. Cis-14: $^1$H NMR (CD$_3$OD, 400 MHz) δ 7.04-6.69 (AA'BB', J$_{AB}$=8.8 Hz, 4H), 4.02 (narrow t, J=2.8 Hz, 1H), 2.50-2.40 (m, 1H), 1.91-1.79 (m, 4H), 1.69-1.52 (m, 4H); $^{13}$C NMR (CD$_3$OD, 75 MHz) δ 156.5, 140.1, 128.8, 116.1, 66.5, 44.5, 34.0, 29.4. Trans-15: $^1$H NMR (CD$_3$OD, 400 MHz) δ 7.01-6.68 (AA'BB', J$_{AB}$=8.4 Hz, 4H), 3.58 (tt, J=4.4, 10.6 Hz, 1H), 2.39 (tt, J=3.5, 11.8 Hz, 1H), 2.06-1.99 (m, 2H), 1.87-1.79 (m, 2H), 1.56-1.33 (m, 4H).

4.2.11 4-(4-Hydroxyphenyl)-cyclohexanone Oxime (16)

To a solution of 4-(4'-hydroxyphenyl)cyclohexanone (50 mg, 0.26 mmol), hydroxylamine hydrochloride (36.6 mg, 0.526 mmol) in ethanol (5 mL) was added Amberlyst (56 mg). After stirring for 2 h, the mixture was filtered, and the filtrate concentrated. The residue was partitioned between water and ethyl acetate, and the organic layer was concentrated and dried to give (±)-16 (44 mg, 82%) as a colorless solid. mp 172-175° C. $^1$H NMR (CD$_3$OD, 400 MHz) δ 7.03-6.69 (AA'BB', J$_{AB}$=8.8 Hz, 4H), 4.02 (narrow t, J=2.8 Hz, 1H), 2.0-2.40 (m, 1H), 1.91-1.79 (m, 4H), 1.69-1.52 (m, 4H); $^{13}$C NMR (CD$_3$OD, 75 MHz) δ 161.0, 156.8, 138.4, 128.7, 116.3, 44.3, 36.0, 34.7, 33.0, 25.2. HRMS (ESI): m/z calcd for C$_{12}$H$_{15}$NO$_2$+Na$^+$[M+Na]$^+$228.0995, found 228.0997.

4.2.12 cis-1-Hydroxymethyl-4-(4'-hydroxyphenyl)-cycloheptane (18)

To a solution of (±)-17 (75 mg, 0.35 mmol) in methanol (15 mL) in a heavy walled reaction vessel, was added a catalytic amount of 20% Pd/C. The mixture was stirred under H$_2$ pressure (45 psi) for 75 min and then the reaction mixture was filtered through the pad of celite. The filtrate was concentrated and the residue was purified by column chromatography (SiO$_2$, hexanes-ethyl acetate=65:35) to afford (±)-18 (38 mg, 50%) as a colorless solid. mp 60-61° C.; $^1$H NMR (CDCl$_3$, 300 MHz) δ 7.06 and 6.75 (AA'BB', J$_{AB}$=9.0 Hz, 4H), 3.48 (d, J=6.3 Hz, 1H), 2.59-2.58 (m, 1H), 1.95-1.08 (m, 13H); $^{13}$C NMR (CD$_3$OD, 75 MHz) δ 127.9, 115.3, 68.6, 46.1, 41.4, 38.8, 33.1, 31.6, 28.5, 27.5. HRMS (ESI): m/z calcd for C$_{14}$H$_{20}$O$_2$+Na$^+$[M+Na]$^+$243.1356, found 243.1356.

4.2.13 5-[(1E)-2-(4-Hydroxyphenyl)ethenyl]-2-furanmethanol (20)

A solution of methyl 5-bromo-2-furanoate (1.03 g, 5.02 mmol), 4-acetoxystyrene (0.97 g, 6.0 mmol), palladium acetate (0.01 g, 0.05 mmol), tri-o-tolylphosphine (0.03 g, 0.2 mmol), and triethylamine (3 mL) was heated under nitrogen in a sealed heavy-walled Pyrex tube at 100° C. for 24 h. The reaction mixture was cooled, diluted with water and dichloromethane. The dichloromethane layer was separated, washed with water, and dried (MgSO$_4$), and the residue was purified by column chromatography (SiO$_2$, hexanes-ethyl acetate=4:1) to afford 19 (350 mg, 24%), a pale yellow solid. mp 110.5-112° C.; $^1$H NMR (CDCl$_3$, 300 MHz) δ 7.51 (d, J=8.1, 2H), 7.27 (d, J=16.5 Hz, 1H), 7.20 (d, J=3.6 Hz, 1H), 7.10 (d, J=8.1 Hz, 2H), 6.86 (d, J=16.5 Hz, 1H), 6.45 (d, J=3.6 Hz, 1H), 3.92 (s, 3H, OMe), 2.32 (s, 3H, OAc). This product was used in the next step without further characterization. To a solution of diester (50 mg, 0.17 mmol) in anhydrous ether (1 mL) at 0° C., was slowly added a solution of lithium aluminium hydride (0.52 mL, 1.0 M in THF, 0.52 mmol). Solution was stirred for 3 h at 0° C. and then saturated aqueous sodium bicarbonate (2 mL) was added follow by dilute sodium hydroxide. The mixture was warmed to room temperature, extracted several times with ethyl acetate. The combined extracts were dried (MgSO$_4$), concentrated and the residue was purified by column chromatography (SiO$_2$, hexanes-ethyl acetate=1:1) gave 20 (28 mg, 74%) as a colorless solid. mp 129-131° C.; $^1$H NMR (d$_6$-acetone, 300 MHz) δ 8.59 (br s, 1H), 7.40 (d, J=9.0 Hz, 2H), 6.97-6.79 (m, 4H), 6.30 (s, 2H), 4.57 (br s, 2H), 3.05 (br s, 1H); $^{13}$C NMR (d$_6$-acetone, 75 MHz) δ 158.2, 155.9, 154.1, 129.7, 128.6, 127.4, 116.5, 114.9, 109.9, 109.4, 57.4. HRMS (ESI): m/z calcd for C$_{13}$H$_{12}$O$_3$+Na$^+$[M+Na]$^+$ 239.0679, found 239.0681.

4.3 Fluorescence Polarization

Assay was developed based on a commercially available kit from Invitrogen.[15] Assays were run on a BMG POLARstar Galaxy reader with acquisition parameters as follows: 200 flashes, positioning delay 1.0 s, K factor ≤1.1 and ≥0.9, excitation filter of 485±5 nm and emission filter of 520±15 nm. For the IC$_{50}$ determinations the [ER-α] was 30 nM and the [FITC-estradiol tracer] ([Tr]) was 10 nM. Sample volume was 150 µL. For each experiment the polarization was calibrated with a sample of FITC set at 20 mP. All proper blanks were used, including water for the FITC samples and blank samples containing only 30 nM ERα protein for the remaining data points. All protein samples contained 1% d$_6$-DMSO, the maximum amount tolerated as stated by the supplier of the ERα protein, Invitrogen, to ensure the solubility of all hydrophobic compounds investigated. The K$_d$ of the FITC-tagged estradiol for ER-a was determined by non-linear least squares fitting of the titration curve data to the following equation:

4.4 Cell-Based ERα and ERβ Assays

ERα and ERβ assay kits for cell-based assays (Indigo Biosciences) allowed for investigation into the functional activity (i.e. agonist and/or antagonist) of the ligands identified to bind based on the initial fluorescence polarization displacement assay. Briefly, the cells contained a luciferase reporter gene that was functionally linked to either the ERα or ERβ-responsive promoter. By quantifying the luciferase expression via luminescence, the change in ER activity could be quantified. 1-2 mM stocks of the ligands were prepared in d$_6$-DMSO and diluted to final concentrations ranging from 3.2 nM to 2 µM, using the Compound Screening Medium provided in the kit. For the agonist assay, the cells were prepared by warming to 37° C., plated, then the chemicals added. For the antagonist assay, the cells were prepared as above with the addition of E2 (for ERα 3.2 nM was added, approximating an IC$_{75}$; and, for ERβ 160 pM was added, approximating an IC$_{50}$). The cells were then plated, and the chemicals added. All plates were incubated in a cell culture incubator at 37° C. and 5% CO$_2$ for 22 h.

Each assay was performed in duplicate. Luminescence was characterized after removal of the incubating media and introduction of the Detection Substrate using a Molecular Devices SpectraMax M5 microplate reader. Data was fitted using GraphPad Prism and fit to the dose-response (four parameter) equation as follows.

4.5 Molecular Docking

Ligand structures were drawn in PC Spartan Plus (Wavefunction) and three dimensional (3D) conformation was then optimized using semiempirical Austin Model 1 (AM1) calculations. Since compound 13 was afforded as a pair of diastereomers both were modeled and docked. The AM1 calculations provided geometries and bond distances for subsequent docking. AutoDock Tools (ADT) was used prepare the ligand files according to AutoDock requirements and assign Gasteiger charges.

The ERα receptor for agonist (pdb code 1ere)[4] and antagonist (pdb code 1err)[33] conformations were prepared for docking calculations using the 'A' chain. The ERβ receptor for agonist (pdb code 2jj3)[34] and antagonist (pdb code 112j)[35] conformations were prepared for docking calculations using the 'A' chain. ADT was used to further prepare the ER receptor files by adding hydrogen atoms and adding partial charges to each atom of the protein. The grid box was centered on the co-crystallized ligand, drawn to a box to incorporate amino acids Arg394, Glu353, and His524 for ERα and Arg346, Glu305, and His475 for ERβ, then the estradiol ligand was removed.[36] AutoDock (v. 4.2) calculations were performed with default parameters, except with 100 genetic algorithm runs and 2,500,000 evaluations per run.[36-40]

TABLE 3

Docking results for the agonist formation of ERα in the absence of water molecules.

| Compound | Number of Clusters (2.0 Å rmsd) | Lowest Energy Cluster Population | Calculated Binding Energy (kcal mol$^{-1}$) | Mode |
|---|---|---|---|---|
| estradiol | 2 | 69 | −10.74 | reversed |
| estradiol |   | 31 | −10.72 | normal |
| 4 | 2 | 64 | −11.09 | reversed |
| 4 |   | 36 | −10.71 | normal |
| 2 | 1 | 100 | −10.98 | reversed |
| 7 | 2 | 56 | −9.93 | reversed |
| 7 |   | 44 | −9.79 | normal |
| 11 | 3 | 69 | −10.35 | reversed |
| 11 |   | 29 | −9.28 | normal |
| 11 |   | 2 | −9.16 | reversed |
| 10 | 2 | 96 | −9.48 | reversed |
| 10 |   | 4 | −9.08 | normal |
| 13a | 1 | 100 | −7.44 | normal |
| 13b | 1 | 100 | −9.13 | reversed |
| 17 | 3 | 22 | −7.27 | reversed |
| 17 |   | 76 | −7.21 | reversed |
| 17 |   | 2 | −7.12 | normal |
| 20 | 1 | 100 | −7.57 | reversed |
| 18 | 2 | 85 | −7.42 | reversed |
| 18 |   | 15 | −7.34 | normal |
| 14 | 2 | 97 | −6.71 | normal |
| 14 |   | 3 | −6.39 | reversed |
| 15 | 2 | 73 | −6.85 | normal |
| 15 |   | 27 | −6.77 | reversed |
| 16 | 3 | 71 | −7.42 | reversed |
| 16 |   | 28 | −7.33 | normal |
| 16 |   | 1 | −7.17 | normal |

TABLE 4

Docking results for the agonist formation of ER in the presence of a single water molecule near Arg294 and Glu353 as observed in the crystal structure. Chemicals 20 and 14 were not predicted to bind similarly to the normal or reversed modes as otherwise noted.

| Compound | Number of Clusters (2.0 Å rmsd) | Lowest Energy Cluster Population | Calculated Binding Energy (kcal mol$^{-1}$) | Mode |
|---|---|---|---|---|
| estradiol | 1 | 100 | −10.36 | normal |
| 4 | 2 | 97 | −10.29 | reversed |
| 2 | 2 | 42 | −10.16 | normal |
| 2 | 2 | 58 | −9.82 | normal |
| 11 | 1 | 100 | −9.80 | normal |
| 7 | 1 | 100 | −9.74 | normal |
| 10 | 1 | 100 | −8.82 | normal |
| 13b | 1 | 100 | −8.73 | normal |
| 13a | 1 | 100 | −8.39 | normal |
| 4 | 2 | 3 | −7.73 | reversed |
| 18 | 2 | 72 | −7.56 | reversed |
| 18 | 2 | 28 | −7.46 | normal |
| 17 | 2 | 13 | −7.46 | reversed |
| 17 | 2 | 87 | −7.37 | normal |
| 16 | 2 | 97 | −7.27 | normal |
| 15 | 2 | 73 | −7.00 | reversed |
| 16 | 2 | 3 | −6.94 | reversed |
| 20 | 4 | 76 | −6.93 | other |
| 15 | 2 | 27 | −6.85 | normal |
| 14 | 3 | 79 | −6.41 | other |

REFERENCES AND NOTES

1. Manas, E. S.; Xu, Z. B.; Unwalla, R. J.; Somers, W. S. *Structure* 2004, 12, 2197-2207.
2. Levin, E. R. *Mol. Endocrinol.* 2005, 19, 1951-1959.
3. Li, X.; Huang, J.; Yi, P.; Bambara, R. A.; Hilf, R.; Muyan, M. *Mol. Cell. Biol.* 2004, 24, 7681-7694.
4. Brzozowski, A. M.; Pike, A. C. W.; Dauter, Z.; Hubbard, R. E.; Bonn, T.; Engstrom, O.; Ohman, L.; Greene, G. L.; Gustafsson, J. A.; Carlquist, M. *Nature*, 1997, 389, 753-758.
5. Payne, J.; Scholz, M.; Kortenhamp, A. *Environ. Health Perspect.* 2001, 109, 391-397.
6. Blair, R. M.; Fang, H.; Branham, W. S.; Hass, B. S.; Dial, S. L.; Moland, C. L.; Tong, W.; Shi, L.; Perking, R.; Sheehan, D. M. *Toxicol. Sci.* 2000, 54, 138-153.
7. Deroo, B. J.; Korach, K. S. *J. Clin. Invest.* 2006, 116, 561-570.
8. Colborn, T.; Saal, F. S.; Soto, A. M. *Environ. Health Perspect.* 1993, 101, 378-384.
9. Brody, J. G.; Rudel, R. A. *Environ. Health Perspect.* 2003, 111, 1007-1019.
10. Tice, R. "Biomolecular Screening Branch". National Institute of Environmental Health Sciences. NIH, U.S. Dept. of Health and Human Services. Jul. 5, 2013 (http://www.niehs.nih.gov/research/atniehs/labs/bmsb/index.cfm) National Toxicology Program 2001?
11. Nasir, M. S.; Jolley, M. E. *Comb. Chem. High Throughput Screening* 1999, 2, 177-190.
12. Burke, T. J.; Loniello, K. R.; Beebe, J. A.; Ervin, K. M. *Comb. Chem. High Throughput Screening* 2003, 6, 183-194.
13. Ohno, K.; Fukushima, T.; Santa, T.; Waizumi, N.; Tokuyama, H.; Maeda, M.; Imai, K. *Anal. Chem.* 2002, 74, 4391-4396.
14. Suzuki, S.; Ohno, K.; Santa, T.; Imai, K. *Anal. Sci.* 2003, 19, 1103-1108.

15. Parker, G. J.; Law, T. L.; Lenoch, F. J. Bolger, R. E. *J. Biomol. Screen.* 2000, 5, 77-88.
16. Costache, A. D.; Pullela, P. K.; Kashi, P.; Tomasiewicz, H.; Sem, D. S. *Mol. Endocrinol.* 2005, 19, 2979-2990.
17. Bolger, R.; Wiese, T. E.; Ervin, K.; Nestich, S.; Checovich, W. *Environ. Health Perspect.* 1998, 106, 551-557.
18. Shoichet, B. K. *Nature.* 2004, 432, 862-865.
19. Irwin, J. J.; Shoichet, B. K. *J. Chem. Inf Model.* 2005, 45, 177-182.
20. Cavasotto, C. N.; Orry, A. J. W. *Curr. Top. Med. Chem.* 2007, 7 1006-1014.
21. Suresh, P. S.; Kumar, A.; Kumar, R.; Sihn, V. P. *J. Mol. Graphics Modell.* 2008, 26, 845-849.
22. Cross, J. B.; Thompson, D. C.; Rai, B. K.; Baber, J. C.; Fan, K. Y.; Hu, Y.; Humblet, C. *J. Chem. Inf Model.* 2009, 49, 1455-1474.
23. De Riccardis, F.; Meo, D.; Izzo, I.; Di Filippo, M.; Casapullo, A. *Eur. J. Org. Chem.* 1998, 1965-1970.
24. Lam, H. Y. P.; Begleiter, A.; Goldenberg, G. *J. J. Med. Chem.* 1979, 22, 200-202.
25. Li, P. K.; Murakata, C.; Akinaga, S. U.S. Pat. No. 6,288,050, 2001.
26. He, Z.; Donaldson, W. A.; Yi, C. S. *Org. Lett.* 2003, 5, 1567-1569.
27. Frigoli, M.; Mehl, G. H. *Eur. J. Org. Chem.* 2004, 636-642. DeOrazio, R. J.; Nikam, S. S.; Scott, I. L.; Sherer, B. A.; Wise, L. D. PCT Int. Appl. WO 01/81295 A1, 2001.
28. Indigo Biosciences, Human Estrogen Receptor Technical Manual.
29. Pandey, R. K.; Wang, L.; Wallock, N. J.; Lindeman, S.; Donaldson, W. A. *J. Org. Chem.* 2008, 73, 7236-7245.
30. van Lipzig, M. M. H.; ter Laak, A. M.; Jongegan, A.; Vermeulen, N. P. E.; Wamelink, M.; Geerke, D.; Meerman, J. H. N. *J. Med. Chem.* 2004, 47, 1018-1030.
31. Miteva, M. A.; Lee, W. H.; Montes, M. O.; Villoutreix, B. O. *J. Med. Chem.* 2005, 48, 6012-6022.
32. Brzozowski, A. M.; Pike, A. C.; Dauter, Z.; Hubbard, R. E.; Bonn, T.; Engstrom, O.; Ohman, L.; Greene, G. L.; Gustafsson, J. A.; Carquist, M. *Nature.* 1997, 389, 753-758.
33. Norman, B. H.; Richardson, T. I.; Dodge, J. A.; Pfeifer, L. A.; Durst, G. L.; Wang, Y.; Durbin, J. D.; Krishnan, V.; Dinn, S. R.; Liu, S.; Reilly, J. E.; Ryter, K. T. *Bioorg. Med. Chem. Lett.* 2007, 17, 5082-5085.
34. Shiau, A. K.; Barstad, D.; Radek, J. T.; Meyers, M. J.; Nettles, K. W.; Katzenellenbogen, B. S.; Katzellenbogen, J. A.; Agard, D. A.; Greene, G. L. *Nat. Struct. Biol.* 2002, 9, 359-364.
35. Tuccinardi, T.; Bertini, S.; Martinelli, A.; Minutolo, F.; Ortore, G.; Placanica, G.; Prota, G.; Rapposelli, S.; Carleson, K. E.; Katzenellenbogen, J. A.; Macchia, M. *J. Med. Chem.* 2006, 49, 5001-5012.
36. Morris, G. M.; Huey, R.; Lindstrom, W.; Sanner, M. F.; Belew, R. K.; Goodsell, D. S.; Olson, A. J. *J. Comput. Chem.* 2009, 30, 2785-2791.
37. Morris, G. M.; Goodsell, D. S.; Halliday, R. S.; Huey, R.; Hart, W. E.; Belew, R. K.; Olson, A. J. *J. Comput. Chem.* 1998, 19, 1639-1662.
38. Goodsell, D. S.; Morris, G. M.; Olson, A. J. *J. Mol. Recognit.* 1996, 9, 1-5.
39. Huey, R.; Morris, B. M.; Olson, A. J.; Goodsell, D. S. *J. Comput. Chem.* 2007, 28, 1145-1152.
40. Li, Z.; Zhang, H.; Gibson, M.; Li, J. *Toxicology in Vitro* 2012, 26, 769-774.
41. Buteau-Lozano, *Cancer. Res.* 62, 4977-4984, Sep. 1, 2002.
42. Beral V. Breast cancer and hormone-replacement therapy in the Million Women Study. Lancet. 2003; 362(9382):419-27. Epub 2003/08/21. PubMed PMID: 12927427.
43. Gann P H, Morrow M. Combined hormone therapy and breast cancer: a single-edged sword. JAMA: the journal of the American Medical Association. United States2003. p. 3304-6.
44. Li C I, Malone K E, Porter P L, Weiss N S, Tang M T, Cushing-Haugen K L, et al. Relationship between long durations and different regimens of hormone therapy and risk of breast cancer. JAMA: the journal of the American Medical Association. 2003; 289(24):3254-63. Epub 2003/06/26. doi: 10.1001/jama.289.24.3254. PubMed PMID: 12824206.
45. Anderson G L, Limacher M, Assaf A R, Bassford T, Beresford S A, Black H, et al. Effects of conjugated equine estrogen in postmenopausal women with hysterectomy: the Women's Health Initiative randomized controlled trial. JAMA: the journal of the American Medical Association. 2004; 291(14):1701-12. Epub 2004/04/15. doi: 10.1001/jama.291.14.1701. PubMed PMID: 15082697.
46. Song X, Pan Z Z. Estrogen receptor-beta agonist diarylpropionitrile counteracts the estrogenic activity of estrogen receptor-alpha agonist propylpyrazole-triol in the mammary gland of ovariectomized Sprague Dawley rats. The Journal of steroid biochemistry and molecular biology. 2012; 130(1-2):26-35. Epub 2012/01/24. doi: 10.1016/j.jsbmb.2011.12.018. PubMed PMID: 22266284.
47. Leblanc E, Chan B, Nelson H D. U.S. Preventive Services Task Force Evidence Syntheses, formerly Systematic Evidence Reviews. Hormone Replacement Therapy and Cognition. Rockville (Md.): Agency for Healthcare Research and Quality (US); 2002.
48. Yaffe K, Krueger K, Sarkar S, Grady D, Barrett-Connor E, Cox D A, et al. Cognitive function in postmenopausal women treated with raloxifene. New England Journal of Medicine. 2001; 344:1207-13.
49. Paganini-Hill A, Clark L J. Preliminary assessment of cognitive function in breast cancer patients treated with tamoxifen. Breast Cancer Research and Treatment. 2000; 64:165-76.

Example 2. Synthesis and Analysis of Additional Substituted (4'-Hydroxyphenyl)Cycloalkane Compounds 4-(4'-Hydroxyphenyl)-1-methylcyclohexanol

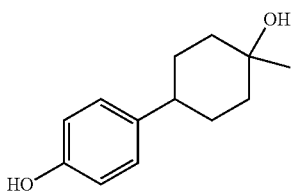

To a solution of 4-(4'-hydroxyphenyl)-cyclohexanone (250 mg, 1.31 mmol) in THF (5 mL) at −78° C. under nitrogen, was added a solution of methylmagnesium bromide (1.76 mL, 3.0 M in ether, 5.3 mmol). The reaction mixture was stirred at −78° C. for 1 h, then warmed to room temperature and quenched with water. The resulting mixture was extracted several times with CH$_2$Cl$_2$ and the combined extracts were washed with brine, dried and concentrated. The residue was recrystallized from acetone/hexanes to give 4-(4'-hydroxyphenyl)-1-methylcyclohexanol (100 mg, 38%) as a colorless solid. mp 140-142° C.; $^1$H NMR (d$_6$-acetone, 300 MHz) δ 8.06 (s, 1H), 7.06 and 6.74 (AA'BB', J$_{AB}$=8.7 Hz, 4H), 2.37 (tt, J=3.3, 12.0 Hz, 1H), 1.91 (dd, J=4.2, 12.9 Hz, 1H), 1.82 (dd, J=4.2, 12.9 Hz, 1H), 1.75-1.41 (m, 6H), 1.19 (s, 3H).

4-(4-t-Butyldiphenylsilyloxyphenyl)cyclohexylidene]-acetic Acid Ethyl Ester

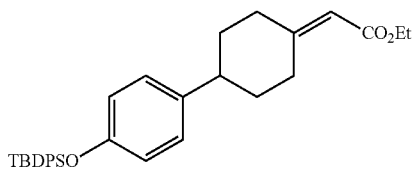

Imidazole (0.537 g, 7.90 mmol) was added to a stirring solution of 4-(4'-hydroxyphenyl)cyclohexanone (0.500 g, 2.63 mmol) in dry DMF (8 mL). After 30 min t-butylchlorodiphenylsilane (1.37 mL, 1.45 g, 5.27 mmol) was added and the reaction mixture was stirred at room temperature for 14 h. Water (30 mL) was then added and the mixture extracted with CH$_2$Cl$_2$, dried and concentrated. The excess DMF was removed under high vacuum and the residue was purified by column chromatography (SiO$_2$, hexanes-ethyl acetate=85:15) to give 4-(4'-t-butyldiphenylsilyloxyphenyl)cyclohexanone (1.02 g, 90%) as a colorless solid. mp=85-86° C. Sodium hydride (43 mg, 55% in mineral oil 0.981 mmol) was added to a stirring solution of triethyl phosphonoacetate (0.183 mg, 0.816 mmol) in dry THF (5 mL) at 0° C. After 30 min, a solution of 4-(4'-t-butyldiphenylsilyloxyphenyl)-cyclohexanone (350 mg, 0.816 mmol) in dry THF (5 mL) was added and the reaction mixture was stirred at room temperature for 2 h. After this time, the mixture was diluted with water (25 mL) and the resulting mixture was extracted with ether, dried and concentrated. The residue was purified by column chromatography (SiO$_2$, hexanes-ethyl acetate=95:05) to give 4-[(4-t-butyldiphenylsilyloxyphenyl)cyclohexylidene]-acetic acid ethyl ester (372 mg, 91%) as a colorless gum.

4-[(4-Hydroxyphenyl)cyclohexylidene]acetic Acid Ethyl Ester

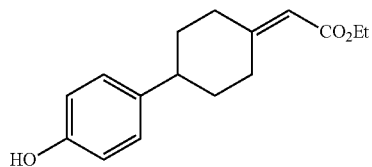 [SMILES: CCOC(=O)C=C1CCC(c2ccc(O)cc2)CC1]

To a stirring solution of 4-[(4-t-butyldiphenylsilyloxyphenyl)cyclohexylidene]acetic acid ethyl ester (60 mg, 0.12 mmol) in dry THF (1 mL) was added a solution of tetrabutylammonium fluoride (0.247 mL, 1.0 M in THF, 0.247 mmol). The solution was stirred at room temperature after 1 h, and then the mixture was diluted with water and extracted with ethyl acetate. The combined extracts were washed with brine, dried and concentrated. The residue was purified by preparative TLC (SiO$_2$, hexanes-ethyl acetate=90:10) to give 4-[(4-hydroxyphenyl)cyclohexylidene]acetic acid ethyl ester (20 mg, 64%) as a colorless solid. mp 92-94° C.; $^1$H NMR (CDCl$_3$, 300 MHz) δ 7.08 and 6.77 (AA'BB', J$_{AB}$=8.4 Hz, 4H), 5.68 (s, 1H), 4.58 (s, 1H), 4.17 (q, J=7.1 Hz, 2H), 4.00-3.90 (m, 1H), 2.80-2.68 (m, 1H), 2.45-1.97 (m, 6H), 1.30 (t, J=7.3 Hz, 3H). $^{13}$C NMR (CDCl$_3$, 75 MHz) δ 167.0, 162.2, 154.0, 138.6, 128.1, 115.4, 113.9, 59.8, 43.4, 37.9, 36.0, 35.2, 29.7, 14.5

4-(4'-Hydroxyphenyl)(2-hydroxyethylidene)cyclohexane

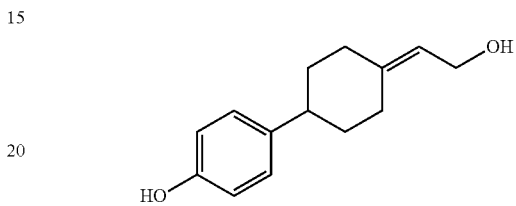

To a solution of 4-[(4-t-butyl-diphenylsilyloxyphenyl)cyclohexylidene]acetic acid ethyl ester (275 mg, 0.551 mmol) in dry dichloromethane (2 mL) under nitrogen at −40° C. was added a solution of diisobutylaluminum hydride (1.41 mL, 1.0 M in CH$_2$Cl$_2$, 1.41 mmol). After 90 min, saturated aqueous potassium sodium tartrate was added and reaction mixture warmed to room temperature. After 2 h the layers were separated and the aqueous layer was extracted several times with CH$_2$Cl$_2$. The combined organic layers were dried, filtered through a pad of celite and concentrated to give 4-(4'-t-butyldiphenylsilyloxyphenyl)(2-hydroxyethylidene)cyclohexane (254 mg, quantitative) as a colorless gum. To a solution of 4-(4'-t-butyldiphenylsilyloxyphenyl)(2-hydroxyethylidene)-cyclohexane (235 mg, 0.514 mmol) in dry THF (1 mL) under nitrogen was added a solution of tetrabutylammonium fluoride in THF (1.03 mL, 1.0 M, 1.03 mmol). The solution was stirred for 3 h and then diluted with water and the resultant mixture extracted several times with ethyl acetate. The combined extracts were washed with brine, dried and concentrated. The residue was purified by column chromatography (SiO$_2$, hexanes-ethyl acetate=80:20) to give 4-(4'-hydroxyphenyl)(2-hydroxyethylidene)cyclohexane (90 mg, 80%) as a colorless solid. mp 165-166° C.; $^1$H NMR (d$_6$-acetone, 300 MHz) δ 8.10 (s, 1H), 7.04 and 6.74 (AA'BB', J$_{AB}$=8.4 Hz, 4H), 5.36 (t, J=6.6 Hz, 1H), 4.17-4.02 (m, 2H), 2.78-2.70 (m, 1H), 2.64 (tt, J=3.3, 12.0 Hz, 1H), 2.35-2.10 (m, 2H), 1.98-1.80 (m, 4H), 1.54-1.37 (m, 2H). $^{13}$C NMR (d$_6$-acetone, 75 MHz) δ 156.5, 141.1, 138.6, 128.5, 123.6, 116.0, 58.5, 44.6, 37.5, 37.0, 36.2, 29.2. Anal. calcd. for C$_{14}$H$_{18}$O$_2$: C, 77.03; H, 8.31. Found: C, 77.20; H, 8.28.

4-[4-(2-Hydroxyethyl)cyclohexyl]phenol and 4-(4-ethylcyclohexyl)phenol

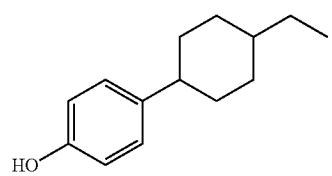

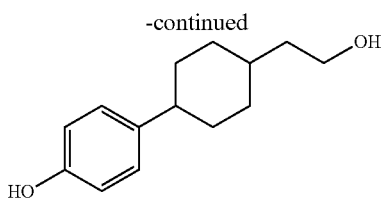

A solution of 4-(4'-hydroxyphenyl)(2-hydroxyethylidene) cyclohexane (50 mg, 0.23 mmol) in methanol (15 mL) with small pinch of 20% Pd/C was stirred under $H_2$ (30 psi) for 12 h. The reaction mixture was filtered through a pad of celite, concentrated and the residue was purified by preparative TLC (SiO$_2$, hexanes-ethyl acetate=65:35) to give 4-(4-ethylcyclohexyl)phenol (28 mg, 60%), followed by 4-[4-(2-hydroxyethyl)cyclohexyl]phenol product (7 mg, 14%) both as colorless solids.

cis- and trans-4-(4-Ethylcyclohexyl)phenol: mp 80-81° C.; $^1$H NMR (CDCl$_3$, 300 MHz) δ 7.08 and 6.76 (AA'BB', $J_{AB}$=8.1 Hz, 4H), 4.55 (s, 1H), 2.54-2.35 (m, 1H), 1.92-1.82 (m, 2H), 1.70-1.50 (m, 3H), 1.45-1.00 (m, 6H), 0.91 (t, J=7.2 Hz, 3H). Anal. calcd. for $C_{14}H_{20}O$: C, 82.30; H, 9.87. Found: C, 81.06; H, 9.52.

cis- and trans-4-[4-(2-Hydroxyethyl)cyclohexyl]phenol: mp 120-125° C.; $^1$H NMR (d$_6$-acetone, 300 MHz) δ 8.02 (s, 1H), 7.08-7.01 (m, 2H), 6.77-6.71 (m, 2H), 3.65-3.56 and 3.43-3.37 (m, 3H total), 2.52-2.33 (m, 1H), 1.91-1.00 (m, 11H).

4-(4'-Hydroxyphenyl)cycloheptanol

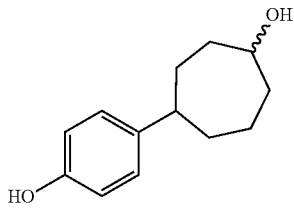 [SMILES: Oc1ccc(C2CCCC(O)CC2)cc1]

To magnesium turnings (3.654 g, 0.1503 mol) and dry THF (30 mL) in a flame dried three-necked flask was added dropwise a small amount of a solution of 4-bromobut-1-ene (7.72 mL, 10.2 g, 0.0756 mol) in THF (20 mL). The reaction mixture was heated to reflux and once the Grignard formation was started, the remaining bromide was added drop-wise maintaining a gentle reflux. The reaction was stirred until most of the magnesium had reacted. A solution of methyl 4-methoxybenzoate (2.528 g, 0.01523 mmol) in THF (30 mL) was added drop-wise over 30 min. After stirring overnight at ambient temperature, saturated aqueous NH$_4$Cl (30 mL) was added to quench the reaction. The resultant emulsion was stirred for 2 h and extracted several times with ether. The combined extracts were washed with water, followed by brine, dried and concentrated to give 5-(4'-methoxyphenyl)-1,8-nonadien-5-ol (3.182 g, 85%) as a yellow oil. $^1$H NMR (CDCl$_3$, 400 MHz) δ 7.28 (dd, J=2.6, 9.0 Hz, 2H), 6.88 (dd, J=2.5, 8.9 Hz, 2H), 5.84-5.73 (m, 2H), 4.98-4.88 (m, 4H), 3.81 (s, 3H), 1.96-1.84 (m, 8H). $^{13}$C NMR (CDCl$_3$, 100 MHz) δ 158.1, 138.9, 126.4, 114.6, 113.4, 76.9, 55.2, 42.1, 28.1. To a solution of 5-(4'-methoxyphenyl)-1,8-nonadien-5-ol (3.20 g, 13.0 mmol) in dry CH$_2$Cl$_2$ (130 mL, 0.01M) was added Grubbs 1$^{st}$ generation catalyst (0.043 g, 0.052 mmol, 4 mol %) and the resultant mixture was heated at 40° C. for 12 h. The mixture was concentrated to dryness and the residue was purified by column chromatography (SiO$_2$, ether-hexanes=80:20) to give 1-(4-methoxyphenyl)-4-cyclohepten-1-ol (1.56 g, 55%) as a green oil. $^1$H NMR (CDCl$_3$, 400 MHz) δ 7.43 (dd, J=2.2, 9.0 Hz, 2H), 6.87 (dd, J=2.2, 9.0 Hz, 2H), 5.86-5.83 (m, 2H), 3.80 (s, 3H), 2.55-2.44 (m, 2H), 2.10-1.97 (m, 4H), 1.90-1.82 (m, 2H). $^{13}$C NMR (CDCl3, 100 MHz) δ 158.3, 142.3, 132.1, 125.8, 113.5, 76.5, 55.2, 40.1, 23.0. To a solution of 1-(4-methoxyphenyl)-4-cyclohepten-1-ol (1.720 g, 7.879 mmol) in dry CH$_2$Cl$_2$ (50 mL) was added triethylsilane (1.35 mL, 8.45 mmol) followed by trifluoroacetic acid (6.20 mL, 80.9 mmol). The mixture was stirred at room temperature for 48 h. After complete disappearance of the starting material, the solution was concentrated and purified by column chromatography (SiO$_2$, hexanes-ethyl acetate=1:1) to give 4-(4-methoxyphenyl)cycloheptene (1.433 g, 86%) as a brown oil. $^1$H NMR (CDCl$_3$, 400 MHz) δ 7.11 (dd, J=1.4, 8.7 Hz, 2H), 6.84 (dd, J=1.6, 8.8 Hz, 2H), 5.91-5.87 (m, 2H), 3.79 (s, 3H), 2.69 (tt, J=3.2, 11.4 Hz, 1H) 2.35-2.25 (m, 2H), 2.23-2.13 (m, 2H), 1.91-1.83 (m, 2H), 1.54-1.43 (m, 2H); $^{13}$C NMR (CDCl$_3$, 100 MHz) δ 157.6, 141.5, 132.5, 125.5, 113.7, 55.2, 49.4, 34.9, 27.9. To a solution of 4-(4-methoxyphenyl)cycloheptene (0.551 g, 2.72 mmol) in freshly distilled CH$_2$Cl$_2$ (20 mL), under nitrogen, was added drop-wise a solution of mCPBA (1.008 g, 70% wt, 4.09 mmol) in freshly distilled CH$_2$Cl$_2$ (10 mL). After the disappearance of starting olefin, as indicted by TLC analysis, the solvent was evaporated and residue was treated with saturated NaHCO$_3$ solution (20 mL) with stirring for 30 min. The mixture was extracted several times with CH$_2$Cl$_2$, and the combined extracts were concentrated. The residue was purified by column chromatography (SiO$_2$, hexane-ethyl acetate=1:1) to give 4-(4-methoxyphenyl)cycloheptene oxide (0.441 g, 74%) as yellow oil. This was revealed to be an equimolar mixture of exo- and endo-stereoisomers. $^1$H NMR (CDCl$_3$, 400 MHz) δ 7.11-7.06 (m, 4H), 6.86-6.80 (m, 4H), 3.78 (s, 3H), 3.77 (s, 3H), 3.16-3.19 (m, 2H), 3.13-3.07 (m, 2H), 2.55 (tt, J=3.3, 11.4 Hz, 1H), 2.40-2.29 (m, 4H), 2.14 (tt, J=2.3, 11.2 Hz, 1H), 1.93-1.84 (m, 2H), 1.83-1.77 (m, 2H), 1.75-1.67 (m, 2H), 1.66-1.57 (m, 4H), 1.50-1.40 (m, 2H); $^{13}$C NMR (CDCl$_3$, 100 MHz) δ 157.8/157.6, 141.2, 139.9, 127.6/127.3, 113.8/113.7, 56.1, 55.1, 49.2, 48.0, 32.6, 32.0, 28.8, 27.5. To a solution of 4-(4-methoxyphenyl) cycloheptene oxide (0.100 g, 0.458 mmol) in dry THF (10 mL), under nitrogen, was added LiAlH$_4$ (48.0 mg, 1.26 mmol) and AlCl$_3$ (56 mg, 0.42 mmol). After stirring for 12 h, the mixture was treated with 15 drops of water and diluted with aqueous KOH (3 mL) and water (10 mL). The mixture was then filtered through celite and extracted several times with ether, and the combined extracts were dried and concentrated. The residue was purified by column chromatography (SiO$_2$, ethyl acetate-hexanes=4:1) to give 4-(4-methoxyphenyl)cycloheptanol (32 mg, 32%) as a yellow oil. This was determined to be a mixture of cis- and trans-stereoisomers by NMR spectroscopy. $^1$H NMR (CDCl$_3$, 400 MHz) δ 7.10 (t, J=7.8 Hz, 2H), 6.83 (d, J=8.2 Hz, 2H), 3.90-3.98/4.00-4.05 (m, 1H), 3.78 (s, 3H), 2.72-2.55 (m, 1H), 2.16-1.48 (m, 11H). $^{13}$C NMR (CDCl$_3$, 400 MHz) δ ppm 157.6, 141.4, 127.5, 113.7, 72.7, 71.6, 55.2, 46.2, 38.2, 37.6, 36.9, 35.7, 31.7, 29.6, 23.3, 21.3. To a solution of 4-(4-methoxyphenyl)cycloheptanol (28 mg, 0.13 mmol) in anhydrous CH$_2$Cl$_2$ (30 mL) cooled to at −78° C., was added drop-wise a solution of boron tribromide (0.25 mL, 1.0 M in CH$_2$Cl$_2$, 0.025 mmol). After the addition was complete, the reaction mixture was stirred for 30 min and then warmed to room temperature over a 2 h period. The mixture was quenched with water (10 mL) and mixture extracted several times with CH$_2$Cl$_2$. The combined extracts were washed with brine, dried and concentrated to give 4-(4-hydroxyphenyl)cycloheptanol (24 mg, 90%) as a yellow solid. This was determined to be a mixture of cis- and trans-stereoisomers by NMR spectroscopy. $^1$H NMR (CDCl$_3$, 400 MHz) δ 7.07-6.98 (m, 2H), 6.77-6.70 (m, 2H), 4.84 (s, OH), 4.55-4.46 and 4.41-4.31 (m, 1H), 2.75-2.57 (m, 1H), 2.51-1.36 (m, 13H). $^{13}$C NMR (CDCl$_3$, 100 MHz) δ 153.5, 141.0, 127.7, 115.9, 56.1, 55.7, 45.9, 45.3, 40.0, 39.4, 39.2, 37.7, 37.6, 36.3, 34.2, 31.3, 25.2, 23.5.

Example 3. Synthesis and Analysis of Additional Substituted (4'-hydroxyphenyl)cycloalkane Compounds 4-(4-((t-Butyldimethylsilyloxy)phenyl)cyclohexan-1-one

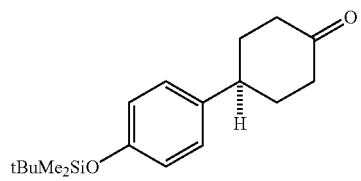

To a stirred solution of 4-(4-hydroxyphenyl)cyclohexanone (0.500 g, 2.62 mmol) in anhydrous dichloromethane (30 mL) at 0° C. under N$_2$ was added imidazole (0.357 g, 5.24 mmol). After 30 min t-butyldimethylsilyl chloride (0.594 g, 3.94 mmol) was added and the mixture was gradually warmed to room temperature overnight. The resulting mixture was diluted with brine, and extracted several with CH$_2$Cl$_2$. The combined organic extracts were dried (Na$_2$SO$_4$) and concentrated. The residue was purified by column chromatography (SiO$_2$, hexanes-ethyl acetate=90:10) to give 4-(4-(t-butyldimethylsilyloxy)phenyl)cyclohexanone (0.664, 83%) as a colorless solid. mp 39-42° C.; $^1$H NMR (CDCl$_3$, 400 MHz) δ 7.08 and 6.78 (AA'BB', J$_{AB}$=8.4 Hz, 4H), 2.96 (t, J=12.3 Hz, 1H), 2.56-2.40 (m, 4H), 2.25-2.14, (m, 2H), 1.97-1.82 (m, 2H), 0.98 (s, 9H), 0.19 (s, 6H); $^{13}$C NMR (CDCl$_3$, 100 MHz) δ 211.6, 154.3, 137.7, 127.7, 120.1, 42.2, 41.6, 34.6, 25.9, 18.4, –4.2.

Ethyl 5-(4-(t-butyldimethylsilyloxy)phenyl)-2-oxo-cycloheptane-1-carboxylate

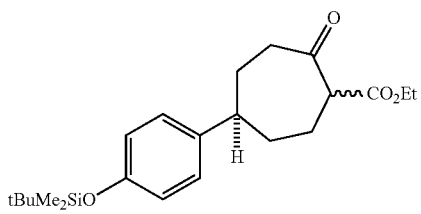

An aliquot of boron trifluoride-etherate (0.92 mL, 7.5 mmol) at 0° C. under N$_2$, was added to a solution of 4-(4-(t-butyldimethylsilyloxy)phenyl)cyclohexanone (1.14 g, 3.74 mmol) in anhydrous diethyl ether (15 mL). A solution of ethyl diazoacetate (0.77 mL, 7.47 mmol) in anhydrous ether (5 mL) was added dropwise over a period of 20 min and the resulting solution was stirred at room temperature for 12 h. The reaction was cooled to 0° C. and neutralized with saturated sodium bicarbonate (20 mL). The resulting mixture was extracted with several times with CHCl$_3$ and the combined organic extracts washed with brine, dried (Na$_2$SO$_4$) and concentrated. The dark yellow crude oil was purified by column chromatography (SiO$_2$, hexanes-diethyl ether=70:30) to give ethyl 5-(4-(t-butyldimethylsilyloxy)phenyl)-2-oxocycloheptane-1-carboxylate (1.182 g, 81%) as a colorless oil. The β-ketoester product is in equilibrium with its keto-enol tautomer. $^1$H NMR (CDCl$_3$, 400 MHz) δ 12.74 (s, 0.4H), 7.02-6.97 (m, 2H), 6.77-6.72 (m, 2H), 4.27-4.16 (m, 2H), 3.64-3.56 (m, 0.3H), 2.94-2.78 (m, 1H), 2.72-2.58 (m, 2H), 2.48-2.24 (m, 1H), 2.16-1.76 (m, 4H), 1.65-1.54 (m, 1H), 1.30 (q, 3H) 0.97 (s, 9H), 0.18 (s, 6H); $^{13}$C NMR (CDCl$_3$, 100 MHz) δ 209.0, 208.8, 178.9, 173.0, 170.6, 154.0, 140.9, 139.9, 127.7, 127.5, 120.2, 120.0, 101.5, 61.4, 60.7, 59.6, 58.5, 49.6, 47.9, 47.2, 42.2, 36.8, 35.4, 34.6, 32.8, 32.2, 27.8, 25.9, 23.9, 22.6, 18.4, 14.5, –4.2.

4-(4-(t-Butyldimethylsilyloxy)phenyl)cycloheptanone

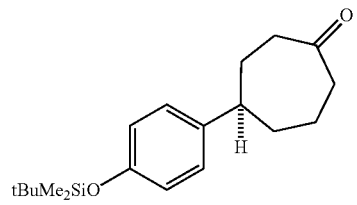

To a stirred solution of ethyl 5-(4-(t-butyldimethylsilyloxy)phenyl)-2-oxocycloheptane-1-carboxylate (0.205 g, 0.525 mmol) in DMSO (20 mL) was added sequentially lithium chloride (0.178 g, 4.20 mmol) and water (3.80 mL). The mixture was heated to reflux at 160° C. for 5 h, cooled to room temperature and poured into water. The resulting solution was extracted several times with ether followed by extraction with ethyl acetate, the combined extracts were washed with brine, dried (Na$_2$SO$_4$) and concentrated to afford 4-(4-(t-butyldimethylsilyloxy)phenyl)-cycloheptanone (0.122 g, 73%) as a colorless oil. $^1$H NMR (CDCl$_3$, 400 MHz) δ 7.01 and 6.75 (AA'BB', J$_{AB}$=8.6 Hz, 4H), 2.72-2.51 (m, 5H), 2.13-2.06 (m, 1H), 2.04-1.95 (m, 2H), 1.86-1.68 (m, 2H), 1.62-1.52 (m, 1H), 0.97 (s, 9H), 0.18 (s, 6H); $^{13}$C NMR (CDCl$_3$, 100 MHz) δ 215.3, 153.9, 140.6, 127.5, 120.1, 48.1, 44.0, 43.1, 38.7, 32.2, 25.9, 24.1, 18.3, –4.2.

t-Butyldimethyl(4-(4-methylenecycloheptyl)phenoxy)silane

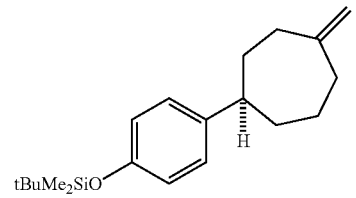

To a stirred solution of methyltriphenylphosphonium bromide (0.476 g, 1.33 mmol) in anhydrous THF (20 mL) under N₂ at −10° C., was added dropwise a solution of n-butyl lithium in hexanes (1.6 M, 0.83 mL, 1.3 mmol). After complete addition, the deep yellow mixture was stirred for another 45 min. A solution of 4-(4-t-butyldimethylsilyloxyphenyl)cycloheptanone (0.212 g, 0.666 mmol) in THF (10 mL) was added dropwise. The solution changed from a deep yellow to light yellow in color, and the mixture was allowed to gradually warm to room temperature and stir overnight. The solution was diluted with water and extracted several times with ethyl acetate. The combined organic extracts were washed with brine, dried (Na₂SO₄) and concentrated. The residue was purified by column chromatography (SiO₂, hexanes-ethyl acetate=90:10) to give t-butyldimethyl(4-(4-methylenecycloheptyl)phenoxy)silane (0.120 g, 57%) as a light yellow oil. ¹H NMR (CDCl₃, 400 MHz) δ 7.03 and 6.75 (AA'BB', $J_{AB}$=8.7 Hz, 4H), 4.76 (s, 2H), 2.59-2.45 (m, 2H), 2.37-2.26 (m, 2H), 2.01-1.85 (m, 3H), 1.70-1.48 (m, 4H), 1.00 (s, 9H), 0.20 (s, 6H); ¹³C NMR (CDCl₃, 100 MHz) δ 153.4, 151.9, 142.3, 127.7, 120.0, 110.7, 47.6, 40.0, 37.2, 36.3, 35.4, 27.6, 25.9, 18.4, −4.2.

Cis- and trans-(4-(4-t-Butyldimethylsilyloxyphenyl)-1-hydroxymethylcycloheptane

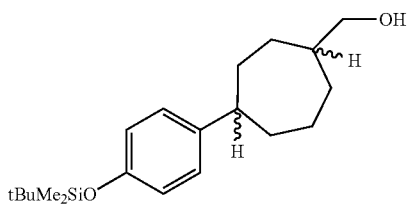

To a solution of t-butyldimethyl(4-(4-methylenecycloheptyl)phenoxy)silane (0.821 g, 2.60 mmol) in freshly distilled THF (10 mL) at 0° C., was added dropwise a solution of borane-tetrahydrofuran complex in THF (1M, 5.4 mL, 5.4 mmol). The resulting mixture was allowed to warm to room temperature and stirred for 18 h. The reaction mixture was cooled to 0° C., and iN sodium hydroxide (3.2 mL) was added slowly followed by 30% hydrogen peroxide (1.5 mL). The mixture was stirred for 1 h at room temperature, extracted several times with ethyl acetate, and the combined extracts dried (Na₂SO₄) and concentrated. The residue was purified by column chromatography (SiO₂, hexanes-ethyl acetate=80:20) to give (4-(4-((t-butyldimethylsilyl)oxy)phenyl)cycloheptyl)methanol (0.572 g, 66%) as a colorless oil. This was determined to be a mixture of cis- and trans-diastereoisomers by ¹H and ¹³C NMR spectroscopy. ¹H NMR (CDCl₃, 400 MHz) δ 7.02 and 6.74 (AA'BB', $J_{AB}$=8.3 Hz, 4H), 3.45 (d, J=6.5 Hz, 2H), 2.67-2.53 (m, 1H), 1.98-1.38 (m, 11H), 1.29-1.09 (m, 1H), 0.98 (s, 9H), 0.19 (s, 6H); ¹³C NMR (CDCl₃, 100 MHz) δ 153.5, 142.6, 142.4, 127.6, 127.5, 119.9, 68.7, 68.5, 47.3, 46.1, 42.2, 41.2, 38.9, 36.8, 36.4, 33.1, 31.5, 30.7, 30.0, 28.5, 27.6, 26.1, 24.2, 18.3, −4.2.

Cis- and trans-4-(4-(Hydroxyphenyl)-1-hydroxymethylcycloheptane

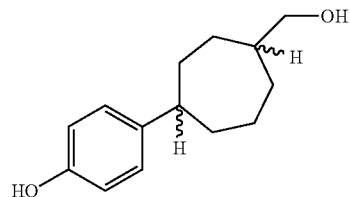 [SMILES: OCC1CCCC(c2ccc(O)cc2)CC1]

To a mixture of cis- and trans-(4-(4-t-Butyldimethylsilyloxyphenyl)-1-hydroxymethylcycloheptane (0.873 g, 0.261 mmol) in anhydrous THF (20 mL) was added a solution of tetra(n-butyl)ammonium fluoride in THF (1M, 10.0 mL, 0.010 mol). The mixture was heated to reflux at 70° C. for 18 h. After cooling to room temperature, the reaction mixture was partitioned between ethyl acetate and water. The organic layer was washed with brine, dried (Na₂SO₄) and concentrated. The residue was purified by column chromatography (SiO₂, hexanes-ethyl acetate=60:40) to give a mixture of cis- and trans-4-(4-(hydroxyphenyl)-1-hydroxymethylcycloheptane (0.508 g, 99%) as a colorless solid. mp 60-63° C.; ¹H NMR (CDCl₃, 400 MHz) δ 7.03 and 6.74 (AA'BB', $J_{AB}$=8.5 Hz, 4H), 3.48 (d, J=6.6 Hz, 2H), 2.67-2.49 (m, 1H), 1.97-1.32 (m, 12H); ¹³C NMR (CDCl₃, 100 MHz) δ 153.8, 142.0, 127.9, 127.8, 68.6, 47.2, 46.1, 45.9, 42.2, 41.3, 38.9, 36.7, 36.5, 33.0, 31.5, 30.6, 29.9, 28.5, 27.4, 24.3.

t-Butyldimethyl(4-(4-methylenecyclohexyl)phenoxy)silane

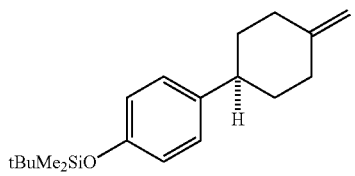

A solution of n-butyllithium in hexane (1.6 M, 1.50 mL, 2.34 mmol) was added to a stirring solution of methyltriphenylphosphonium bromide (0.836 g, 2.34 mmol) in dry THF (20 mL) at −10° C. After 30 min, a solution of 4-(4-(t-butyldimethylsilyloxy)phenyl)cyclohexan-1-one (0.503 g, 1.65 mmol) in dry THF (8 mL) was added dropwise. The reaction mixture was slowly warmed to room temperature and stirred overnight. After this time, the mixture was diluted with water, extracted several times with ethyl acetate, dried (Na₂SO₄) and concentrated. The residue was purified by column chromatography (SiO₂, hexanes-ethyl acetate=90:10) to give t-butyldimethyl(4-(4-methylenecyclohexyl)phenoxy)silane (0.350 g, 67%) as a colorless oil. ¹H NMR (CDCl₃, 400 MHz) δ 7.06 and 6.77 (AA'BB', $J_{AB}$=8.3 Hz, 4H), 4.68 (s, 2H), 2.62 (tt, J=12.1, 3.4 Hz, 1H), 2.42 (broad d, J=13.5 Hz, 2H), 2.18 (broad t, J=13.2 Hz, 2H), 2.00-1.93 (m, 2H), 1.57-1.45 (m, 2H), 0.99 (s, 9H), 0.20 (s, 6H); ¹³C NMR (CDCl₃, 100 MHz) δ 153.9, 149.2, 139.8, 127.8, 119.9, 107.4, 43.5, 36.0, 35.4, 25.9, 18.4, −4.2.

4-(4-Hydroxyphenyl)-1-hydroxymethylcyclohexane

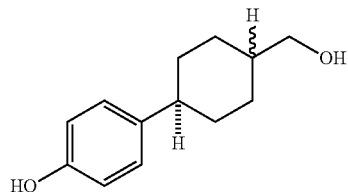

A solution of borane-THF complex in THF (1M, 2.32 mL, 2.32 mmol) was added to a solution of t-butyldimethyl(4-(4-methylenecyclohexyl)phenoxy)silane (0.350 g, 1.10 mmol) in THF (10 mL) at 0° C. The reaction mixture was slowly warmed to room temperature and stirred for 20 h. The mixture was then cooled to 0° C., followed by sequential addition of ethanol (50 mL), hydrogen peroxide solution (30% in water, 1.00 mL) and 3N NaOH solution (5.0 mL). The mixture was warmed to room temperature and stirred for 30 min. The reaction mixture was extracted several times with ethyl acetate, and the combined extracts washed with brine, dried ($Na_2SO_4$), and concentrated. The residue was purified by column chromatography ($SiO_2$, hexanes-ethyl acetate=65:35) to give 4-(4-hydroxyphenyl)-1-hydroxymethylcyclohexane (0.095 g, 47%) as a colorless solid. mp 118-122° C.; $^1H$ NMR ($CD_3OD$, 400 MHz) δ 7.04-6.98 (m, 2H), 6.70-6.65 (m, 2H), 3.60 (d, J=7.6 Hz, 1.5H), 3.39 (d, J=6.6 Hz, 0.5H), 2.54-2.44 (m, 1H), 2.37 (tt, J=12.1, 3.4 Hz, 1H), 1.93-1.70 (m, 3H), 1.61 (d, J=6.3 Hz, 4H), 1.46-1.37 (m, 1H), 1.14-1.02 (m, 1H); $^{13}C$ NMR ($CD_3OD$, 100 MHz) δ 156.2, 139.6, 128.7, 116.0, 68.0, 64.4, 45.2, 44.0, 41.4, 37.0, 35.4, 31.2, 30.5, 28.0.

Example 4. Selective ERb Agonist Activity of 4-(4-Hydroxyphenyl)-1-hydroxymethylcyclohexane The biological activity of 4-(4-Hydroxyphenyl)-1-hydroxymethylcyclohexane was tested in assays for ERβ agonist activity, ERβ antagonist activity, ERα agonist activity and ERα antagonist activity using methods disclosed herein.

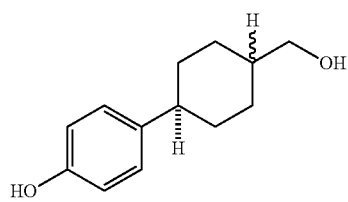

4-(4-Hydroxyphenyl)-1-hydroxymethylcyclohexane

The results are presented in Figure??

Example 5. Biological Activity of Substituted (4'-hydroxyphenyl)cycloalkane Compounds The biological activities of the following compounds were tested in cell-based ERβ agonist/antagonist assays and ERα agonist/antagonist assays as described herein.

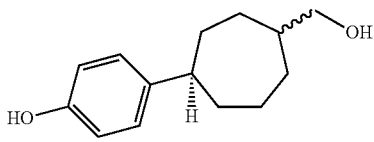
ISP-163

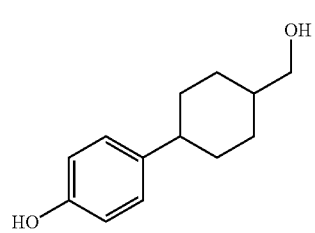 [SMILES: OCC1CCC(c2ccc(O)cc2)CC1]
ISP-171

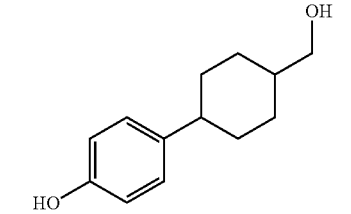
ISP-166

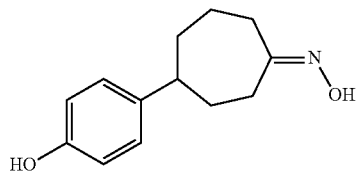
ISP-248

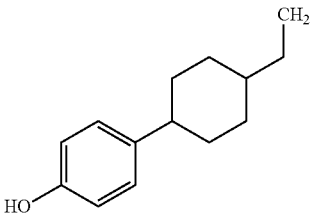
RKP-231 IF

The results are presented in the following Tables:

| Receptor | Activity | ISP-163 | ISP-171 | ISP-166 |
|---|---|---|---|---|
| ERβ | Agonist (E2) | 30 ± 9 nM<br>33 ± 11 nM | 50 ± 2 nM | 731 ± 85 nM |
|  | Antagonist (+E2) | >100 μM | >10 μM | >10 μM |
| ERα | Agonist (E2) | >10 μM | >10 μM | >10 μM |
|  | Normalized Agonist (E2) | 10.5 ± 0.2 μM | 700 ± 80 μM | 350 ± 250 μM |
|  | Antagonist (+E2) | >10 μM | >10 μM | >10 μM |

| Receptor | Activity | ISP-248 | RKP-231 IF |
|---|---|---|---|
| ERβ | Agonist (E2) | 142 ± 17 nM<br>(104 ± 27 nM normalized) | 93 ± 7 nM<br>(89 ± 6 nM normalized) |
|  | Antagonist (+E2) | >10 μM | >10 μM |

-continued

| Receptor | Activity | ISP-248 | RKP-231 IF |
|---|---|---|---|
| ERα | Agonist (E2) | >10 μM | >10 μM |
|  | Normalized Agonist (E2) | 45 ± 17 μM | 25 ± 1.3 μM |
|  | Antagonist (+E2) | >10 μM | >10 μM |

Figure 12:
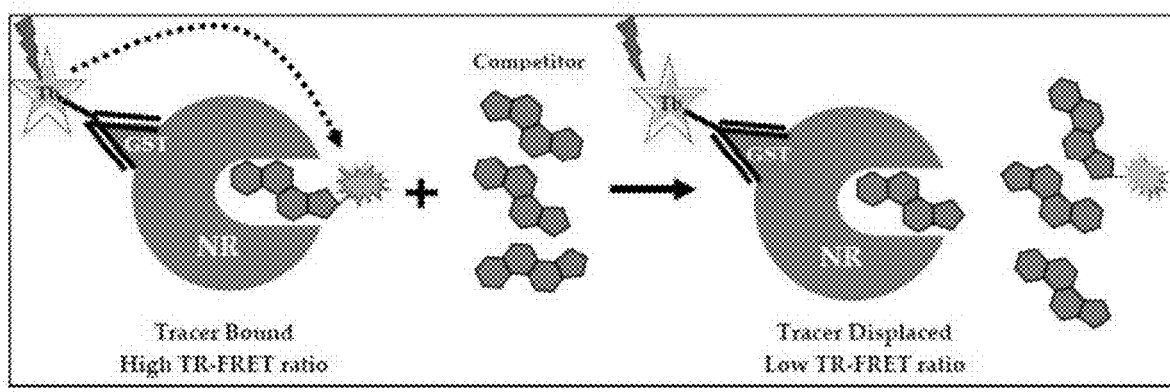
FIG. 12. Illustration of TR-FRET ERβ Binding Assay.

Example 6. Binding Activity of Substituted (4'-hydroxyphenyl)cycloalkane Compounds The binding activity of substituted (4'-hydroxyphenyl)cycloalkane compounds was tested using a TR-FRET ERβ binding assay as illustrated in FIG. 12. The emission of terbium at 488 nm and fluorescein at 518 nm was measured and the TR-FRET ratio was calculated as 518 nm/488 nm. When the tracer used in the assay is bound, then the ratio is high. When the tracer is displaced, the ratio is low. The following compounds were tested.

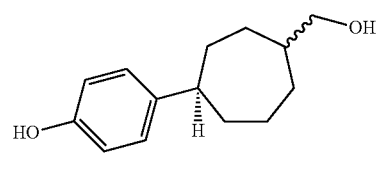

ISP-163

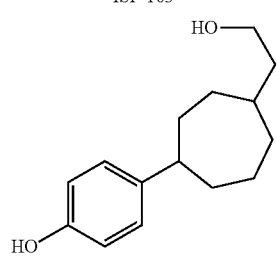

ISP-248

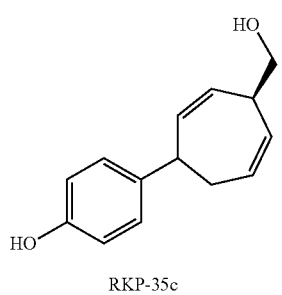

RKP-35c

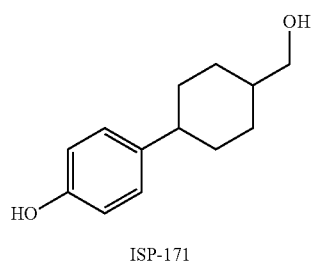

ISP-171

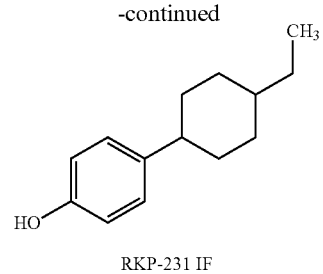

RKP-231 IF

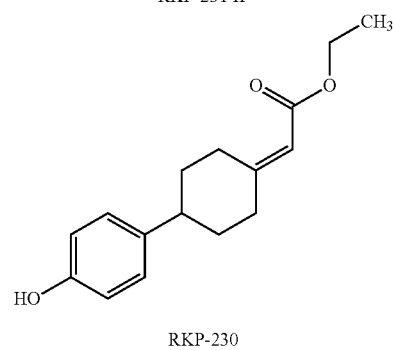

RKP-230

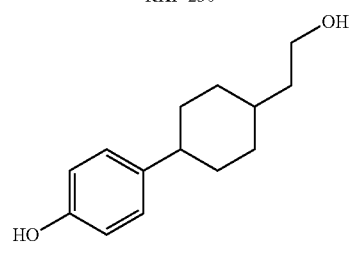

RKP-231 IIF

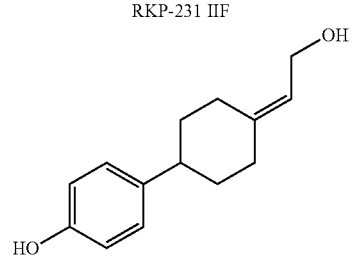

RKP-228

The results are presented in the following Table:

| Compound | IC50 (nM) |
|---|---|
| ISP-163 | 23.5 ± 8 |
| ISP-248 | 36.8 ± 9.2 |
| ISP-171 | 260 ± 42 |
| RKP-35c | 378 ± 97 |
| RKP-228 | 521 ± 87 |
| RKP-230 | 681 ± 240 |
| RKP-231 IF | 15.2 ± 1.5 |
| RKP-231 IIF | 7.0 ± 1.2 |

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A compound of a Formula Ia below or a pharmaceutically acceptable salt thereof:

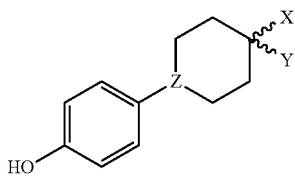

Ia wherein:
X is hydroxyl, hydroxymethyl, or aminoethyl;
Y is hydrogen or alkyl, provided that when X is hydroxyl then Y is not hydrogen; or
X and Y together form hydroxyalkylidenyl, aminoalkylidenyl, or oxime; and
Z is CH.

2. The compound of claim 1, wherein X is hydroxymethyl.

3. The compound of claim 2, wherein Y is hydrogen or alkyl.

4. The compound of claim 1, wherein the compound has a formula:

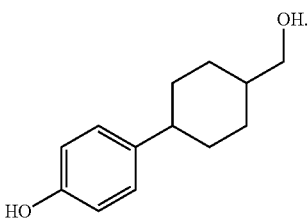

5. The compound of claim 1, wherein X is hydroxyl and Y is alkyl.

6. The compound of claim 1, wherein the compound has a formula selected from:

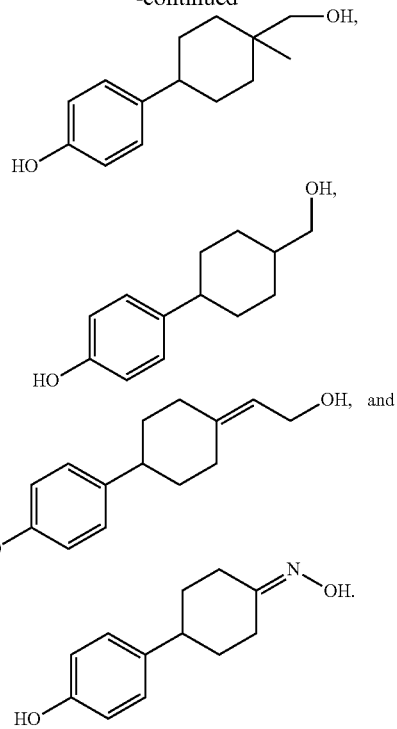

7. A pharmaceutical composition comprising a suitable carrier and the compound of claim 1.

8. A pharmaceutical composition comprising a suitable carrier and the compound of claim 4.

9. A method for treating a patient a disease or disorder associated with estrogen receptor β (ERβ) activity, the method comprising administering to the patient the pharmaceutical composition of claim 7.

10. The method of claim 9, wherein the disease or disorder is a psychiatric disease or disorder.

11. The method of claim 9, wherein the disease or disorder is a cell proliferative disease or disorder.

12. A method for treating a patient a disease or disorder associated with estrogen receptor β (ERβ) activity, the method comprising administering to the patient the pharmaceutical composition of claim 8.

13. The method of claim 12, wherein the disease or disorder is a psychiatric disease or disorder.

14. The method of claim 12, wherein the disease or disorder is a cell proliferative disease or disorder.

15. The compound of claim 1, wherein the compound has a formula:

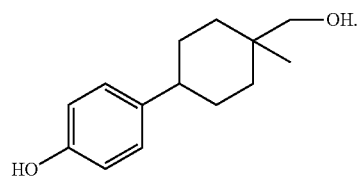 [SMILES: CC1(CO)CCC(c2ccc(O)cc2)CC1]

16. A pharmaceutical composition comprising a suitable carrier and the compound of claim 15.

17. A method for treating a patient a disease or disorder associated with estrogen receptor β (ERβ) activity, the method comprising administering to the patient the pharmaceutical composition of claim 16.

18. The method of claim 17, wherein the disease or disorder is a psychiatric disease or disorder.

19. The method of claim 17, wherein the disease or disorder is a cell proliferative disease or disorder.

* * * * *

UNITED STATES PATENT AND TRADEMARK OFFICE
CERTIFICATE OF CORRECTION

PATENT NO. : 10,570,077 B2
APPLICATION NO. : 15/162057
DATED : February 25, 2020
INVENTOR(S) : William A. Donaldson et al.

It is certified that error appears in the above-identified patent and that said Letters Patent is hereby corrected as shown below:

In the Specification

Column 32, Line 57, "$[a]_p^{20}$" should be --$[\alpha]_p^{20}$--.

Column 33, Line 9, "$[a]_p^{20}$" should be --$[\alpha]_p^{20}$--.

Column 33, Line 32, "$[a]_p^{20}$" should be --$[\alpha]_p^{20}$--.

Column 33, Line 51, "$[a]_p^{20}$" should be --$[\alpha]_p^{20}$--.

Column 34, Line 31, "$[a]_p^{20}$" should be --$[\alpha]_p^{20}$--.

Column 36, Line 43, "ER-a" should be --ER-α--.

Column 36, Line 65, "$IC_{50}$" should be --$IC_{80}$--.

Column 47, Line 50, "iN" should be --1N--.

Signed and Sealed this
Fourteenth Day of July, 2020

Andrei Iancu
*Director of the United States Patent and Trademark Office*